US012605178B2

(12) United States Patent
Ammerman et al.

(10) Patent No.: US 12,605,178 B2
(45) Date of Patent: Apr. 21, 2026

(54) DISCECTOMY TOOL

(71) Applicant: Combination Spine, Inc., Bethesda, MD (US)

(72) Inventors: Joshua M. Ammerman, Bethesda, MD (US); Richard Briganti, Bala Cynwyd, PA (US)

(73) Assignee: Combination Spine, Inc., Bethesda, MD (US)

( * ) Notice: Subject to any disclaimer, the term of this patent is extended or adjusted under 35 U.S.C. 154(b) by 1254 days.

(21) Appl. No.: 17/143,260

(22) Filed: Jan. 7, 2021

(65) Prior Publication Data

US 2021/0212712 A1     Jul. 15, 2021

Related U.S. Application Data

(60) Provisional application No. 62/961,277, filed on Jan. 15, 2020.

(51) Int. Cl.
| | |
|---|---|
| *A61B 17/32* | (2006.01) |
| *A61F 2/46* | (2006.01) |
| A61B 17/00 | (2006.01) |
| A61F 2/44 | (2006.01) |

(52) U.S. Cl.
CPC ...... *A61B 17/32002* (2013.01); *A61F 2/4601* (2013.01); *A61B 2017/00261* (2013.01); *A61B 2017/00424* (2013.01); *A61F 2/4455* (2013.01)

(58) Field of Classification Search
CPC . A61B 17/32002; A61F 2/4611; A61F 2/4425
See application file for complete search history.

(56) References Cited

U.S. PATENT DOCUMENTS

| | | | |
|---|---|---|---|
| 5,700,292 | A | 12/1997 | Margulies |
| 6,083,228 | A | 7/2000 | Michelson |
| 6,682,534 | B2 | 1/2004 | Patel |
| 7,497,859 | B2 | 3/2009 | Zucherman |
| 7,691,147 | B2 | 4/2010 | Gütlin |
| 7,811,287 | B2 | 10/2010 | Errico |
| 7,988,699 | B2 | 8/2011 | Martz |
| 8,002,776 | B2 | 8/2011 | Liu |
| 8,123,782 | B2 | 2/2012 | Altarac |
| 8,182,535 | B2 | 5/2012 | Kraus |
| 8,328,870 | B2 | 12/2012 | Patel |
| 8,377,063 | B2 | 2/2013 | Michelson |

(Continued)

FOREIGN PATENT DOCUMENTS

| | | |
|---|---|---|
| WO | 03092507 A2 | 11/2003 |
| WO | 2005037078 A2 | 4/2005 |
| WO | 2013130907 A1 | 9/2013 |

*Primary Examiner* — Olivia C Chang
(74) *Attorney, Agent, or Firm* — Cook Alex Ltd.

(57) ABSTRACT

A discectomy device for clearing material out of a disc space of a patient having a body, a first rotatable member at the distal portion of the body, and a second rotatable member at the distal portion of the body spaced from the first rotatable member. A transverse axis passes through the first and second rotatable members. A first mechanism is actuable to rotate the first and second rotatable members about the transverse axis. A mechanism can be provided to expand the rotatable members to increase the distance between the rotatable members. The rotatable members in some versions can be detached from the device for placement within the disc space.

29 Claims, 45 Drawing Sheets

(56)                  References Cited

U.S. PATENT DOCUMENTS

| | | | |
|---|---|---|---|
| 8,454,623 B2 | 6/2013 | Patel | |
| 8,911,441 B2 | 12/2014 | Dace | |
| 9,125,757 B2 | 9/2015 | Weiman | |
| 9,216,024 B2 | 12/2015 | Geisert | |
| 9,254,138 B2 | 2/2016 | Siegal | |
| 9,364,241 B2 | 6/2016 | Suddaby | |
| 9,480,502 B2 | 11/2016 | Whiton | |
| 9,498,270 B2 | 11/2016 | Jimenez | |
| 9,642,631 B2 | 5/2017 | Lee | |
| 9,907,564 B2 | 3/2018 | Lockard | |
| 10,022,245 B2 | 7/2018 | Frasier | |
| 10,064,644 B2 | 9/2018 | Schmitz | |
| 10,258,479 B2 | 4/2019 | Stewart | |
| 10,278,744 B2 | 5/2019 | Altarac | |
| 10,398,427 B2 | 9/2019 | Dineen | |
| 10,441,433 B2 | 10/2019 | Patel | |
| 10,603,186 B2 | 3/2020 | Bernhardt, Jr. | |
| 10,682,241 B2 | 6/2020 | Glerum | |
| 10,835,295 B2 | 11/2020 | Altarac | |
| 10,939,934 B2 | 3/2021 | Lockard | |
| 11,026,803 B2 | 6/2021 | Hansell | |
| 11,090,167 B2 | 8/2021 | Emerick | |
| 11,426,290 B2 | 8/2022 | Miller | |
| 11,439,517 B2 | 9/2022 | Mcluen | |
| 11,452,619 B2 | 9/2022 | Moskowitz | |
| 11,458,025 B2 | 10/2022 | Bannigan | |
| 11,612,496 B2 | 3/2023 | Jimenez | |
| 11,957,599 B2 | 4/2024 | Nichols | |
| 2003/0130662 A1* | 7/2003 | Michelson | A61B 17/1671 |
| | | | 606/176 |
| 2005/0021144 A1* | 1/2005 | Malberg | A61F 2/4455 |
| | | | 623/17.13 |
| 2008/0103597 A1* | 5/2008 | Lechmann | A61F 2/4611 |
| | | | 623/17.16 |
| 2009/0005821 A1 | 1/2009 | Chirico | |
| 2009/0149959 A1 | 6/2009 | Conner | |
| 2011/0046679 A1 | 2/2011 | Chow | |
| 2014/0012387 A1 | 1/2014 | Glazer | |
| 2014/0046373 A1 | 2/2014 | Brennan | |
| 2014/0074170 A1 | 3/2014 | Mertens | |
| 2018/0243104 A1 | 8/2018 | Garonzik | |
| 2018/0311473 A1 | 11/2018 | Laby | |
| 2020/0138493 A1 | 5/2020 | Meyer | |
| 2020/0360185 A1 | 11/2020 | Carter | |
| 2023/0051745 A1 | 2/2023 | Pacheco-Serrant | |
| 2023/0157711 A1 | 5/2023 | Predick | |

* cited by examiner

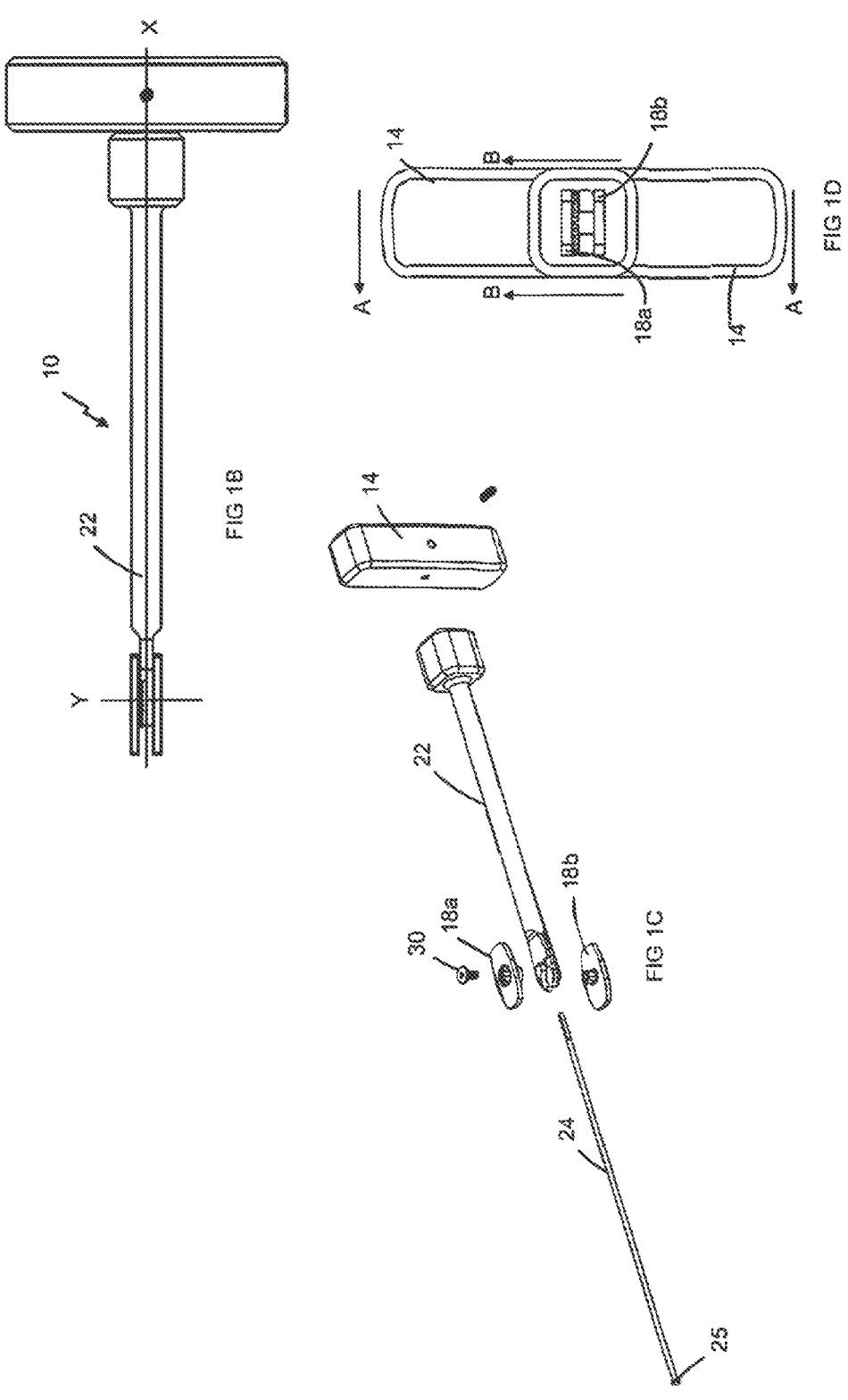

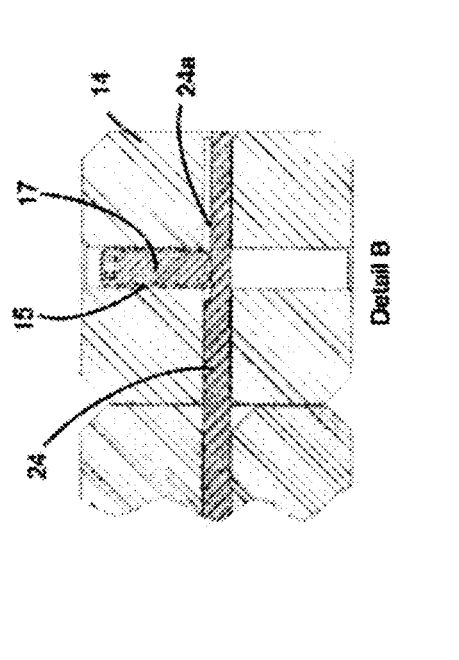
FIG. 2B
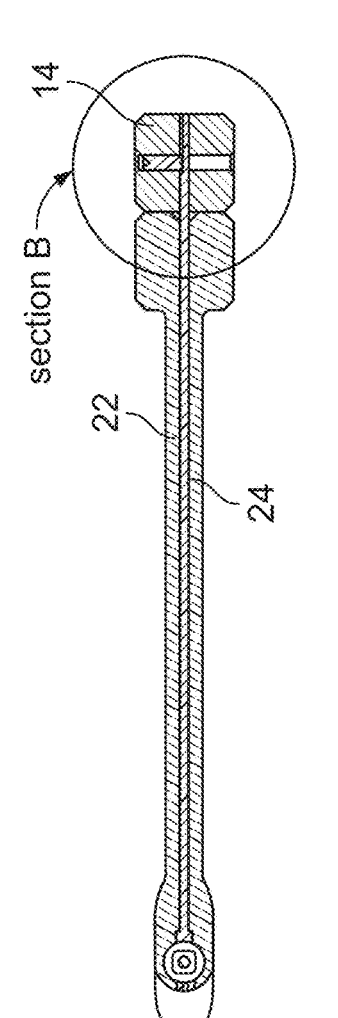
FIG. 2D
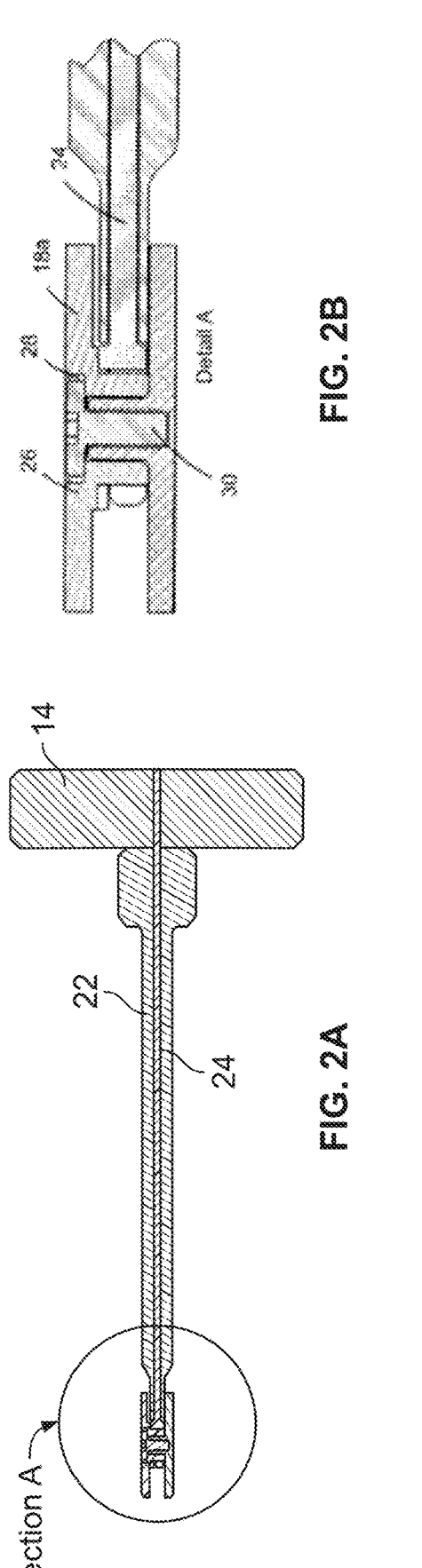
FIG. 2A
FIG. 2C

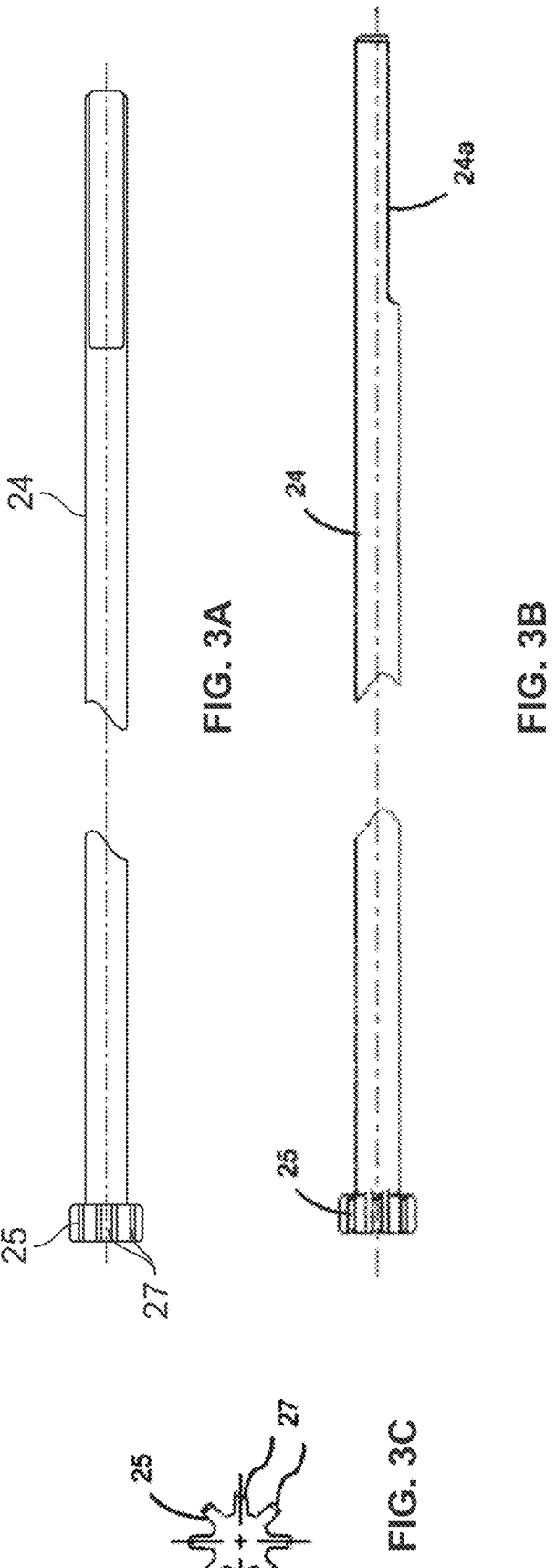

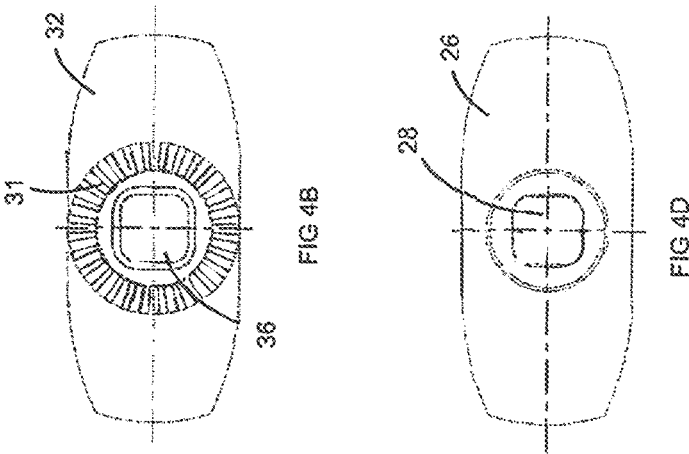
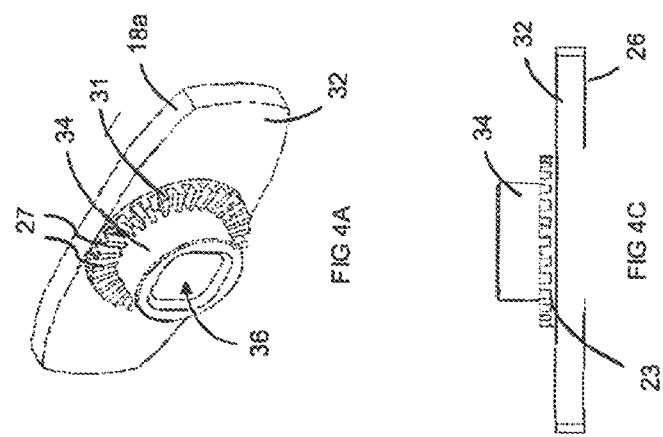

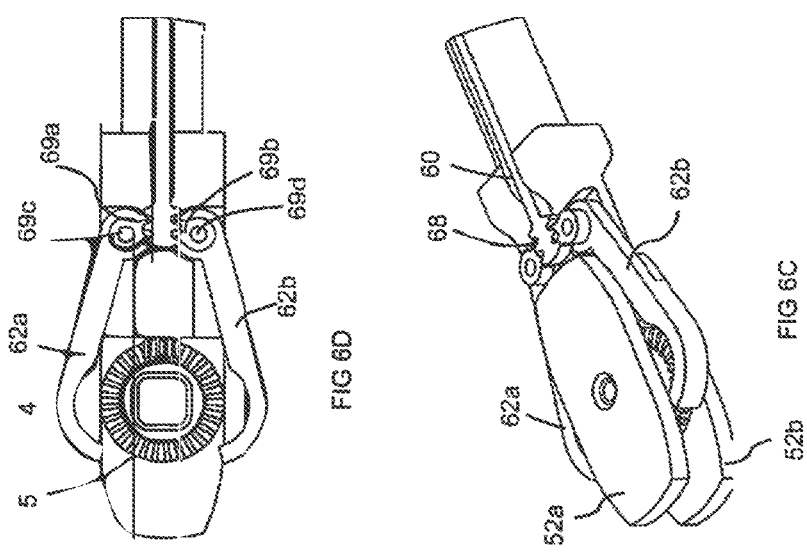
FIG 6D
FIG 6C
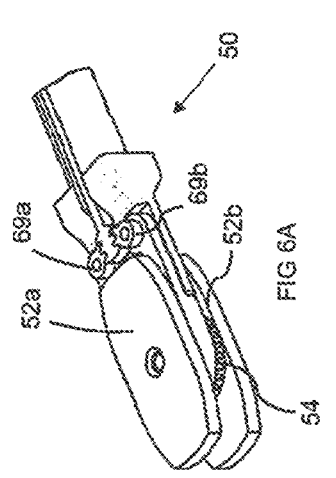
FIG 6A
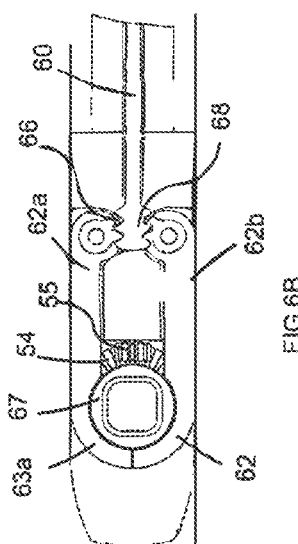
FIG 6B

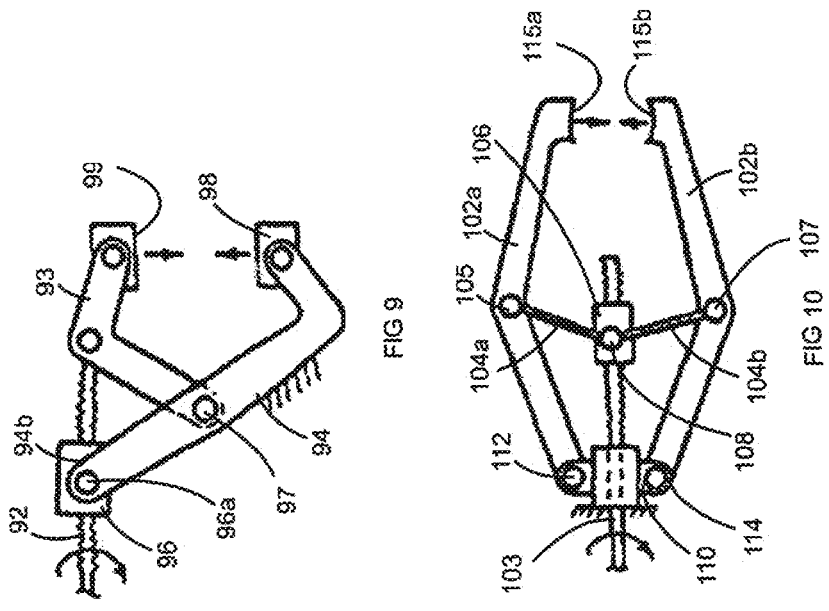
FIG 9
FIG 10
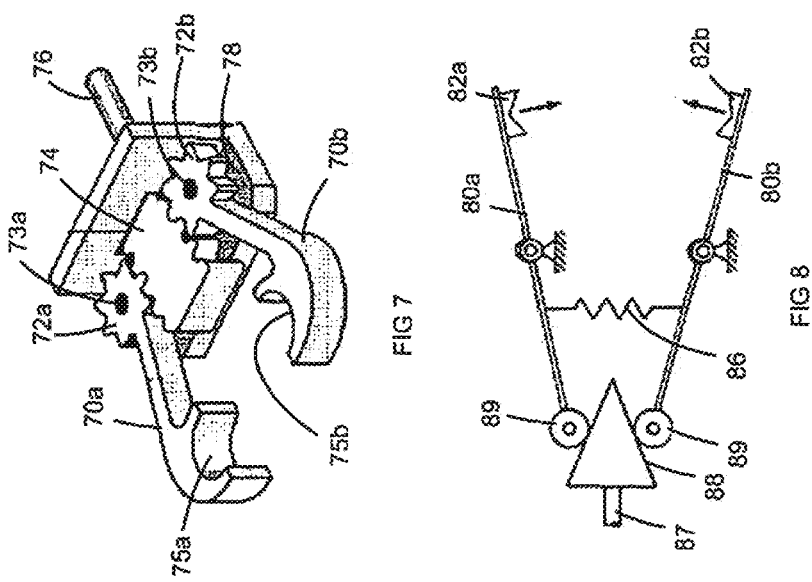
FIG 7
FIG 8

SECTION A-A

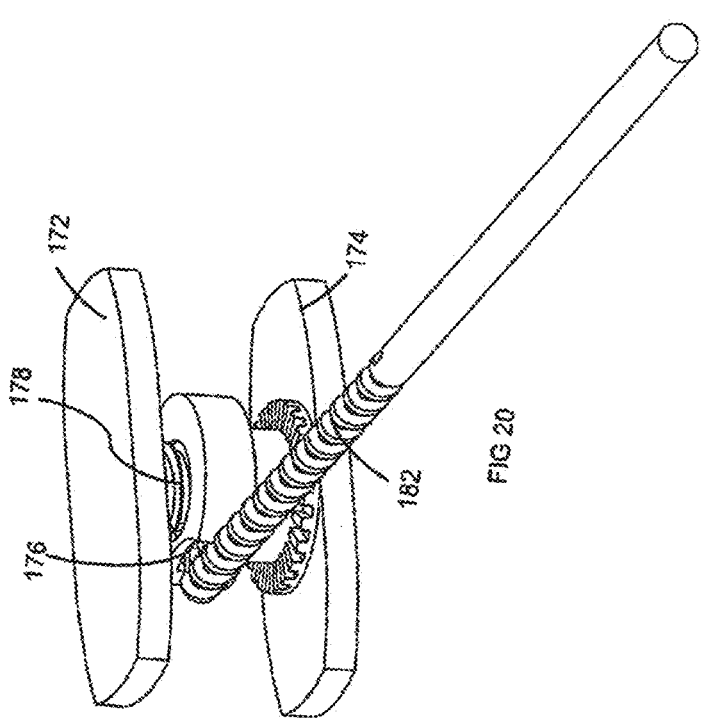
FIG 20
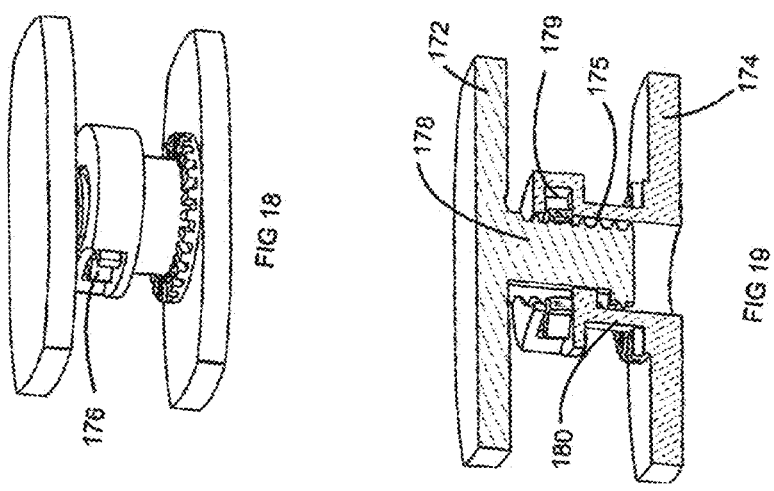
FIG 18
FIG 19

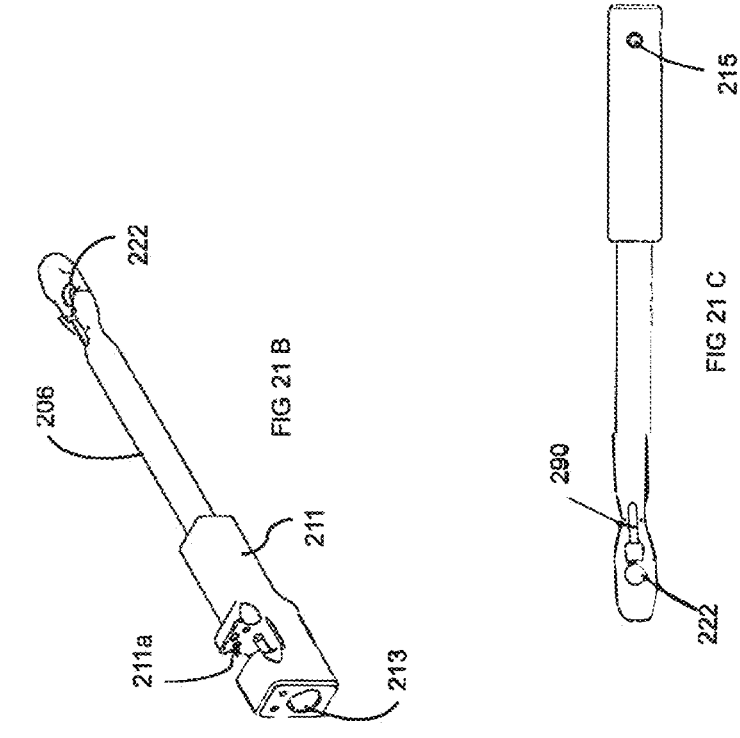
FIG 21 B
FIG 21 C
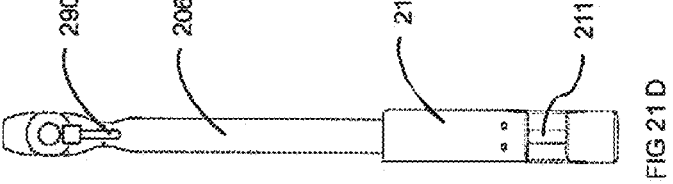
FIG 21 D
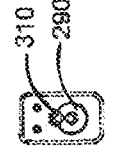
FIG 21 E

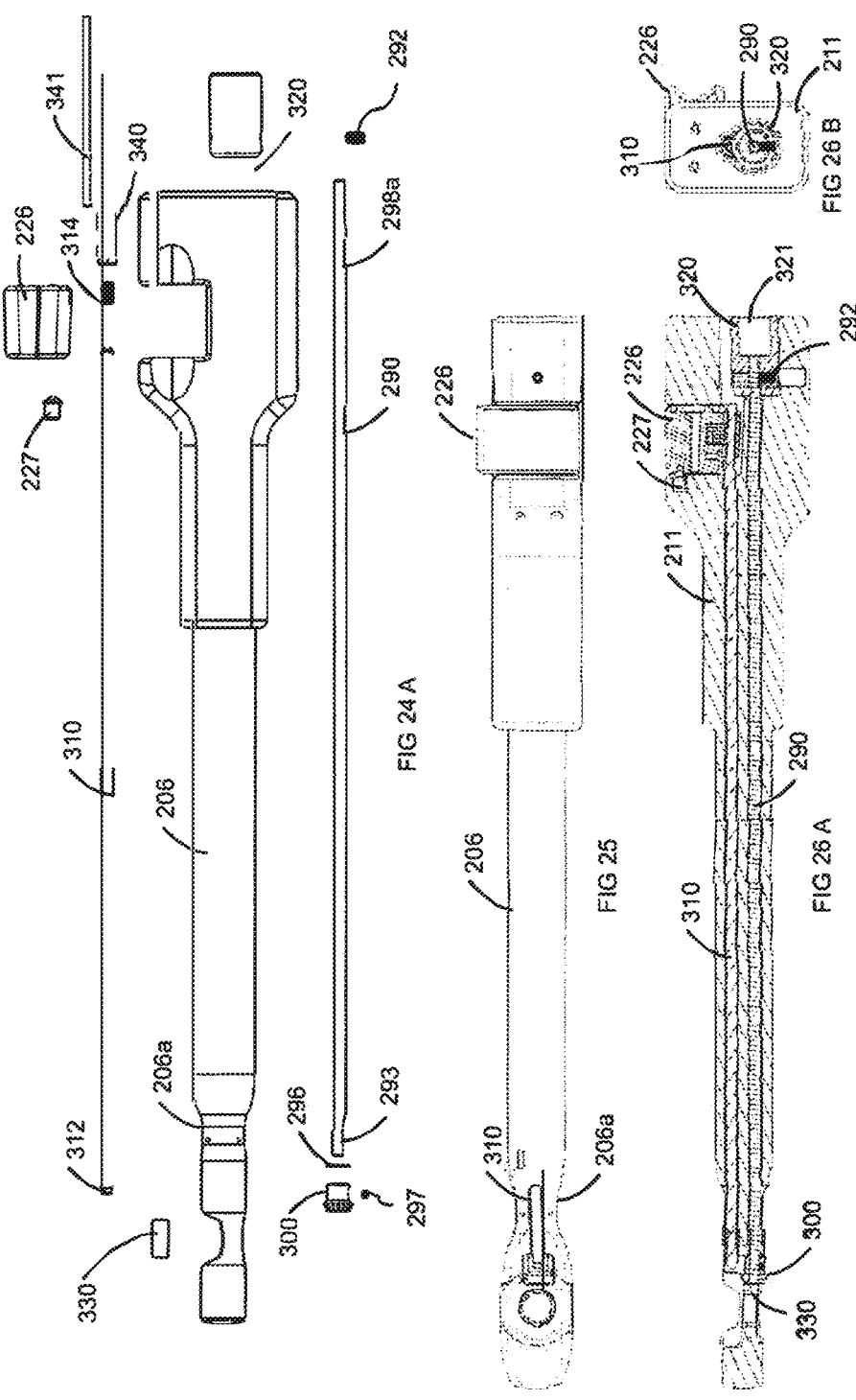

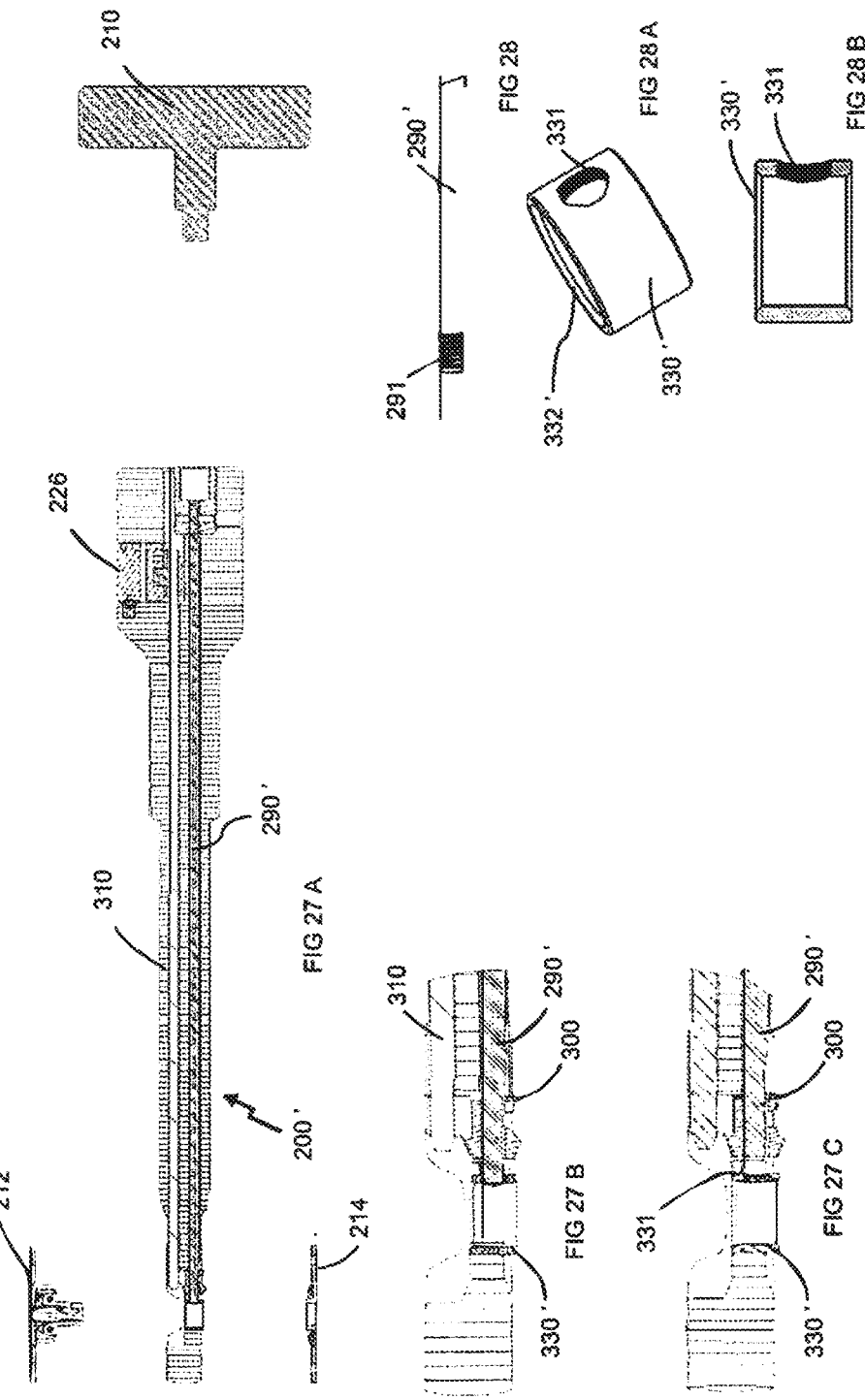

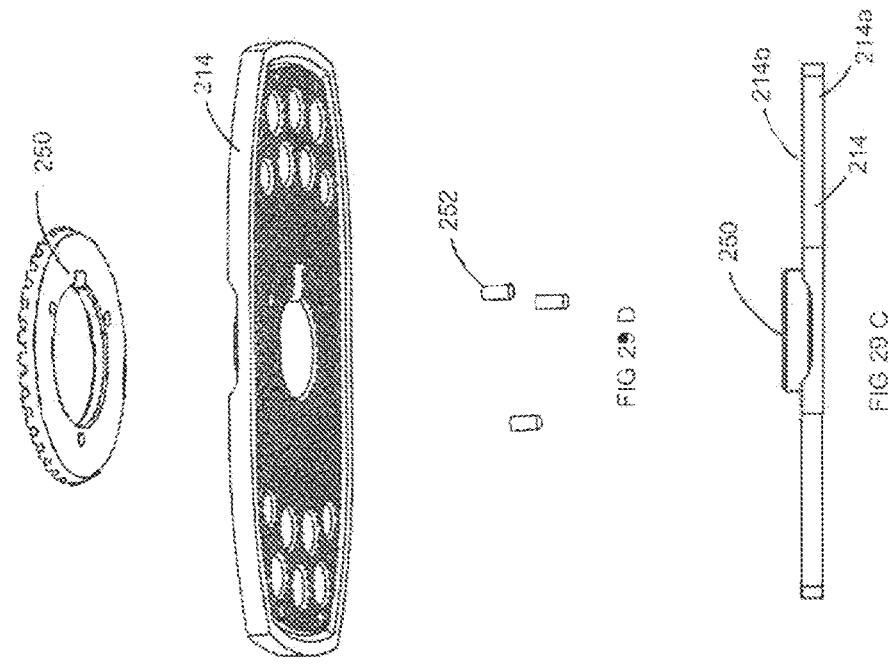
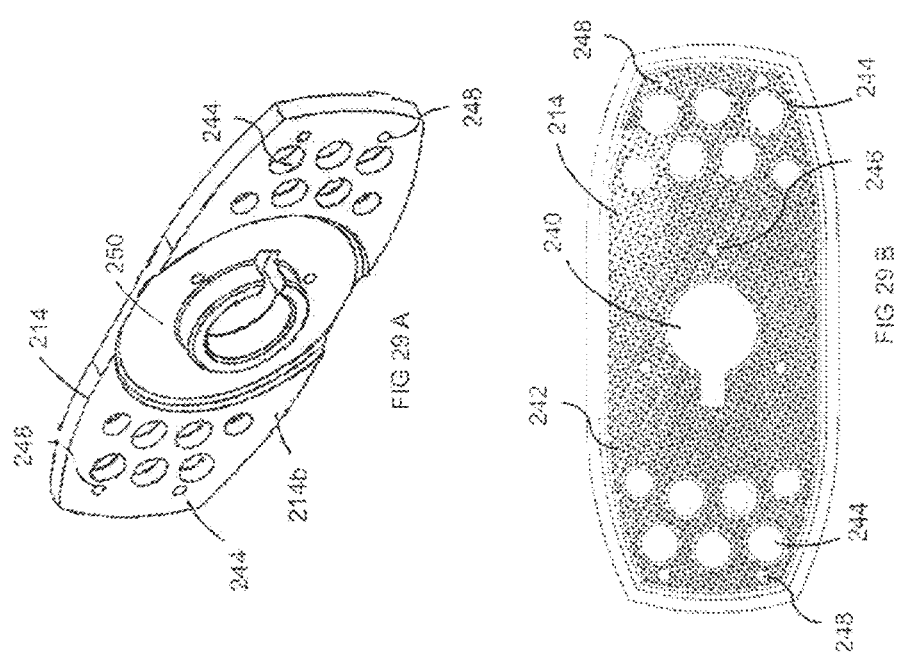

section A-A

295

290

293

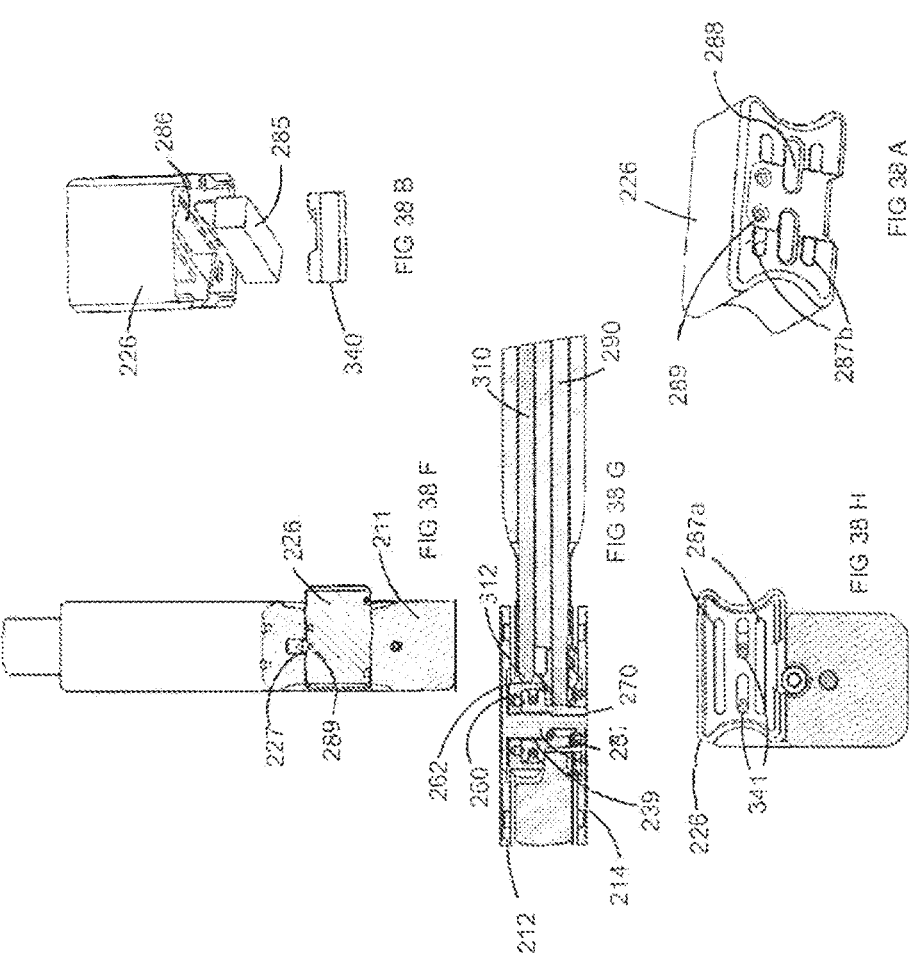
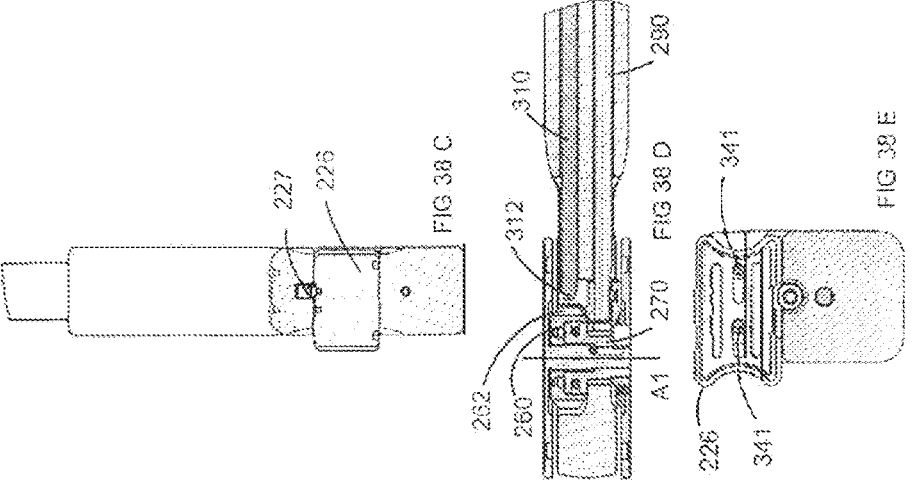

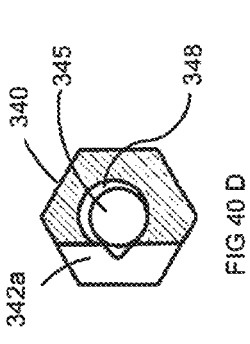
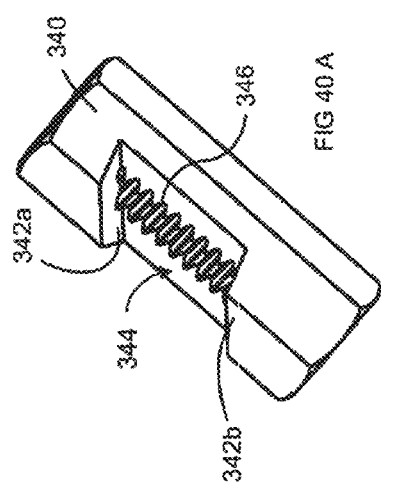
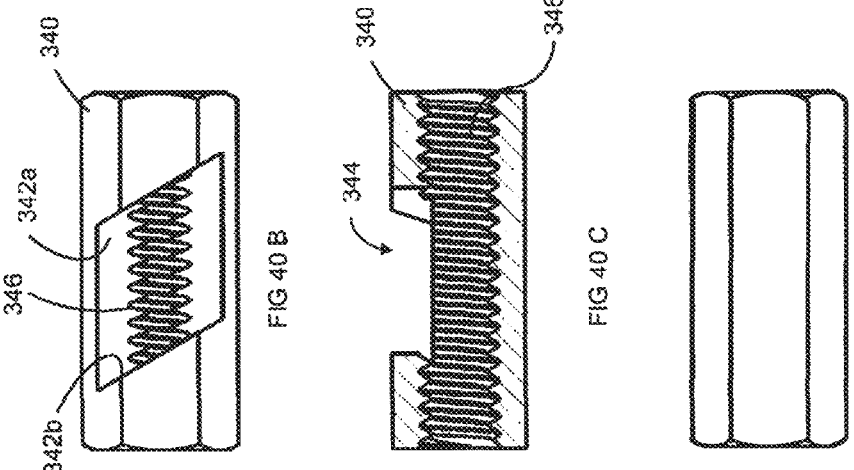

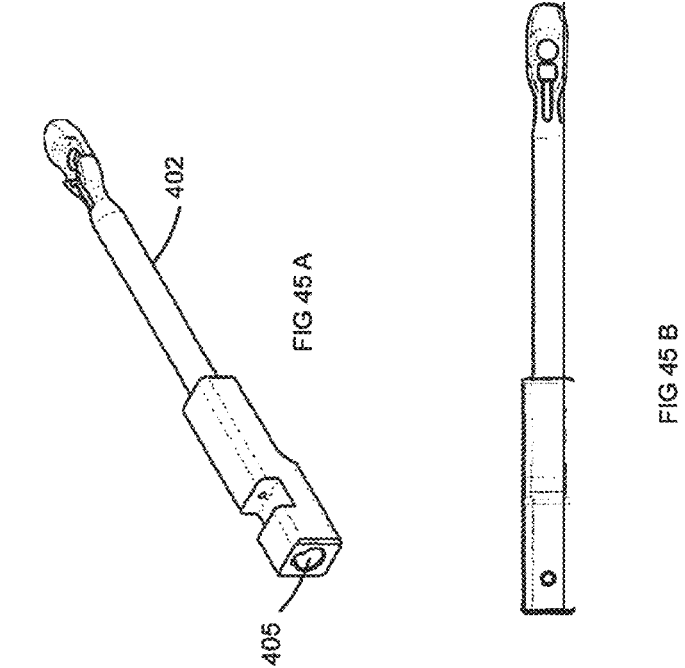
402
405
FIG 45 A
FIG 45 B
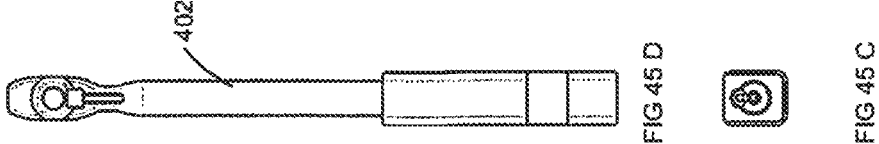
402
FIG 45 D
FIG 45 C

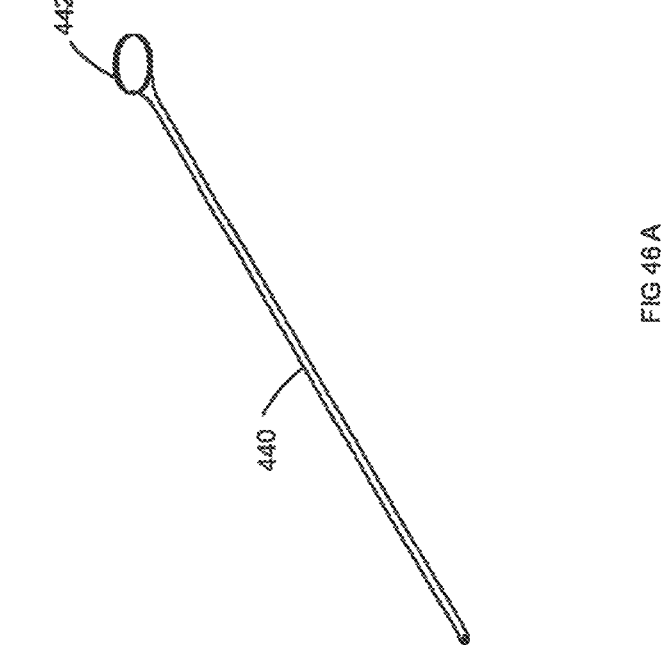
FIG 46 A
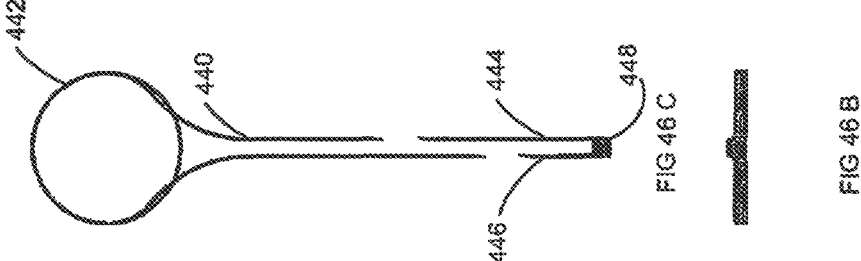
FIG 46 C
FIG 46 B

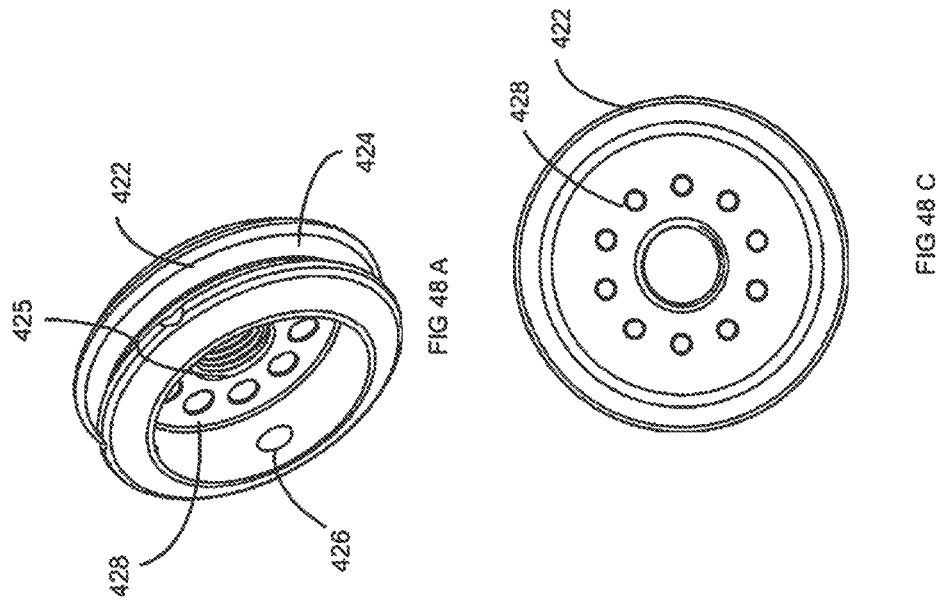
FIG 48 A
FIG 48 C
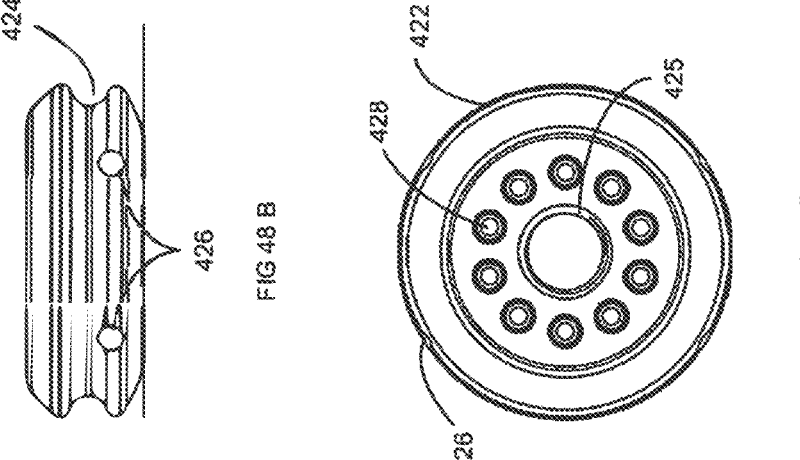
FIG 48 B
FIG 48 D

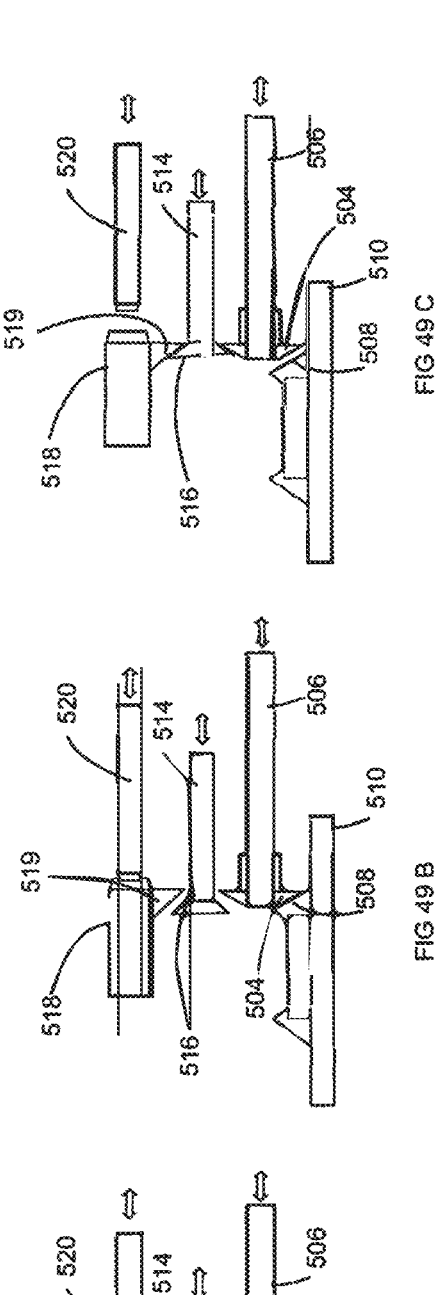
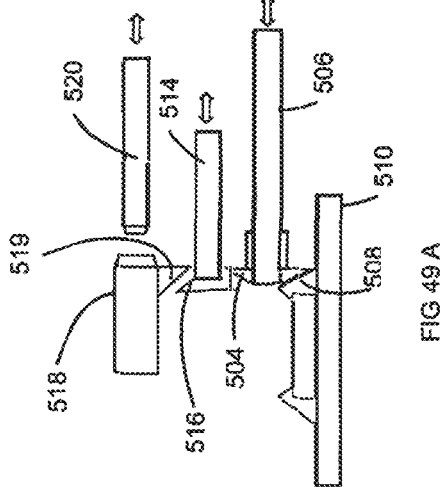
FIG 49 A
FIG 49 B
FIG 49 C

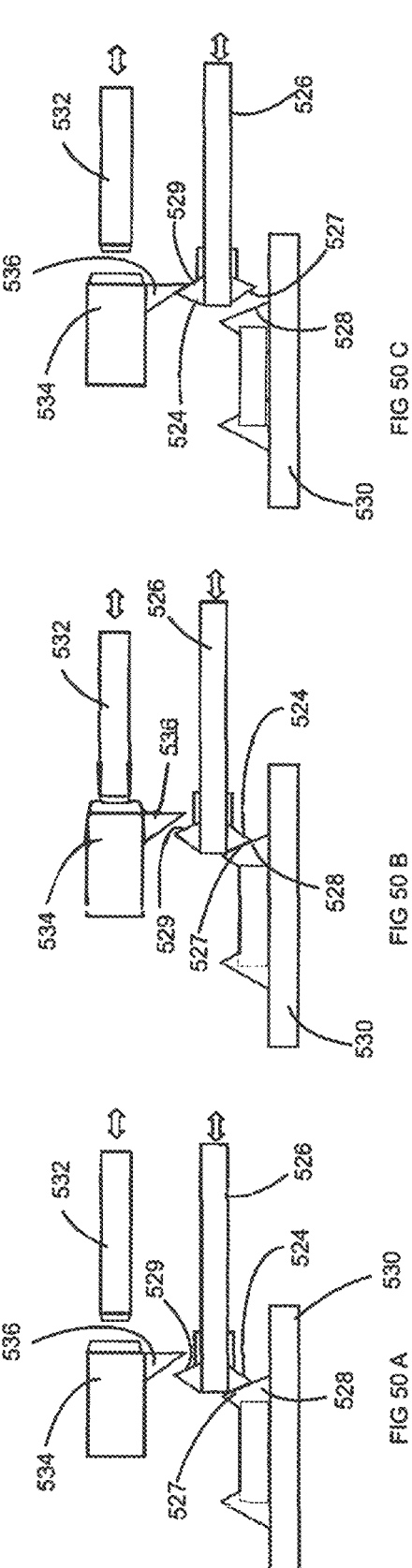

DISCECTOMY TOOL

BACKGROUND

This application claims priority from provisional application Ser. No. 62/961,277, filed Jan. 15, 2020, the entire contents of which are incorporated herein by reference.

TECHNICAL FIELD

This application relates to a discectomy tool, and more particularly to a discectomy tool with a rotatable head to clean the disc space.

BACKGROUND OF RELATED ART

Spinal fusion is one of the primary treatment options for a variety of spinal conditions due to various degenerative, neoplastic, traumatic and infections processes. In general, achieving spinal fusion requires bony growth between two or more adjacent spinal vertebrae. Spinal surgeons have a variety of surgical techniques to achieve this objective but in all cases the adjacent bones most be cleaned of any soft or non-bony tissues along the surfaces that oppose each other and bone or a synthetic alternative (implant) needs to be placed to bridge the gap between the surfaces. Placement of the bone or implant where the spinal disc is located (the interbody space) is a very common procedure known as interbody fusion. Among the challenges surgeons face during an interbody fusion is adequately cleaning out the existing disc material and cartilage so that the bone or implant will have appropriate contact with the bone of the adjacent vertebras. Failure to achieve adequate evacuation of the disc material increases the likelihood of an unsuccessful fusion (nonunion or pseudoarthrosis) and a poor clinical outcome, increasing the likelihood of the need for further surgery and incurring the associated costs, risks, discomfort and loss of patient productivity.

A number of tools have been developed over time to help adequately clean out the disc space. These include simple mechanical tools such as various size and shape scrapers (curettes, shavers, rasps) that attempt to remove disc via simple mechanical action. This requires significant manual work on the part of the surgeon, is time intensive, requires multiple passes of the instrument past the delicate neural structures in the spine and are fairly ineffective in reaching disc material outside the inline vector of the instruments. Other more sophisticated devices exist that use suction (Oroborus, J&J), drill tips (Midas rex) or multidirectional scrapers (orbit system from Benvenue) yet many of these are ineffective in generating adequate mechanical force to truly clean out the disc space, and are very costly and difficult for the surgeon to master, as well they can place the nerve tissue at risk.

The need exists for a rapid, more thorough and safer method to evacuate the spinal disc material in preparation for interbody fusion.

Additionally, for interbody fusion, first the disc space needs to be cleaned out with a material removal tool such as a scraper, shaver, etc. The material removal tool is then removed from the body and a separate delivery instrument is inserted into the disc space to deliver the implant into the disc space. This adds time and complications. It would be advantageous to expedite and facilitate this procedure.

SUMMARY OF THE INVENTION

The present invention overcomes the problems and deficiencies of the prior art. The present invention provides discectomy devices for more rapid, more thorough and safer method to evacuate the spinal disc material in preparation for interbody fusion.

The discectomy devices (tools) of the present invention in preferred embodiments include two shaver heads rotatable to scrape disc material off of the bone in 360 degrees creating a circular space, free of disc material, ideal for placement of bone or an implant for interbody fusion.

The discectomy devices (tools) of the present invention, in some embodiments, are expandable. Such expansion can be effected during rotation of the shaver heads or independent of rotation. The expansion effects relative movement between the shaver heads to increase their distance apart.

In some embodiments of the present invention, the shaver heads of the discectomy device can be separated (detached) from the shaft of the device and left in the patient's disc space to bridge the gap in the disc space and provide a structure for spinal fusion. Thus, they provide a dual function: a) clearing the disc space via rotation of the shaver heads; and b) placing an implant within the disc space in which bone graft can be placed for fusion.

In accordance with one aspect of the present invention, a discectomy device for clearing material out of a disc space of a patient is provided comprising a body, a first rotatable member at the distal portion of the body and a second rotatable member at the distal portion of the body spaced from the first rotatable member, wherein a transverse axis passes through the first and second rotatable members and is transverse to the longitudinal axis of the body. A first mechanism is actuable to rotate the first and second shaver heads about the transverse axis.

In some embodiments, the first and second rotatable members each have an outer surface and an inner surface and a distance between the inner surfaces of the rotatable members can be increased.

In some embodiments, the first and second rotatable members are retained in position parallel to one another during insertion and rotation. In some embodiments, the first and second rotatable members are retained in a parallel relationship during the increase of the distance therebetween.

In some embodiments, the first mechanism includes a first actuator, and the first actuator effects rotation of the first and second rotatable members about the transverse axis and effects movement of at least one of the first and second rotatable members to increase the distance between the first and second rotatable members.

In some embodiments, the first mechanism includes an elongated member having a proximal portion and a distal portion, the elongated member positioned within the body and rotatable to actuate a gear mechanism for rotating the first and second rotatable members. The gear mechanism can include in some embodiments a first gear attached to the elongated member and a second gear attached to one or both of the first rotatable member and second rotatable member.

In some embodiments, a locking or engagement member in the form of a slidable member is movable between an engaged and a disengaged position, wherein in an engaged position, the distance between the first and second rotatable members can be increased and in a disengaged position the distance between the first and second rotatable members cannot be changed. In some embodiments, one or both of the first and second rotatable members are moved along the transverse axis to increase the distance between the first and second rotatable members, and the first and second rotatable members are maintained in a substantially parallel position during such movement along the transverse axis.

In some embodiments, the first and second rotatable members are separable from the body of the discectomy tool to leave the first and second rotatable members behind the disc space of the patient. The first and second rotatable members can have a series of openings formed therein to receive graft material.

In some embodiments, the discectomy tool comprises a cover over the first and second rotatable members for insertion and an actuator to open the cover to expose the first and second rotatable members.

In accordance with another aspect of the present invention, a discectomy device for clearing material from a disc space of a patient is provided comprising a body, a first rotatable member at the distal portion of the body having a first surface and a second surface and a second rotatable member at the distal portion of the body. The second rotatable member is spaced from the first rotatable member and has a first surface and a second surface, the second surface of the second rotatable member facing the second surface of the first rotatable member. The first and second rotatable members are rotatable to clear disc material. The distance between the first and second rotatable members is alterable to change the distance between the first surfaces of the rotatable members.

In some embodiments, the first and second rotatable members are separable from the body of the tool and left behind in the disc space of the patient.

In some embodiments, one or both of the first and second rotatable members are moved along the transverse axis, which is perpendicular to the longitudinal axis of the body of the device, to increase the distance between the first and second rotatable members, and the first and second rotatable members are maintained in a substantially parallel position during such movement along the transverse axis.

In some embodiments, an expansion control member is movable between an engaged and a disengaged position wherein in an engaged position, the distance between the first and second rotatable members can be increased and in a disengaged position, the distance between the first and second rotatable members cannot be changed.

In some embodiments, the discectomy tool includes an actuator actuable to adjust the distance of the first and second rotatable members and to effect rotation of the first and second rotatable members. Such distance change, in some embodiments, occurs simultaneously with such rotation.

In accordance with another aspect of the present invention, a discectomy device for clearing material from a disc space of a patient is provided, the device comprising a body, a first rotatable member at the distal portion and a second rotatable member at the distal portion spaced from the first rotatable member, wherein the first and second rotatable members are configured to rotate to clear material from the disc space. An actuator is actuable to rotate the first and second rotatable members. The first and second members are detachably connected to the body of the discectomy tool for release from the body and placement within the disc space.

In some embodiments, the first and second rotatable members have a series of openings formed therein to receive graft material.

The various embodiments of the discectomy tool disclosed herein can be provided with structure/features to enable detachment of the rotatable members/shaver heads.

In accordance with another aspect of the present invention, the first and second rotatable members can be expanded without the rotatable members being rotated. Thus, in these embodiments, expansion is independent of rotation. This differs from the simultaneous rotation and expansion of other embodiments.

BRIEF DESCRIPTION OF THE DRAWINGS

Preferred embodiment(s) of the present disclosure are described herein with reference to the drawings wherein:

FIG. 1A is a perspective view of the discectomy tool (device) in accordance with one embodiment of the present invention;

FIG. 1B is a side view of the discectomy tool of FIG. 1A;

FIG. 1C is an exploded view of the discectomy tool of FIG. 1A;

FIG. 1D is a front cutaway view of the handle to illustrate the internal gear;

FIG. 2A is longitudinal cross-sectional view of the discectomy tool of FIG. 1A taken along line A-A of FIG. 1D;

FIG. 2B is an enlarged view of the area of detail "A" identified in FIG. 2B;

FIG. 2C is a longitudinal cross-sectional view of the discectomy tool of FIG. 1A taken along line B-B of FIG. 1D;

FIG. 2D is an enlarged view of the area of detail "B" identified in FIG. 2C;

FIGS. 3A and 3B are side views (from different orientations) of the shaft (drive rod) of the discectomy tool of FIG. 1A;

FIG. 3C is a front view of the gear of the shaft of FIG. 3A;

FIGS. 4A-4D illustrate the top (upper) shaver head of the discectomy tool of FIG. 1A wherein FIG. 4A is a bottom perspective view of the shaver head;

FIG. 4B is a bottom view of the shaver head;

FIG. 4C is side view of the shaver head; and

FIG. 4D is a top view of the shaver head;

FIGS. 5A-5D illustrate one of the bottom (lower) shaver head of the discectomy tool of FIG. 1A wherein FIG. 5A is a perspective view of the shaver head;

FIG. 5B is a bottom view of the shaver head;

FIG. 5C is side view of the shaver head; and

FIG. 5D is a top view of the shaver head;

FIGS. 6A-6D illustrate an alternate embodiment of the discectomy tool of the present invention having a shaver detachable from the delivery shaft for use as an interbody implant wherein FIG. 6A is a perspective view of the shaver head in the attached (engaged) position with the claws in the engaged position;

FIG. 6B is a bottom view of the top shaver head in the attached position of FIG. 6A;

FIG. 6C is a perspective view of the shaver head in the release position with the claws in the disengaged position;

FIG. 6D is a bottom view of top the shaver head in the release position of FIG. 6C;

FIG. 7 is a perspective view of an alternate embodiment of the claw mechanism for engaging and releasing the shaver head, the claws shown in the disengaged position;

FIG. 8 is a top view of an alternate embodiment of a device for engaging and releasing the shaver head, the device having a cam actuation device, the grippers shown in the disengaged position;

FIG. 9 is a top view of an alternate embodiment of a device for engaging and releasing the shaver head, the device having a screw actuation mechanism, the engaging surfaces shown in the disengaged position;

FIG. 10 is a bottom view of the top shaver head an alternate embodiment of a device for engaging and releasing the shaver head, the device having a screw actuation mechanism, and the engaging surfaces shown in the disengaged position;

FIG. 18 is an enlarged perspective view of the shaver head of FIG. 17;

FIG. 19 is a cutaway view of the shaver head of FIG. 18;

FIG. 20 is a perspective view showing an actuation mechanism engageable with the expansion mechanism of FIG. 17 to expand the shaver heads;

FIG. 21A is an exploded view of an alternate embodiment of the discectomy tool of the present invention having an expandable shaver head to increase the distance between the rotatable upper and lower shaver heads;

FIG. 21B is a perspective view of the body of the discectomy tool of FIG. 21A;

FIG. 21C is a bottom view of the discectomy tool of FIG. 21A;

FIG. 21D is a top view of the discectomy tool of FIG. 21A;

FIG. 21E is a rear view of the discectomy tool of FIG. 21A;

FIG. 22A is top view of the upper shaver head of FIG. 21A;

FIG. 22B is bottom view of the lower shaver head of FIG. 21A;

FIG. 25 is a top view of the discectomy tool of FIG. 24A;

FIG. 27A is a cross-sectional view of an alternate embodiment of the discectomy tool of the present invention having an expandable shaver head detachable from the drive shaft;

FIG. 27B is an enlarged cross-sectional view of the area of detail A of FIG. 27A showing the drive shaft in the advanced position to connect the shaver head;

FIG. 27C is an enlarged cross-sectional view similar to FIG. 27B showing the drive shaft in the withdrawn (retracted) position to disconnect the shaver head;

FIG. 28 is a side view of the drive shaft of FIG. 27A;

FIG. 28A is a perspective view of the shaver sleeve of the discectomy tool of FIG. 27A;

FIG. 28B is a side view of the sleeve of FIG. 28A;

FIGS. 29A-29D illustrate the bottom shaver head of the discectomy tool of FIG. 23 wherein FIG. 29A is a top perspective view of the shaver head;

FIG. 29B is a bottom view of the shaver head;

FIG. 29C is side view of the shaver; and

FIG. 29D is an exploded view of the shaver head;

FIGS. 30A-31 illustrate the top shaver assembly of the discectomy tool of FIG. 23 wherein FIG. 30A is a top view of the shaver head;

FIG. 30B is a cross-sectional view of the shaver assembly taken along line A-A of FIG. 30A;

FIG. 30C is an exploded view of the shaver assembly; and

FIG. 31 is a perspective view of the shaver assembly;

FIGS. 32A-32C illustrate the rotation hub of the discectomy tool of FIG. 23 wherein FIG. 32A is a perspective view of the hub;

FIG. 32B is a front view of the hub; and

FIG. 32C is a side view of the hub;

FIGS. 34A-34C illustrate the pinion gear of the discectomy tool of FIG. 23 for rotation of the shaver head wherein FIG. 34A is a perspective view of the gear;

FIG. 34B is a side view of the gear; and

FIG. 34C is another side view of the gear;

FIGS. 34D-34F illustrate the gear of the discectomy tool of FIG. 23 (which interacts with the pinion gear of FIG. 34A) for rotation of the shaver head wherein FIG. 34D is a perspective view of the gear;

FIG. 34E is a top view of the gear; and

FIG. 34F is side view of the gear;

FIGS. 35A-35C illustrate the sprocket hub of FIG. 30C wherein

FIG. 35A is a perspective view of the hub;

FIG. 35B is a front view of the hub; and

FIG. 35C is top view of the hub;

FIGS. 37A-37D illustrate the sprocket of FIG. 30C wherein

FIG. 37A is a perspective view of the sprocket;

FIG. 37B is a top view of the sprocket;

FIG. 37C is a bottom view of the sprocket; and

FIG. 37D is a top view of the sprocket;

FIG. 38A is perspective view of the slider of FIG. 23;

FIG. 38B is an exploded view of the slider assembly of FIG. 23;

FIG. 38C is a cross-sectional view showing the slider of FIG. 23 in the disengaged position for non-expansion of the shaver heads;

FIG. 38D is a longitudinal cross-sectional view showing the expander rod in the non-engaged position corresponding to the position of the slider in FIG. 38C;

FIG. 38E is a rear view showing the slider in the position of FIG. 38C;

FIG. 38F is a cross-sectional view showing the slider in the engaged position to enable expansion of the shaver heads;

FIG. 38G is a longitudinal cross-sectional view showing the expander rod in the engaged position corresponding to the position of the slider in FIG. 38F;

FIG. 38H is a rear view showing the slider in the position of FIG. 38E;

FIGS. 40A-40D illustrate the standoff of FIG. 24B wherein FIG. 40A is a perspective view of the standoff;

FIG. 40B is a top view of the standoff;

FIG. 40C is a side view of the standoff; and

FIG. 40D is a cross-sectional view of the standoff;

FIGS. 42A-42F illustrate an alternate embodiment of the shaver head region of the discectomy tool of the present invention having a cover for the upper and lower shaver heads wherein FIG. 42A is top view of the upper shaver head with the cover enclosing the shaver head for insertion of the discectomy tool;

FIG. 42B is front view showing the cover in the position of FIG. 42A;

FIG. 42C is top view similar to FIG. 42A showing the cover partially opened;

FIG. 42D is a front view showing the cover in the position of FIG. 42C;

FIG. 42E is top view similar to FIG. 42C showing the cover fully open;

FIG. 42F is a front view showing the cover in the position of FIG. 42E;

FIG. 45A is a perspective view of the body of the discectomy tool of FIG. 43;

FIG. 45B is a bottom view of the body of the discectomy tool of FIG. 45A FIG. 45C is a rear view of the body of the discectomy tool of FIG. 45A;

FIG. 45D is a top view of the body of discectomy tool of FIG. 45A;

FIGS. 46A-46C illustrate the cable of FIG. 44 wherein FIG. 46A is a perspective view of the cable;

FIG. 46B is a front view of the cable; and

FIG. 46C is a top view of the cable;

FIGS. 48A-48D illustrate the sprocket of FIG. 44 wherein FIG. 48A is a perspective view of the sprocket;

FIG. 48B is a side view of the sprocket;

FIG. 48C is a bottom view of the sprocket; and

FIG. 48D is a top view of the sprocket;

Figure 52:
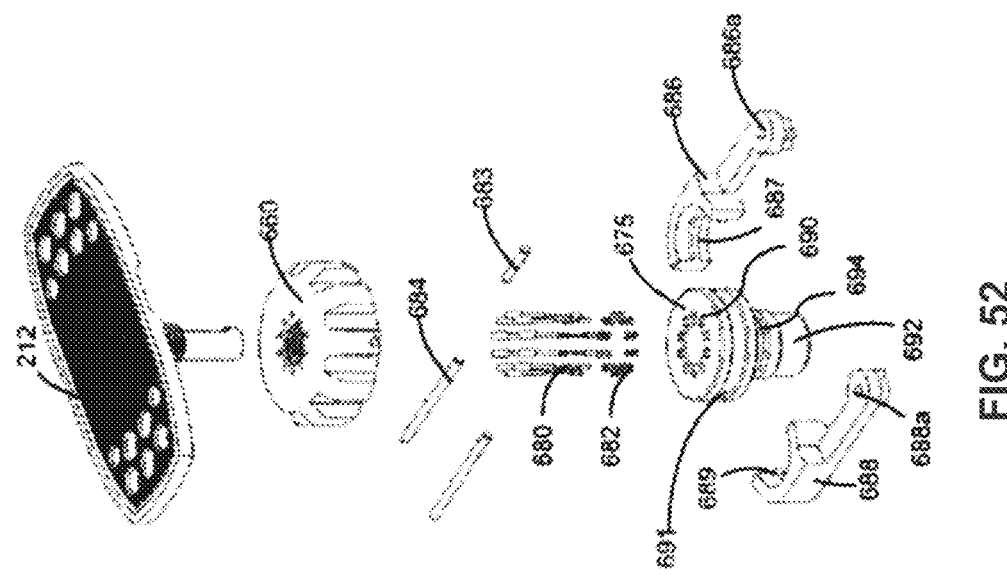
Figure 51:
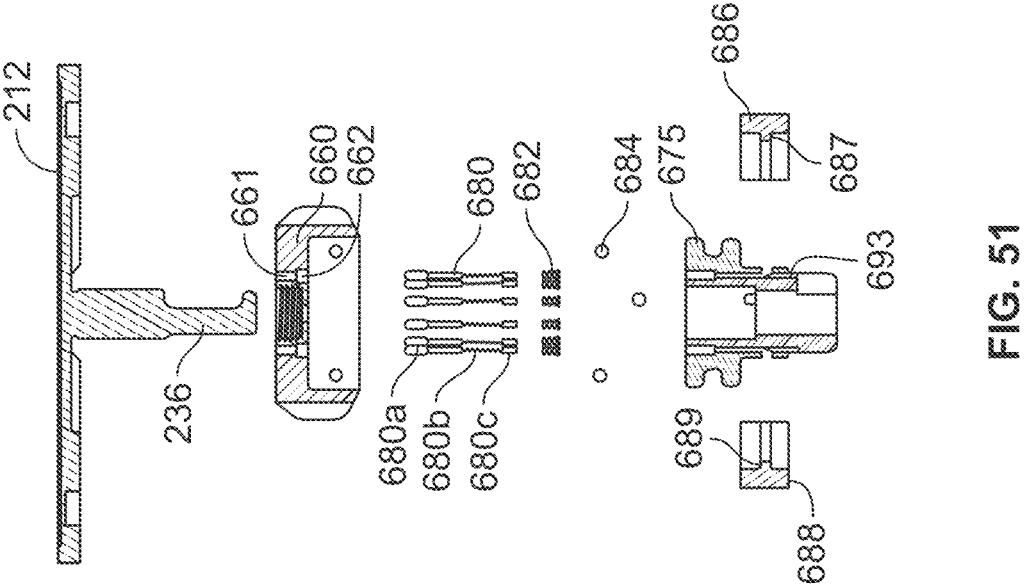
Figures 53, 54:
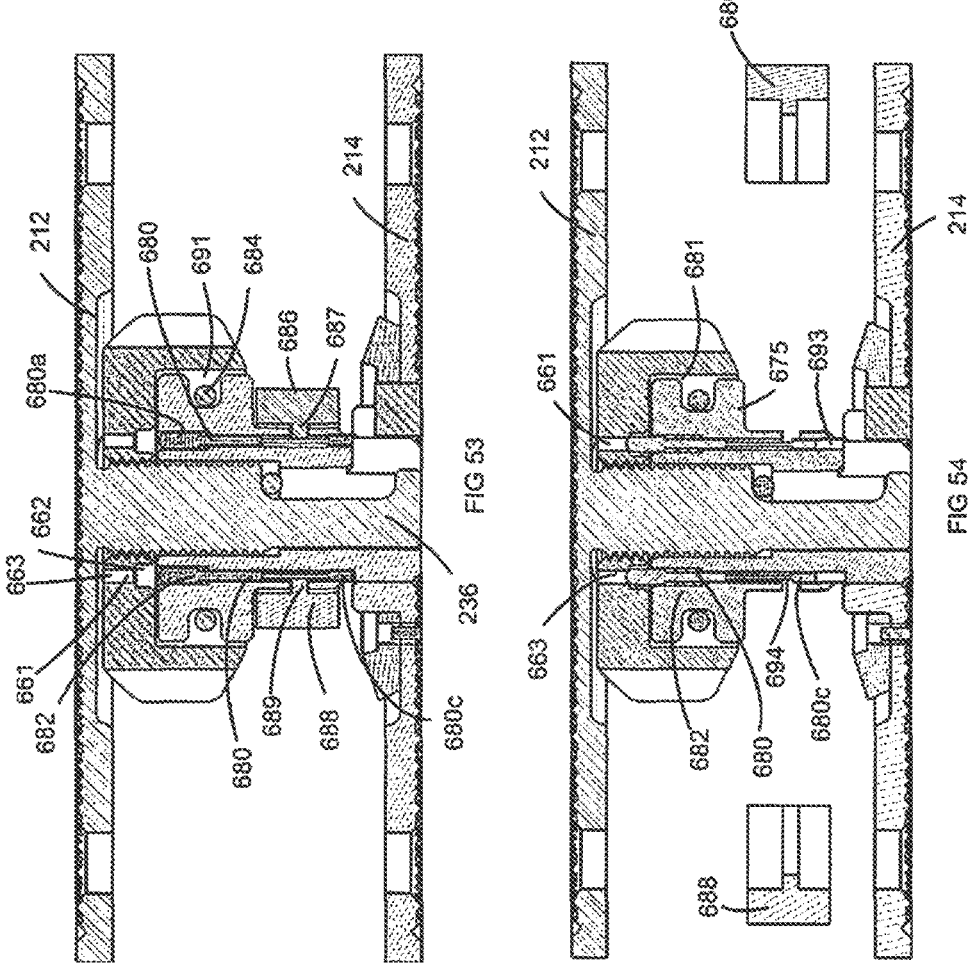

FIGS. 49A-49C are schematic views illustrating an alternate embodiment of the discectomy tool of the present invention which provides for independent shaver head rotation and expansion wherein FIG. 49A illustrates the position of the components for rotation without expansion, FIG. 49B illustrates the position of the components for rotation and expansion, and FIG. 49C illustrates the position of the components during expansion without rotation;

FIGS. 50A-50C are schematic views illustrating another alternate embodiment of the discectomy tool of the present invention which allows for independent shaver head rotation and expansion wherein FIG. 50A illustrates the position of the components for rotation without expansion, FIG. 50B illustrates the position of the components for rotation and expansion, and FIG. 50C illustrates the position of the components during expansion without rotation;

FIGS. 51 and 52 are exploded views of the shaver head assembly of an alternate embodiment of the discectomy tool of the present invention having a release mechanism to separate the upper and lower shaver heads from the tool;

FIG. 53 is a cross-sectional view of the shaver head assembly of FIGS. 51 and 52 shown in the engaged position; and FIG. 54 is a cross-sectional view of the shaver head assembly of FIGS. 51 and 52 shown in the engaged position.

DETAILED DESCRIPTION OF PREFERRED EMBODIMENTS

The devices of the present invention, also referred to herein as discectomy instruments or discectomy tools or discectomy devices, provide a rapid, more thorough and safer method to evacuate the spinal disc material of a patient in preparation for interbody fusion. The devices in preferred embodiments utilize a gear mechanism to rotate the distal head (shaver heads) to remove disc material wherein the distal head rotates about an axis transverse to a longitudinal axis of the device. This is described in more detail below.

The discectomy device of the present invention in preferred embodiments includes two rotatable shaver heads— an upper and lower shaver head. The instrument is inserted into the disc space, and the distal shaver heads are rotated to scrape disc material off of the bone in 360 degrees creating a circular space, free of disc material, ideal for placement of bone or an implant for interbody fusion. The discectomy device can advantageously be inserted a single time, eliminating the need to repeatedly pass the device past the delicate nerves of the spine. The device can also generate significant mechanical force to gain adequate friction to remove the disc material from the bone, enabling it to clear disc material in 360 degrees, thus evacuating the disc space rapidly, saving surgical time and minimizing the risk of prolonged anesthesia.

In some embodiments of the present invention, the discectomy device is expandable. In such embodiments, the discectomy device is placed into the disc space, and the shaver heads are expanded, i.e., separated (moved away from each other), to improve endplate apposition. The shaver heads in preferred embodiments can be moved apart along the transverse axis about which they rotate for expansion. The extent of expansion in preferred embodiments can be controlled by the user. The extent of expansion can also be dependent on the size of the disc space. Once the shaver heads are separated to the desired spacing, the shaver heads are rotated to scrape disc material off of the bone in 360 degrees creating a circular space, free of disc material, ideal for placement of bone or an implant for interbody fusion. In some embodiments, the shaver heads can be expanded during their rotation. Mechanisms to achieve shaver head expansion are discussed in detail below.

In some embodiments of the present invention, the shaver heads of the discectomy device can be separated (detached) from the shaft of the device and left in the disc space to provide a structure for spinal fusion. Such separable shaver heads can be provided with the non-expandable head and the expandable head embodiments of the present invention. More specifically, in the versions of the device with separable shaver heads, once the disc material is evacuated, the surgeon, if desired, can rotate the detachable head into a desired position within the disc space and then detach the head, leaving it behind in the disc space. That is, the detached/deployed head is disengaged from the device shaft to serve as a structural support within the disc space around and which bone graft can be placed for fusion, effectively converting it into a permanent implant or an interbody cage/fusion device. This has numerous advantages: i) it saves a significant amount of time by eliminating the need to prepare and place a separate implant; ii) it permits placement of the implant at any angle the surgeon desires to maximize sagittal balance, height restoration potentially minimizing graft expulsion; iii) it avoids the need to pass a large implant past the neighboring spinal nerves and/or iv) it avoids the need for multiple additional instruments needed to prepare the disc space and place the implant which reduces the burden on facility sterile processing departments.

To aid insertion, in some embodiments, a cover is provided for the shaver head which is removable or openable once the shaver heads are in the desired position within the disc space. This is discussed in detail below.

As will appreciated from the discussion below, in summary, there are four versions of the devices of the present invention: 1) a rotatable shaver head which is non expandable and non-detachable; 2) a rotatable shaver head which is detachable but not expandable; 3) a rotatable shaver head which is expandable but non-detachable; and 4) a rotatable shaver head which is both expandable and detachable. Each of these versions is discussed in detail below. Additionally, there are several embodiments of each of the four versions, including different mechanisms to effect rotation, expansion and detachment, which are also discussed in detail below.

Referring now to the drawings and particular embodiments of the present disclosure, wherein like reference numerals identify similar structural features of the devices disclosed herein, there are illustrated several embodiments of the surgical instruments. In these instruments, the term "distal" refers to the region or portion further from the user and the term "proximal" refers to the region closer to the user. As used herein, the term "substantially" means±25% of a given value or measurement.

Turning first to the embodiment of FIGS. 1-5D, the discectomy instrument (also referred to herein as a discectomy device or tool) is designated generally by reference numeral 10 and includes a proximal portion 12 having a handle 14 and a distal portion 16 having a pair of rotatable members in the form of shaver heads 18a, 18b (collectively referred to as shaver head 18). In the orientation of the illustrated embodiment, the shaver head 18a forms a top or upper shaver head and the shaver head 18b forms a bottom or lower shaver head. However, it should be appreciated, that the designations of top, upper, bottom and lower, in this embodiment as well as in the other embodiments disclosed herein, correspond to the orientation in the Figures-if the orientation of the instrument changes, the orientation of the shaver heads 18a, 18b will change accordingly. Thus, the shaver heads are also identified herein throughout the various embodiments as a first shaver head (or first rotatable member) and a second shaver head (or second rotatable member). The shaver heads are also referred to herein as "shavers".

Extending from handle 14 is cylindrical outer delivery tube or elongated body 22. Positioned within the outer tube 22, concentrically in the illustrated embodiment, is shaft 24 which rotates within outer tube 22 to effect rotation of the shaver head 18. Shaft 24 terminates in a pinion gear 25 at its distal end for engagement with the ring gear of one of the shaver heads for effecting shaver head rotation as described below.

Upper shaver head 18a has a first or upper (outer) surface 26 and an opening 28 to receive an attachment screw 30 (see FIGS. 4A-4D). Outer surface 26 is the surface which contacts the disc material and can include openings for graft material. Extending from its second or lower (inner) surface 32 is a circular (or other shaped) receiver or strut 34 with an opening 36, aligned with opening 28, for attachment to the lower shaver 18b. Teeth 33 of gear 31 are provided adjacent lower surface 32, preferably extending around 360 degrees as shown.

Lower shaver head 18b (see FIGS. 5A-5B) has a first or upper (inner) surface 40 facing lower surface 32 of upper shaver head 18a. Extending from its upper surface 40 is a rectangular post 46 with an opening 45 to receive attachment screw 30 for attachment to the upper shaver 18b. The second or lower (outer) surface 44 has an opening 48 aligned with opening 45. Outer surface 44 is the surface which contacts the disc material and can include openings for graft material. The receiver 34 of the upper shaver 18a forms a female receptacle to receive the male post 46 of the lower shaver 18b. The screw 30 holds the two shaver heads 18a, 18b together. Other shapes for the mount and other ways to connect the two shaver heads 18a, 18b are also contemplated. Also note the female receptacle and male post can alternatively be reversed so the female receptacle is provided on the lower shaver head 18b and the male post is provided on the upper shaver head. In any case, the shaver heads 18a, 18b are secured together so they rotate together as a unit.

The shaver heads 18a, 18b rotate together about axis Y (FIG. 1B) which is transverse to the longitudinal axis X of the instrument 10 and shaft 24 (and outer tube 22). On the upper shaver head 18a, extending from its lower surface 44, is a gear 31 having a plurality of teeth 33 arranged circumferentially which intermesh with the teeth 27 of gear 25 at the distal end of shaft 24. In this manner, when shaft 24 is rotated about its longitudinal axis X, attached gear 25 also rotates about the longitudinal axis X in the same direction. This causes gear 31 of shaver head 18a to rotate about axis Y. Since shaver head 18b is attached to shaver head 18a, such rotation of shaver head 18a effects rotation of shaver head 18b so the shaver heads 18a, 18b together rotate in a circular motion. The intermeshing of the gears 31 and 25 can be appreciated in the top view of FIG. 6B, which although directed to a different embodiment as described below, has the same gear mechanism (although labeled as gears 55, 57) to effect rotation of the shaver head about axis Y. Stated another way, the shaver heads 18a, 18b rotate in a plane parallel to the longitudinal axis X of the rotating shaft 24. Note although the gear/teeth are shown on the upper shaver head 18a, it is also contemplated that the gear/teeth can be located on the lower shaver head 18b instead. In either case, since the shaver heads 18a, 18b are attached, the intermeshing of the teeth of the shaver head gear with the gear 25 of shaft 24, rotates the shaver heads 18a, 18b about an axis transverse to the longitudinal axis of the instrument 10. Such rotation causes the shaver heads 18a, 18b to scrape disc material off of the bone in 360 degrees creating a circular space, free of disc material, for subsequent placement of bone or an implant for interbody fusion.

Mounting of the handle 14 to the inner shaft 24 is best shown in FIGS. 2C and 2D. Handle 14 has a threaded bore 15, extending transverse to the longitudinal axis, to receive screw 17. Screw 17 extends transverse to the shaft 24 and contacts flat or recessed surface 24a of shaft 24 (FIG. 3B). When handle 14 is grasped and manually rotated by the user, the attached shaft 24 likewise rotates within outer tube 22 in the same direction as the handle 14 about its longitudinal axis. This causes rotation of the shaver head 18 due to the gear mechanism as described above.

In the embodiment of FIGS. 1A-SD, the shaver heads 18a, 18b are permanently affixed (attached) to the shaft 24 such that after cleaning the disc space, the instrument 10 is removed so bone implant or a device, e.g., a cage or other structure, for receiving implant material can be inserted into the cleaned disc space. In the alternate embodiment of FIGS. 6A-6D, the shaver heads 18a, 18b, after cleaning the disc space, are separated from the shaft so they can be left in the body to form a structural support to maintain the intervertebral space for placement of implant material within the disc space. This advantageously not only reduces the time of the procedure but reduces surgical complications by eliminating the need to insert another instrument after removal of the discectomy tool. It also reduces instrument costs since disc material removal and disc space implantation are achieved in a single instrument.

Turning now to FIGS. 6A-6D, which provide an example of a detachable shaver head, the instrument is designated generally by reference numeral 50 and has the same shaver head as the instrument 10 of FIG. 1A (Note only the distal portion of the instrument is shown). Instrument 50 also has the same gear mechanism for effecting shaver head rotation as instrument 10. Thus, upper and lower shaver heads 52a, 52b (collectively shaver head 52) are identical to upper and lower shaver heads 18a, 18b and the gear 54 of shaver head 52a and gear 55 of the instrument shaft are identical to gear 31 of shaver head 18a and gear 25 of instrument 10. Thus, rotation of the shaft of instrument 50, like shaft 24 of instrument 10, effects rotation of the shaver heads 52a, 52b to clean out the disc space in a circular (360 degree motion) as described above. Instrument 50 differs from instrument 10 in that it has a detachable mechanism for the shaver heads 52a, 52b. In all other respects, instrument 50 is the same as instrument 10 so the structure and function of instrument 10 and its components, as well as its variations, are fully applicable to instrument 50 so for brevity are not further discussed herein.

The detachability mechanism (also referred to herein as the release mechanism) includes a retention rod 60 which interacts with a pair of pivotable claws or jaws 62a, 62b which extend from a distal end of the outer tube. Rod 60 has a plurality of teeth 66 forming a toothed engagement section 68 forming a rack. Rod 60 is axially movable between an initial distal position wherein the claws 62a, 62b are in the engaged or holding (or locking) position and a proximal position wherein the claws 62a, 62b are in a disengaged or release (or unlocking) position. In the engaged position, the claws 62a, 62b are closed and engage the projecting receiver 67 (similar in structure to receiver 34) of shaver head 18a described above) of shaver head 62a. In preferred embodiments, the claws 62a, 62b are closed sufficiently to engage and hold the receiver 67 but apply less than a clamping force. This position is shown in FIG. 6A-6B. In the illustrated embodiment, the distal ends of the claws 62a, 62b are C-shaped (see ends 63a, 63b of FIG. 6B) and face each other forming a circular or a substantially circular enclosure. Other shapes are contemplated to provide a retention configuration for retention of the shaver head 52. Due to the attachment of the shaver heads 52a, 52b, retention of one of the shaver heads, e.g., shaver head 52a, is sufficient to hold both shaver heads 52a, 52b. Note in alternate embodiments, the claws 62a, 62b can instead engage the lower shaver head 52b and in other alternate embodiments engage both shaver heads 52a, 52b. In the disengaged position, the claws 62a, 62b are more open (spaced further apart) to disengage from the shaver head 52a to allow release thereof as shown in FIGS. 6C and 6D.

Figure 5B:
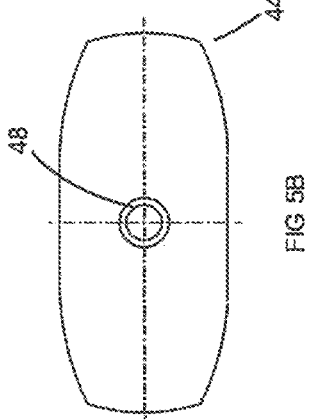
Figure 5D:
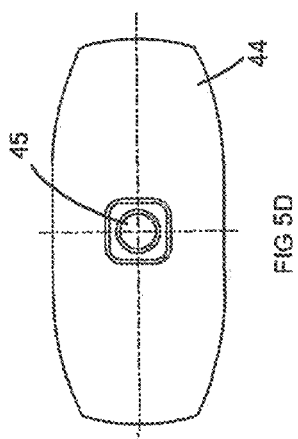
Figure 5A:
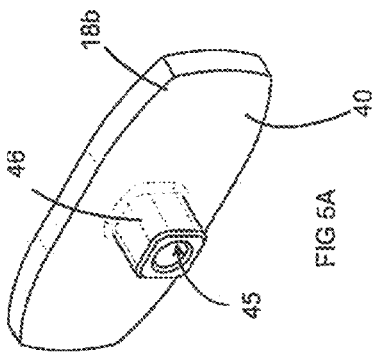
Figure 5C:
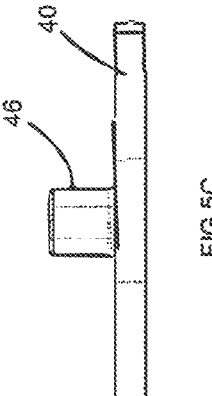
Figure 6E:
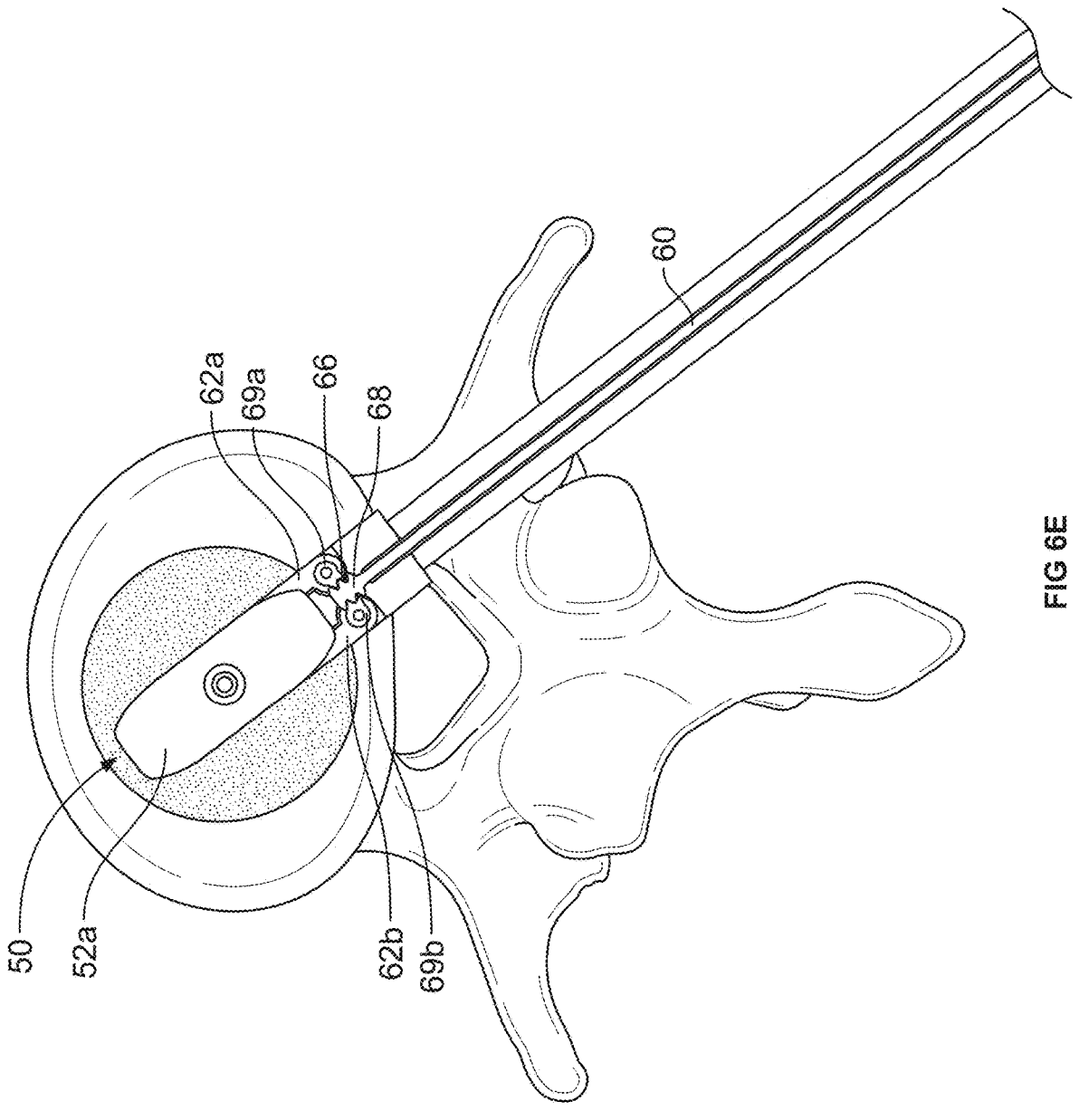
Figure 6F:
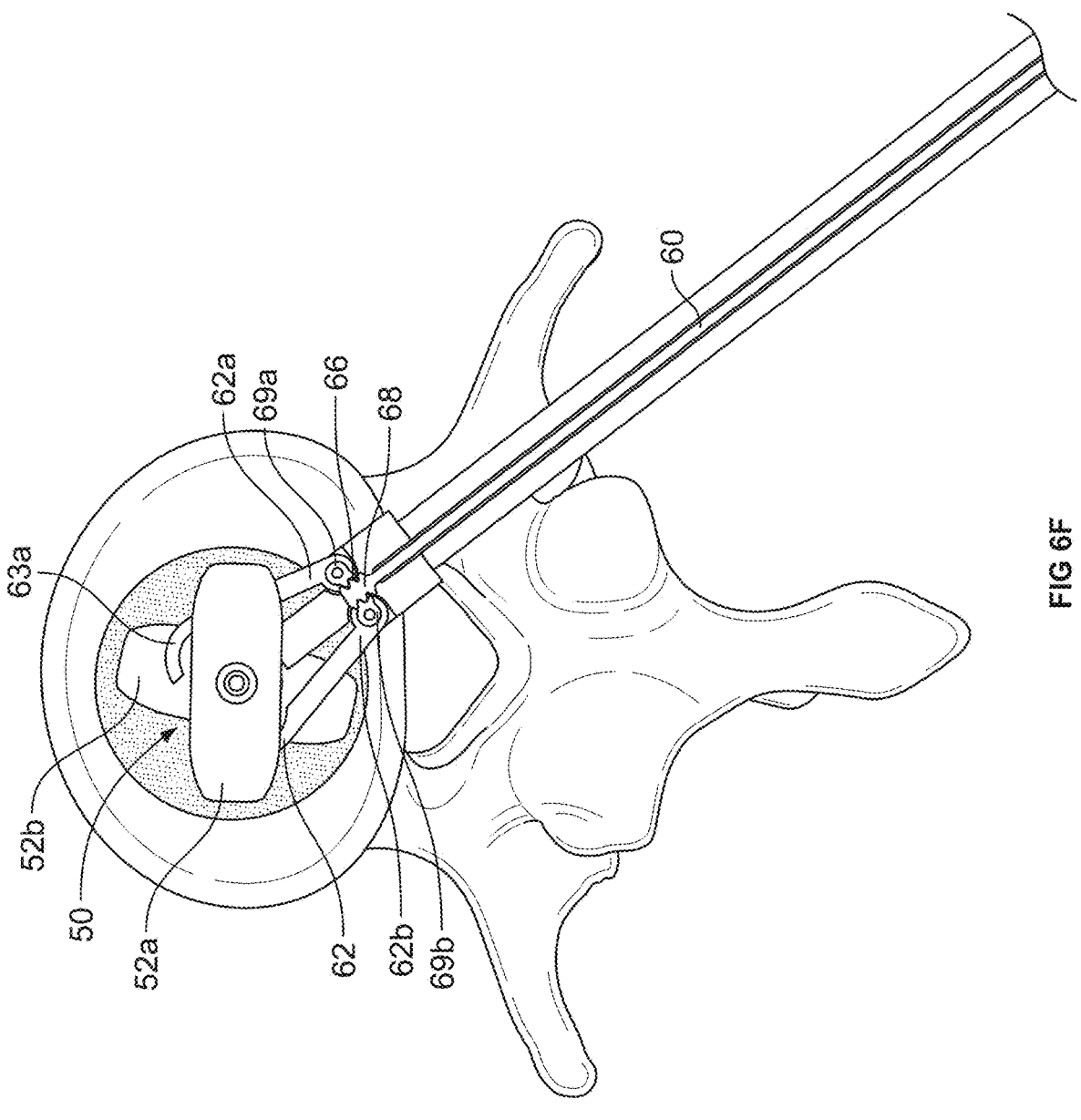
Figure 6G:
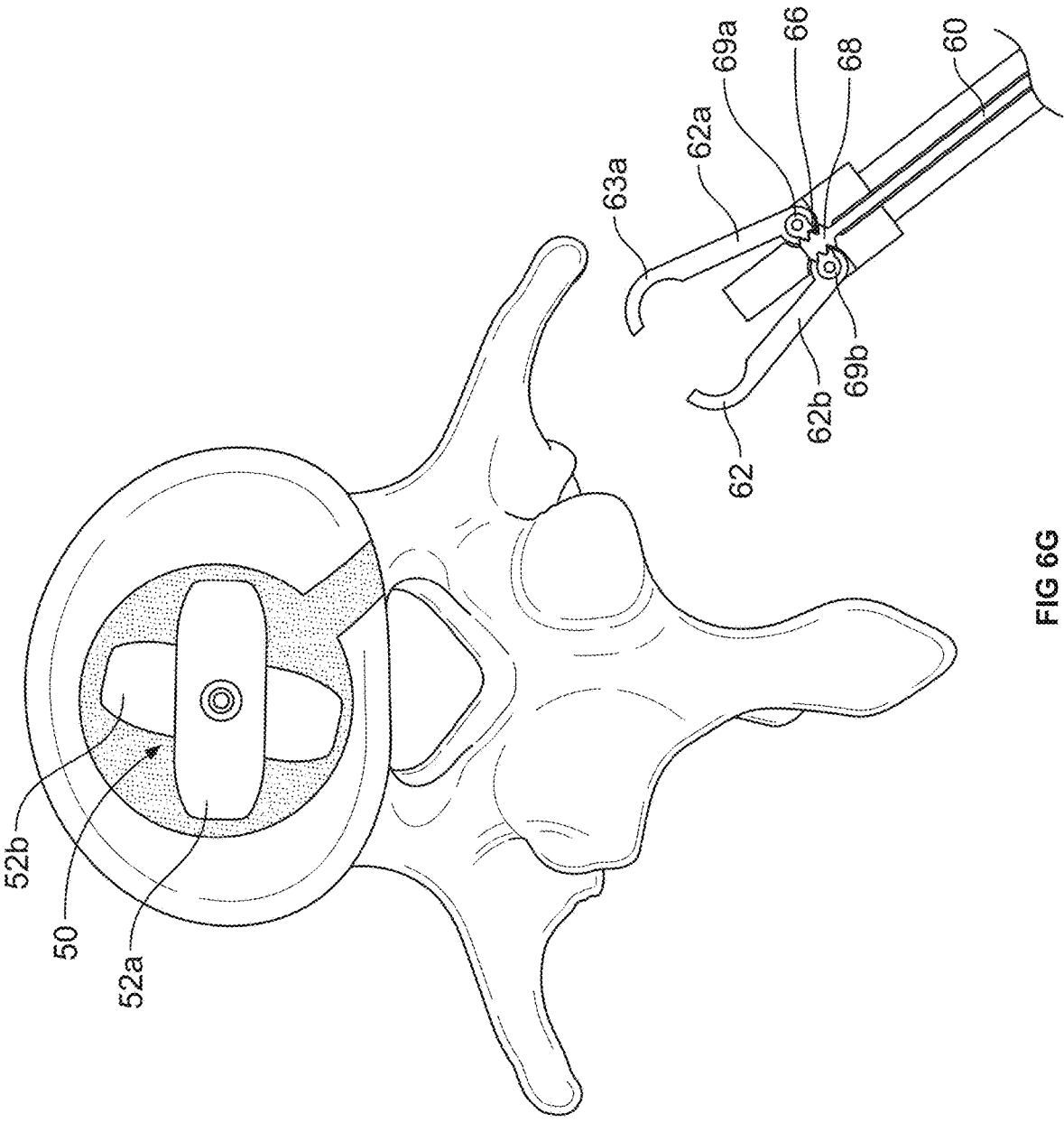

Referring to FIGS. 6E-6G, in use, the instrument 50 is inserted into the patient's body so the shaver head 52 is positioned within the disc space (FIG. 6E). The instrument handle (not shown), like handle 14 of instrument 10, is manually rotated as described above to rotate the shaft and shaver head 52 to clean out the disc space as the shaver heads 52a, 52b rotate in a 360 motion about an axis transverse to the longitudinal axis of the instrument 50 (FIG. 6F). After the disc material has been cleared, if the user desires to leave the shaver head 52 within the disc space as an intervertebral spacer, the shaver head 52 can be rotated to any desired position and then the user actuates rod 60 to move it axially distally. A lever or sliding mechanism or other actuator can be provided at the proximal end of the instrument 50 operatively connected to the rod 60 to effect axial movement of the rod 60. Axial movement of rod 60 to a distal (advanced) position (or in alternate embodiments movement to a proximal position) causes the claws 62a, 62b to move from their closed position of FIGS. 6A and 6B to their open position of FIGS. 6C and 6D, due to the teeth engagement as described above as teeth 66 of rod 60 cause the teeth of gears 69a, 69b of jaws 62a, 62b, respectively, to pivot (rotate) about the axis of pins 69c, 69d to rotate the claws 62a, 62b about an axis transverse to the longitudinal axis of the instrument to an open position. With the claws 62a, 62b in the open position, the instrument 50 (with the shaft, rod 66 and outer tube) is removed (withdrawn) from the patient's body, leaving the shaver head 52 within the disc space FIG. 6G. Thus, the shaver head 52 is effectively converted to a permanent implant, e.g., spacer, or an interbody cage or fusion device to receive bone or synthetic material therein for spinal fusion.

Figures 11, 12A, 12B:
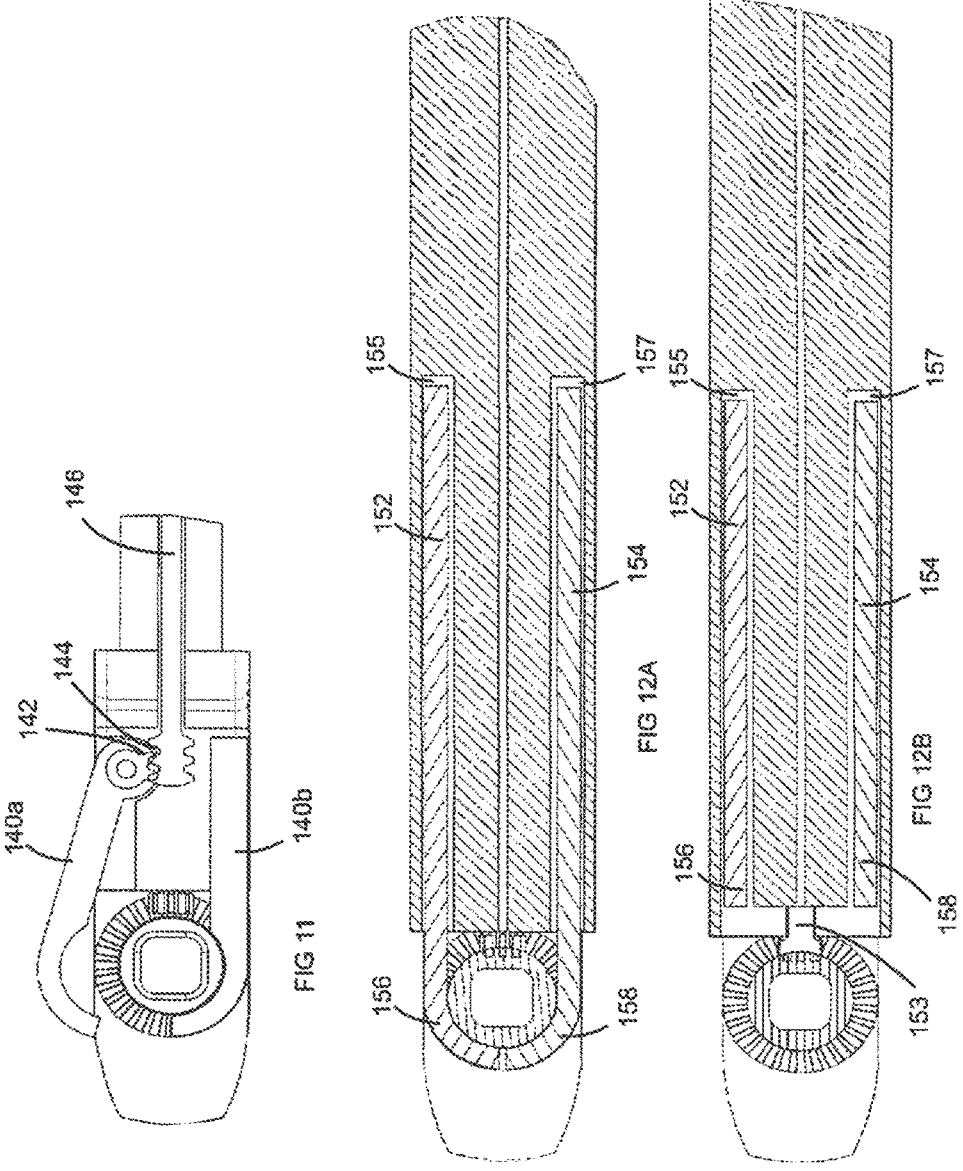
FIG. 11 is a bottom view of the upper shaver head of an alternate embodiment of the discectomy tool of the present invention having a shaver head detachable from the delivery shaft via a release rod.
FIG. 12A is a bottom view an alternate embodiment of the discectomy tool of the present invention having a shaver head detachable from the delivery shaft via retractable fingers, the fingers shown in the advanced (engaged) position.
FIG. 12B is a view of the discectomy tool similar to FIG. 12A showing the fingers in the retracted (release) position.
Figure 13:
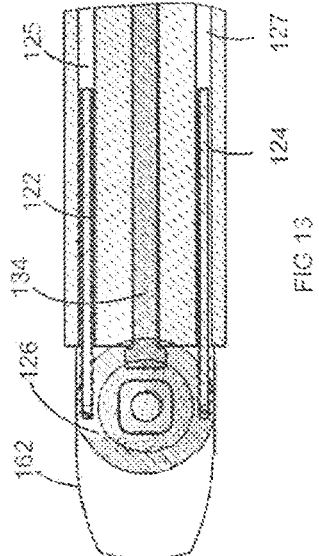
FIG. 13 is a bottom view of the upper shaver head of an alternate embodiment of the discectomy tool of the present invention having a shaver head detachable from the delivery shaft via a screw thread, the engagement screws shown in the advanced (engaged) position.

Although both claws are shown as movable in FIGS. 6A-6D, it is also contemplated that in an alternate embodiment, only one of the claws is movable. This is shown in the embodiment of FIG. 11 wherein only claw 140a is movable from an engaged to a release position due to the interaction of teeth 142 with teeth 144 of release rod 146. Claw 140b remains stationary as it is not engaged by rod 146. Movement of only one of the claws can in certain embodiments be sufficient to release the shaver head. In all other respects, the instrument of FIG. 11 is identical to the instrument of FIG. 6A. It should also be noted that in the other release mechanisms discussed herein, it is also contemplated that only one of the shaver head engagement (retention) members is movable to engage and release the shaver head from the instrument.

FIG. 7 illustrates an alternate embodiment of the release mechanism, similar to the embodiment of FIGS. 6A-6D. The clamp or jaws 70a, 70b function to move from a closed position to an open position, i.e., move between an engaged position to retain the shaver head to a disengaged position to release the shaver head. The release mechanism of FIG. 7 differs from that of FIG. 6A in the shape of the claws 70a, 70b and the provision of pinion gears 72a, 72b on base plate 78 that interact with rack 74 of the actuator rod 76. Note the other portions of the instrument are removed for clarity in FIG. 7 as only the release mechanism is shown, however, it should be appreciated that the release mechanism can be used with the various instruments and shaver heads described herein. When the rod 76 is retracted from its advanced (extended position) by an actuator at the proximal portion of the instrument, the rack 74 is moved (pulled) proximally, which causes rotation of gears 72a, 72b to pivot about an axis transverse to the longitudinal axis of the rod 76 (i.e., the axis of pins 73a, 73b) thereby spreading apart the C-shaped ends 75a, 75b of claws 70a, 70b, respectively, to release the hold on the receiver of the upper (or alternatively the lower) shaver head. The release position is shown in FIG. 7. Alternatively, distal movement of rod 76 can spread the claws 70a, 70b and proximal movement can close the claws 70a, 70b.

Alternative embodiments of release mechanisms for the shaver head are shown in FIGS. 8-15. In the embodiment of FIG. 8, a cam actuation mechanism moves engaging arms 80a, 80b between engaged and disengaged positions. Engaging arms 80a, 80b have projections or grippers 82a, 82b to engage the projecting surface (e.g., receiver or strut) of the shaver head (not shown), such as upper shaver head 18a or 52a. The arms 80a, 80b are spring biased to a closed position by spring 86. Movement of actuation rod 87 distally via an actuator at a proximal region of the instrument (e.g., adjacent the instrument handle) advances the cam 88 to move the arms 80a, 80b apart via cam follower 89 to a disengaged position. In the engaged position, the projections 82a, 82b hold (retain) the shaver head by engagement with the top, or alternatively the lower, shaver head as it contacts the projecting surface of the shaver head, e.g., projection 34 of shaver head 18a. In the disengaged position, the projections 82a, 82b are out of contact with the projecting surface of the shaver head. Retraction of cam 88 returns arms 80a, 80b inwardly to the engaged position.

Release mechanisms in the form of a screw actuation mechanism are shown in FIGS. 9 and 10. In the embodiment of FIG. 9, rotation of the threaded rod 92 (depicted by the arrow), causes release of the shaver head (not shown). More specifically, link 94 is L-shaped and has an engagement end or attached engagement member 98 and a connection end 94b which is connected to block 96 via pin 96a. Link 93 is L-shaped and is connected to link 94 via pin 97 at one end. Link 93 has an engagement end or attached engagement member 99 which opposes engagement end 98 of link 94. Thus, engagement ends 98, 99, act as gripping surfaces or holders, like the aforedescribed claws, to retain the shaver head (e.g., shaver head 18 or 52) by engagement of the projecting surface of the upper or lower shaver head, or engagement of another region. Note the link configuration and movement is asymmetric.

In use, when the rod 92 is rotated as depicted by the arrow, block 96 is moved distally due to engagement of the external threads of the rod 92 which the internal threads of block 96. Such distal movement of block 96 slides end 94b of link 94 distally, thereby moving attached engagement member 98 outwardly to the position of FIG. 9. Such movement of link 94 causes the link 93 to pivot outwardly about pivot pin 97 so that engagement member 99 is moved outwardly to the positon of FIG. 9. In this position, the shaver head (not shown) is released as the engagement members (or gripper) 98, 99 are moved out of contact with the shaver head (e.g., shaver head 18 or 52). Such release enables separation of the instrument from the shaver head so the shaver head can be left in the body to receive bone or other material as described herein.

A threaded rod is also utilized in the embodiment of FIG. 10 which has symmetric components and movement. Arms 102a and 102b are connected by links 104a, 104b which are connected at one end to block 106 via connecting pin 108. Link 104a is connected to arm 102a via pin 105 and link 104b is connected to arm 102b via pin 107. Arms 102a, 102b are joined at their proximal ends via link 110 and pins 112, 114. When threaded rod 103 is rotated in the direction of the arrow, it causes axial movement of block 106 which has internal threads engaged by the external threads of rod 103. Arms 102a, 102b have engagement surfaces, e.g., claws or grippers, 115a, 115b, respectively. Note the engagement surfaces can be formed at the ends of the arms 102a, 102b or alternatively be separate components attached to the arms 102a, 102b.

In use, when the rod 103 is rotated as depicted by the arrow, block 106 is moved distally due to the threaded engagement of the rod 103 and block 106. Such distal movement of block 106 forces spreading of links 104a, 104b to a larger angle, thereby causing arms 102a, 102b to move outwardly to spread engagement surfaces 115a, 115b, i.e., moving them outwardly to the position of FIG. 10. In this position, the shaver head (not shown) is released as the engagement members 115a, 115b are moved out of contact with the shaver head (e.g., shaver head 18 or 52). Such release enables separation of the instrument from the shaver head so the shaver head can be left in the body for fusion as described herein.

Figure 14:
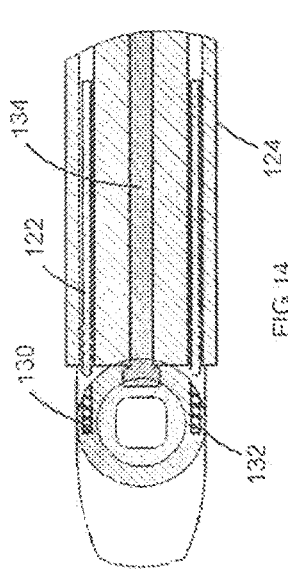
FIG. 14 is a top view similar to FIG. 13 showing the engagement screws in the retracted (release) position.
Figure 15B:
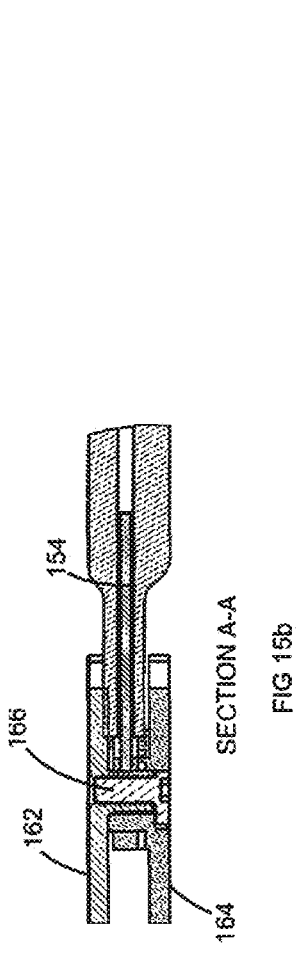
FIG. 15B is a longitudinal cross-sectional view taken along line A-A of FIG. 15A.
Figure 15A:
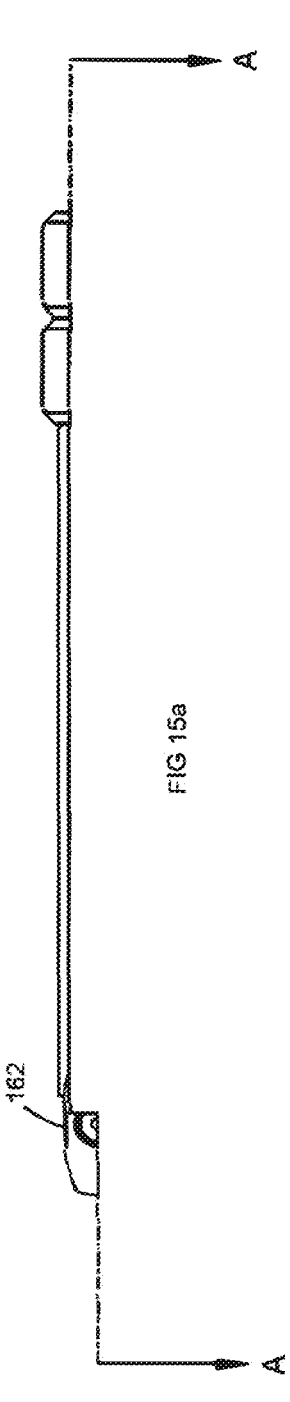
FIG. 15A is a side view of a portion of the discectomy tool of FIG. 13.

Another threaded engagement and release is shown in the embodiment of FIGS. 13, 14, 15A, and 15B. In this embodiment, a pair of threaded rods 122, 124 have external threads engageable with internal threads of the projection of the shaver head, e.g., shaver head 18 or 52. The threaded rods 122, 124 move within lumens 125, 127, respectively, of the instrument and are moved by a proximal actuator. As shown, projecting surface 126 of the upper shaver head 162 (or alternatively the lower shaver head) has first and second elongated threaded channels 130, 132. Rod 122 threadingly engages channel 130 and rod 124 threadingly engages channel 132. When it is desired to release the shaver head from the instrument, the rods 122, 124 are rotated to unthread from channels 130 and 132 until they are completely retracted from the channels 130, 132 as shown in FIG. 14. Once retracted out of the channels 130, 132, the shaver head 162 is no longer engaged and can be left behind in the body cavity when the instrument is withdrawn as the shaver heads 162, 164 are joined together by screw 166. Note the channels can be formed in any of the shaver heads described herein. Also note that a different number of threaded engagement rods can be provided. In all other respects the shaver heads 162, 164 of FIGS. 13 and 14 operate in the same manner to rotate to clean the disc space as the gear on shaft 134 (which can be identical to shaft 24 of FIG. 1C) engages the gear of the upper shaver head 162, or alternatively the lower shaver head 164, to rotate the upper and lower shaver heads. Note other types of engagement besides threaded engagement can be utilized to enable securement and desired detachment of the instrument and the shaver head.

In the embodiment of FIGS. 12A and 12B, the release mechanism for the shaver head is in the form of retractable fingers. More specifically, elongated fingers 152, 154 are positioned within lumens 155, 157 of the instrument. As shown, curved ends 156, 158 of fingers 152, 154, respectively, engage the projecting surface of the upper, or alternatively, the lower shaver head, as shown in the engaged position of FIG. 12A. The finger ends are biased to the curved position or alternatively can be composed of shape memory material with the shape memory state in the configuration of FIG. 12A. When it is desired to release the shaver head from the instrument, the fingers 152, 154 are pulled proximally from their engaged position of FIG. 12A. Due to the flexibility of ends 156, 158, as the fingers 152, 154 are pulled proximally, the ends 156, 158 disengage from the shaver head and are retracted into the channels 155, 157 as shown in the disengaged position of FIG. 12B. Due to their flexibility, the ends 156, 158 move to a linear position within the channels 155, 157. Once retracted to the disengaged position, the shaver head is no longer engaged and can be left behind in the body cavity when the instrument is withdrawn. Note the fingers 152, 154 can extend the length of the instrument so they can be actuated i.e., moved proximally by an actuator at a proximal end of the instrument. Alternatively, the fingers can have a shorter length such as shown in FIGS. 12A and 12B whereby a sufficient proximal force applied to the instrument when the shaver head is engaged in the disc space, retracts the fingers from engagement with the shaver head as the ends 156, 158 move into the channels 155, 157. Note that a different number of fingers can be provided. In all other respects the shaver head of FIGS. 12A and 12B, which includes an upper shaver head and a lower shaver head connected by an attachment screw, operate in the same manner to rotate to clean the disc space as the gear on shaft 153 (which can be identical to shaft 24 of FIG. 1C) engages the gear of the upper, or alternatively, the lower, shaver head to rotate the upper and lower shaver heads in the manner described in the foregoing embodiments.

As noted above, in alternate embodiments of the present invention, the shaver head is expandable. In the embodiments of FIGS. 1-15, the distance between the upper and lower shaver heads remains constant. In the alternate embodiment of FIGS. 16-20, the distance between the shaver heads can be changeable to expand, i.e., spread the shaver heads. This enables the shaver head to be adjustable to the size of the disc space and/or expand the disc space.

One way to achieve such expansion is shown in FIGS. 16-20. The shaver head, designated by reference numeral 170, includes an upper shaver head 172 and lower shaver head 174. Worm gear 176 is engageable with screw thread 175 on cylindrical extension or post 178 which extends downwardly from the upper shaver 172 (as viewed in the orientation of FIG. 19). Male post (projection) 178 is received in the opening in extension 180 (female receiver/ receptacle) of lower shaver head 174. With screw thread 175 extending perpendicular to the longitudinal axis of the instrument, rotation of gear 176 displaces extension 178 in the perpendicular (transverse) direction so that the lower shaver head 174 is displaced relative to the upper shaver head 172. The gear 176 can be positioned within cavity 179 of receiver 180 as shown. Note that alternatively, the upper shaver head 172 can be displaced relative to the lower shaver head 174 or both the lower and shaver heads can be displaced relative to each other. In any case, the upper and lower shaver heads are designed to move relative to one another with "relative movement" encompassing movement of only one of the shaver heads or of both of the shaver heads. Such relative movement enables insertion of the shaver head 170 in the retracted reduced profile position of FIG. 16. The elongated threaded rod 182 of FIG. 20 can be utilized to effect rotation of gear 176 to displace the shaver heads 172, 174. The threaded rod 182 can be actuated by the user at a proximal portion of the device, and its axial movement can be controlled by the user to control rotation of the gear 176 and thus move the shaver heads apart to a selected (desired) distance.

Figure 17:
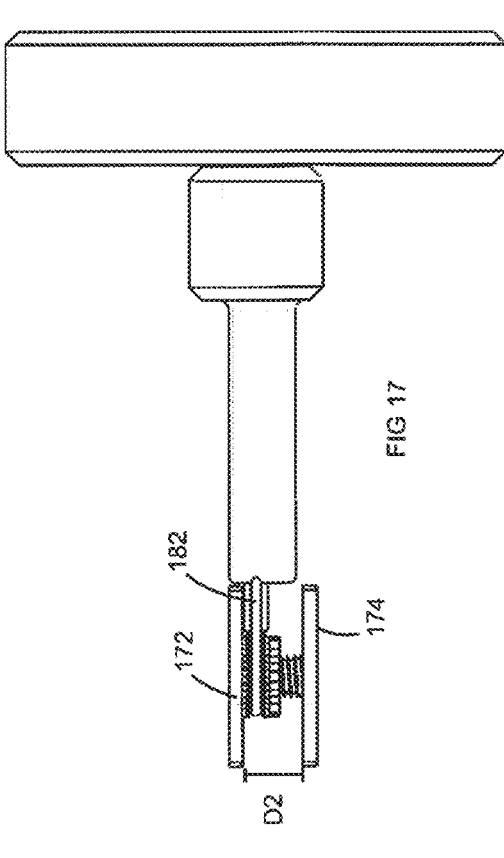
FIG. 17 is a side view similar to FIG. 16 showing the shaver head in the expanded position.
Figure 16:
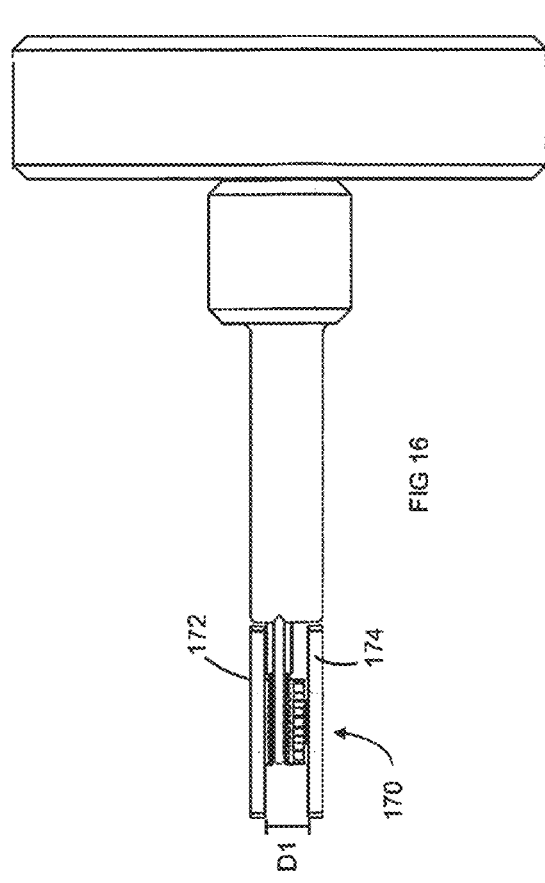
FIG. 16 is a side view of an alternate embodiment of the discectomy tool of the present invention having an expandable shaver head to increase the distance between the upper and lower shaver heads, the shaver head shown in the non-expanded (retracted) position.

The shaver head 170 can be rotated about its axis in the retracted position of FIG. 16 and in the expanded position of FIG. 17, as well as other positions in between. Note the shaver heads 172, 174 rotate together and about the same axis as shaver head 18 described above. If desired to spread the shaver heads 172, 174 apart to provide an increased profile (height) within the disc space for cleaning the space, the rod 182, engaged with the gear 176, is moved axially to effect rotation of gear 176 to change the distance between the upper shaver head 172 and the lower shaver head 174. FIG. 17 illustrates one example of an increased distance D2 between the upper and lower shaver heads 172, 174 as compared to the distance D1 of FIG. 16 which shows the non-expanded position. Note the shaver heads 172, 174 are parallel to one another and when expanded, i.e., spread, as the lower head 174 moves along the transverse axis, maintaining the parallel relationship. Such expansion movement along the transverse axis is also contemplated for other embodiments disclosed herein. In this and in other expandable shaver head embodiments disclosed herein, it is also contemplated that in some of these embodiments, rotation can be reversed to reduce the distance between the upper and lower shaver heads.

Note that FIGS. 16-20 show one example of a mechanism for expanding the upper and lower shaver heads. It is also contemplated that other mechanisms can be utilized to expand, i.e., increase the distance, between the upper and lower shaver heads. Such expansion can effect a movement along a transverse axis to maintain the substantially parallel position of the shaver heads with the inner surfaces facing one another and the outer surfaces engageable with the disc material. Expansion in other movements is also contemplated.

The shaver head 170 in the embodiment of FIGS. 16-20 is not detachable from the instrument. However, in alternate embodiments, the expandable shaver head is detachable from the instrument. The various detachment mechanisms described herein, e.g., retractable fingers, screw threads, etc., can be utilized with the instrument of FIGS. 16-20. To enable detachment, the engagement rod 182 can be separated, e.g., released from the gear 176, and thus be able to be removed with the instrument leaving the shaver head in the disc space as described above. Note in use, the shaver head, if desired, as with the other embodiments disclosed herein, can be expanded for rotation for use to clean the disc space and/or expanded after cleaning the disc space for use as an implant positioned within the disc space.

When the shaver head of the foregoing embodiments is used as an implant or cage to be left behind within the disc space, the shaver head can include a small chamber into which bone can be placed. The chamber can be formed in various regions of the shaver head, such as in the central strut (e.g. male post or female receiver) that extends between the upper and lower shaver heads or in openings in the surfaces of the shaver heads.

FIGS. 21A-26D illustrate an alternate embodiment of the discectomy tool of the present invention wherein the shaver heads are rotatable for clearing the disc space and are also expandable. The discectomy tool (also referred to as the discectomy device or instrument) is designated generally by reference numeral 200 and includes a body 203 with a shaft or outer tube portion 206 and a proximal housing 211 supporting the actuation mechanisms. The discectomy tool 200 includes an upper rotatable member (shaver head 212) and a lower rotatable member (shaver head 214), "upper" and "lower" referring to the orientation in FIG. 23). A slider 226, supported in recess 211*a* of housing 211 is slidable to disable and enable expansion of the shaver heads 212, 214; a T-handle 210 is actuable to rotate the shaver heads 212, 214.

The outer tube portion 206, also referred to herein as the elongated housing 206 extends distally from proximal housing 211. The tube portion 206 can have a necked down (reduced width/diameter) region 206*a* at a distal portion to improve visualization of the distal end of the discectomy device 200 during insertion. Further, the necked down region 206*a* enables the user to have a nerve tool retractor in position simultaneously with the discectomy tool 200. Such necked down version can be provided in any of the embodiments disclosed herein.

Figure 32:
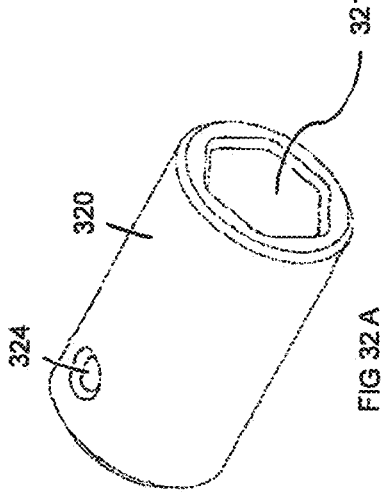
Figure 32:
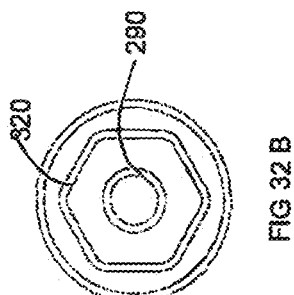
Figure 32:
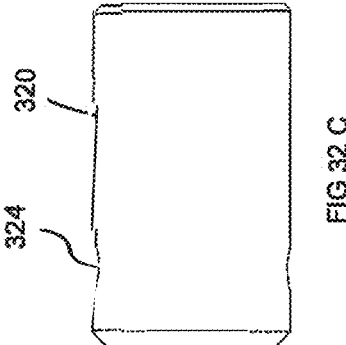
Figure 41:
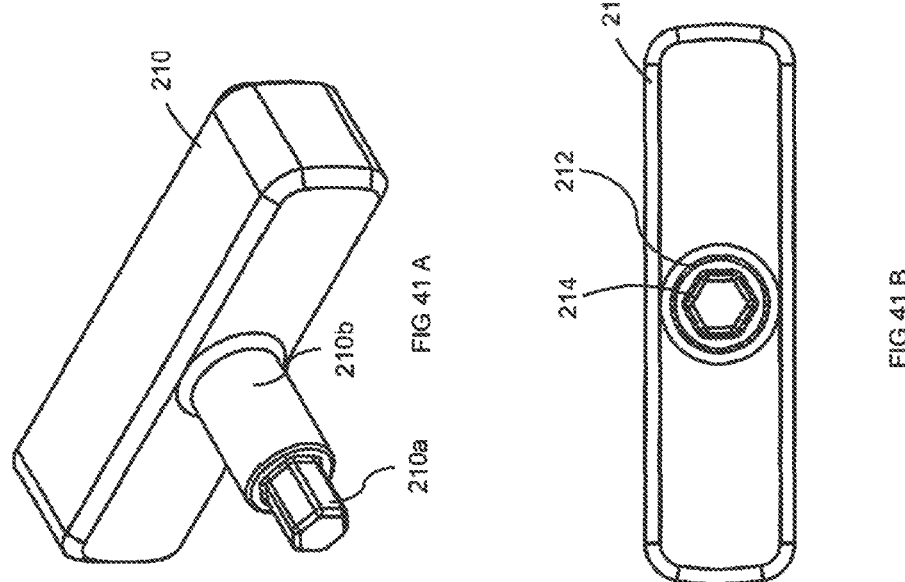
FIG. 41A is a perspective view of the rotation handle of FIG. 21A.
FIG. 41B is a front view of the rotation handle of FIG. 41A.
Figure 42:
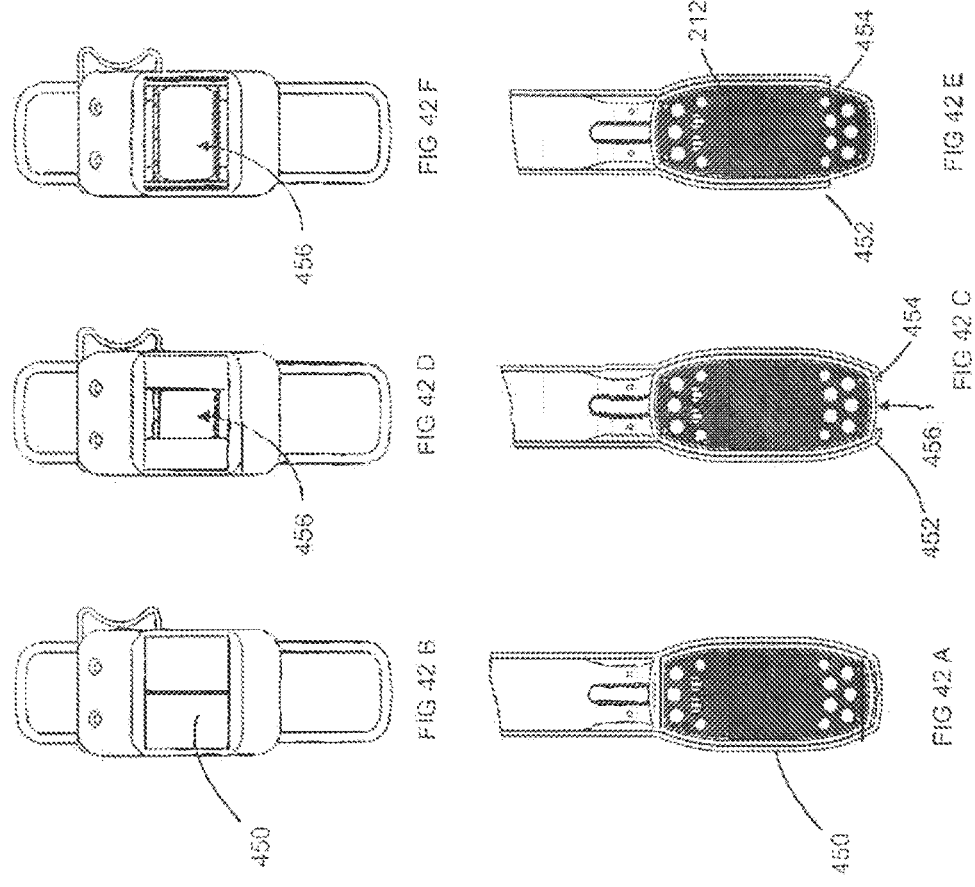
Figures 43, 44:
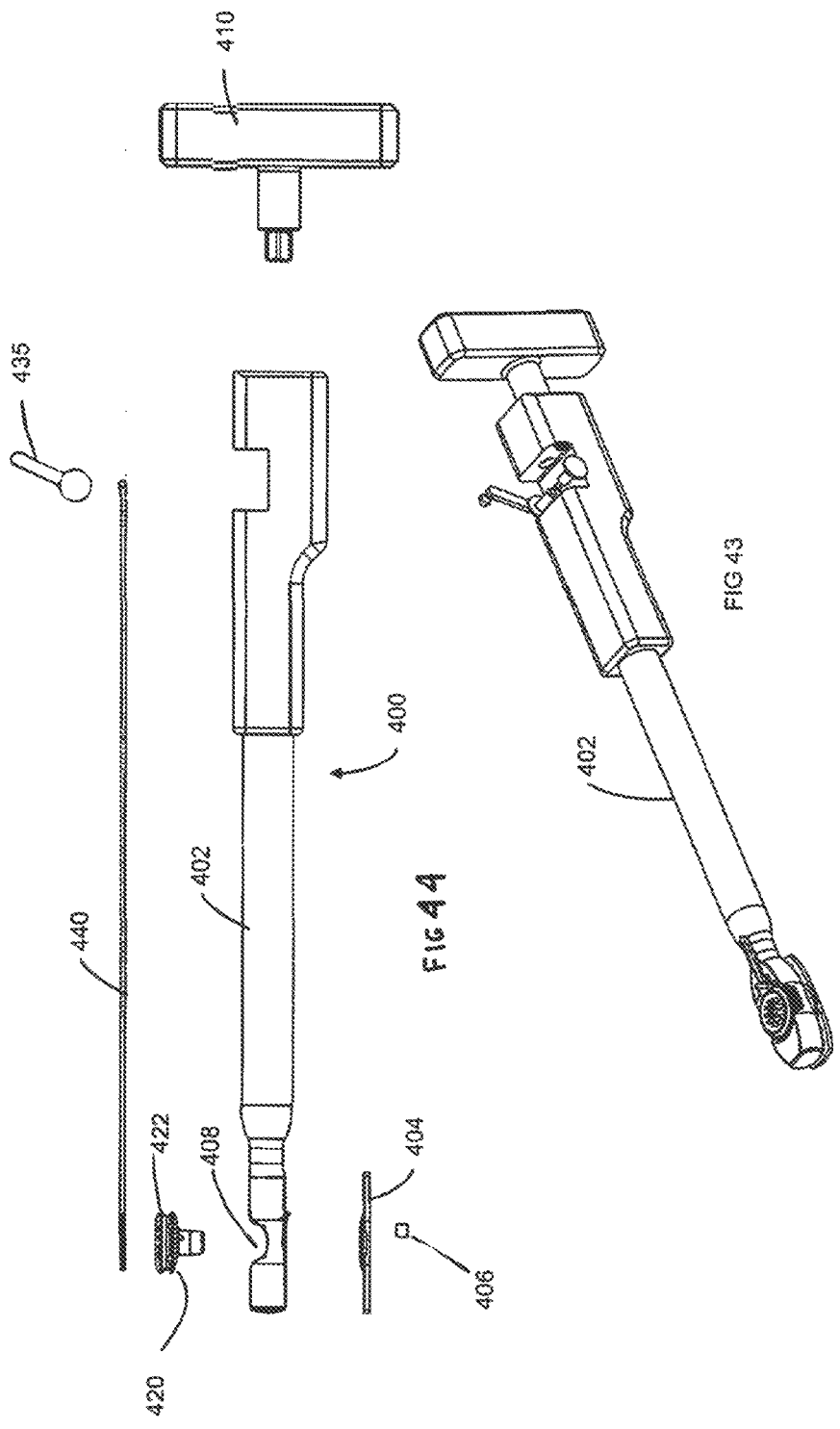
FIG. 43 is a perspective view of an alternate embodiment of the discectomy tool of the present invention having an actuation cable to effect expansion of the shaver head.
FIG. 44 is an exploded view of the discectomy tool of FIG. 43.
Figure 47:
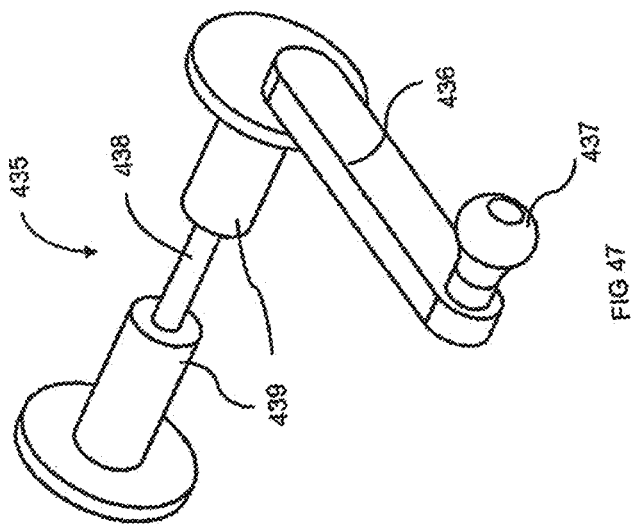
FIG. 47 is a perspective view of the crank of FIG. 43 for moving the cable to expand the shaver head.

Turning first to the shaver head rotation mechanism for rotating the shaver heads 212, 214, the rotation mechanism includes a hand operated actuator in the form of a T-handle 210 attached at a proximal end of the body 203 and an elongated member 290 in the form of a rod, also referred to herein as the drive rod, extending inside the body 203 within a lumen formed therein. The T-handle 210 has a reduced diameter post 210*a* extending from post 210*b* for insertion into opening 213 of housing 211. Hex sleeve 320 is positioned within a recess in housing 211 and has a longitudinally extending opening 321 (see also FIGS. 32A and 32B), to receive hexagonal shaped post 210*a* of handle 210 (FIGS. 41A and 41B). As shown in FIGS. 32A and 32B, opening 321 of hex sleeve 320 is hexagonal shaped to mate with post 210*a*. Opening 324 in the side wall of hex sleeve 320 receives transverse mounting pin 292. The T-handle 210 is mounted to the housing 211 during manufacture, however, in alternate embodiments, the handle 210 can be removably attached to sleeve 320 by a user such as a by a snap fit. T-handle 210 is designed ergonomically for ease of rotation by the user to effect drive rod rotation to cause shaver head rotation and clearing of the disc space as described below. However, it should be appreciated that other types or configurations of handles/actuators could alternatively be provided to effect drive rod rotation and shaver head rotation. Such alternate handles can be rotatable to rotate the drive rod or movable linearly (axially) and provided with a mechanism, e.g., gear, to convert the linear motion to rotary motion.

Figure 33:
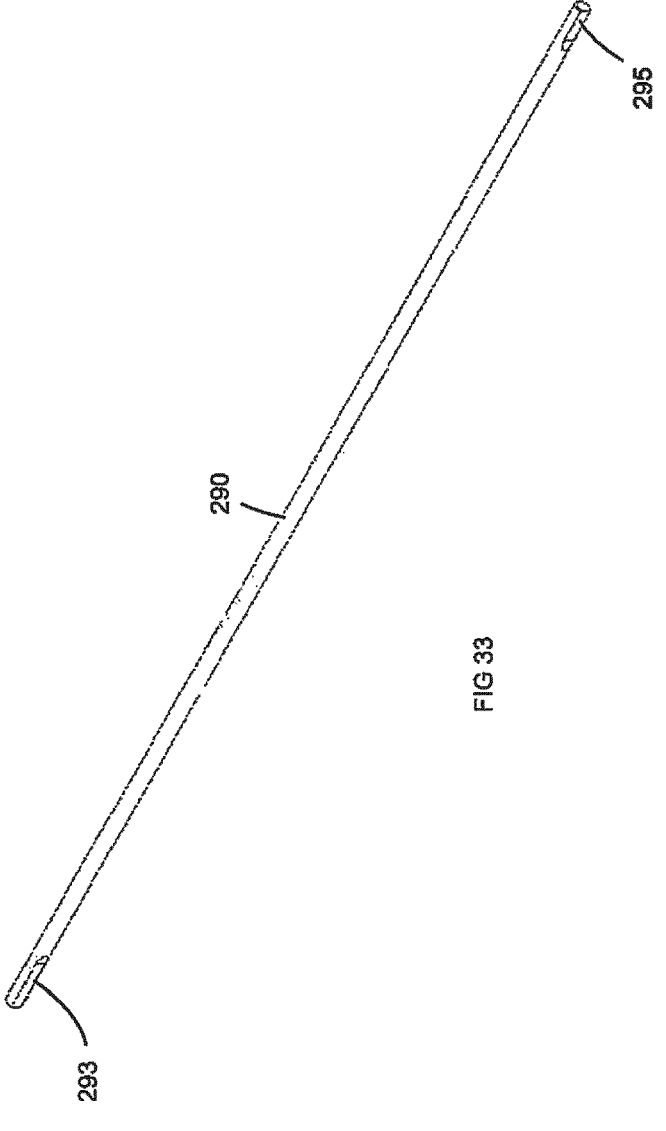
FIG. 33 is a perspective view of the drive shaft of the discectomy tool of FIG. 23.
Figure 34:
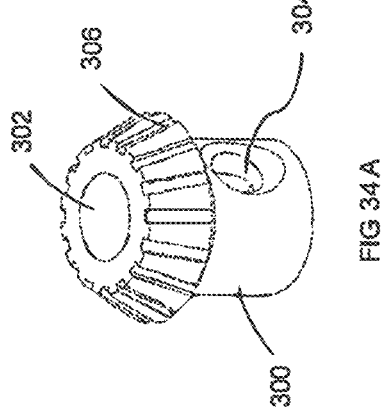
Figure 34:
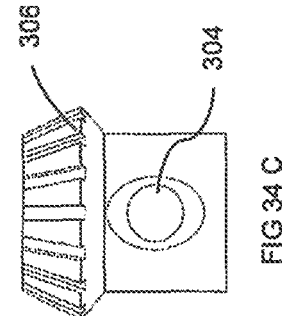
Figure 34:
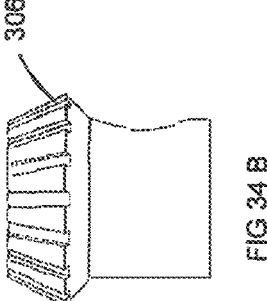
Figure 34:
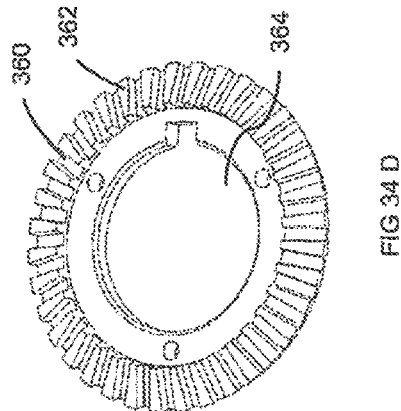
Figure 34:
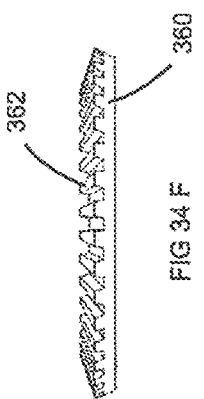
Figure 34:
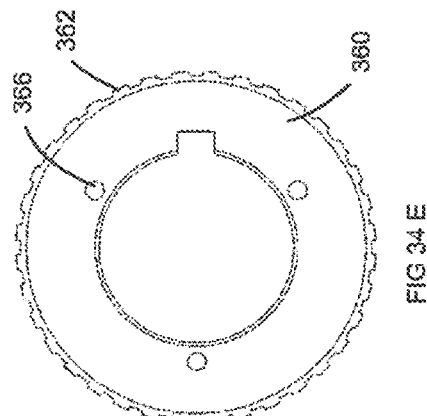
Figure 35:
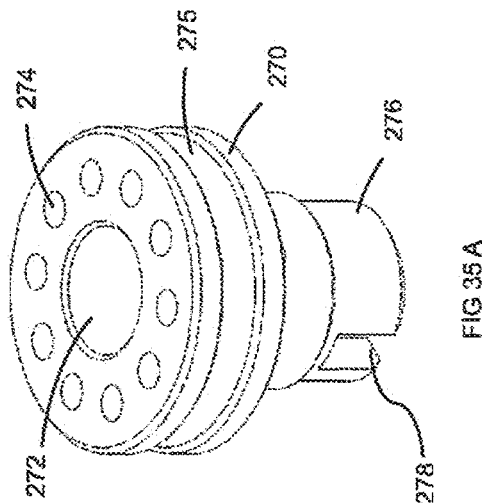
Figure 35:
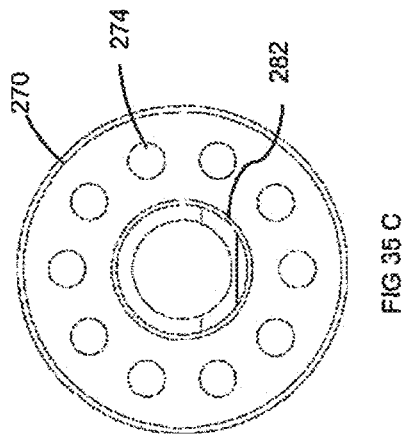
Figure 35:
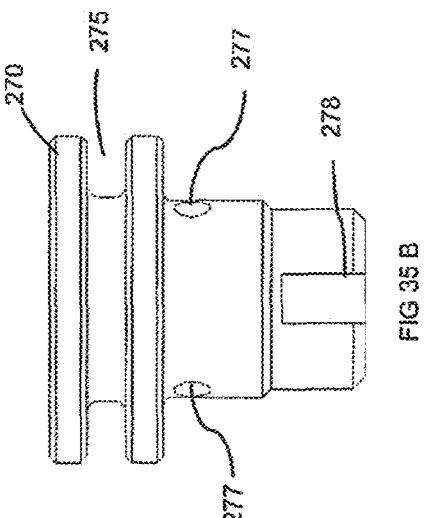

Drive rod 290 of the shaver head rotation mechanism, also referred to herein as the rotational rod or shaver actuation rod, has a proximal end with a flat 295 (see also FIG. 33) which is engaged by the sleeve mounting pin 292 that extends through the side opening 324 in hex sleeve 320. In this manner, mounting pin 292 secures the drive rod 290 to the hex sleeve 320 within housing 211 as shown in the cross-sectional view of FIG. 26A. The distal end of drive rod 290 has a flat 293. Drive rod 290 supports a pinion gear 300 at its distal end. Gear pin 297 extends though side opening 304 in pinion gear 330 to secure the pinion gear 297 and a washer 296 is interposed between the proximal wall of the pinon gear 300 and the distal end of the drive rod 290. As shown in FIGS. 34A-34C, pinion gear 300 has an opening 302 extending longitudinally therethrough to receive the drive rod 290 and a plurality of teeth 306 to interact with gear 360 of the shaver head to effect rotation of the shaver heads in the manner discussed below. The pinion gear 300, being attached to an end portion of drive 290, rotates with the drive rod 290 about the longitudinal axis of drive rod 290 with its teeth 306 also rotating about the longitudinal axis of the drive rod 290. Thus the pinion gear 300 rotation is about a longitudinal axis of the discectomy tool 300. Pinion gear 300 is oriented so its teeth extend circumferentially with respect to the longitudinal axis of the drive rod 290; shaver gear 360 is oriented transverse to pinion gear 300 with its teeth extending radially with respect to the longitudinal axis of the drive rod 290.

Figures 21, 22, 23:
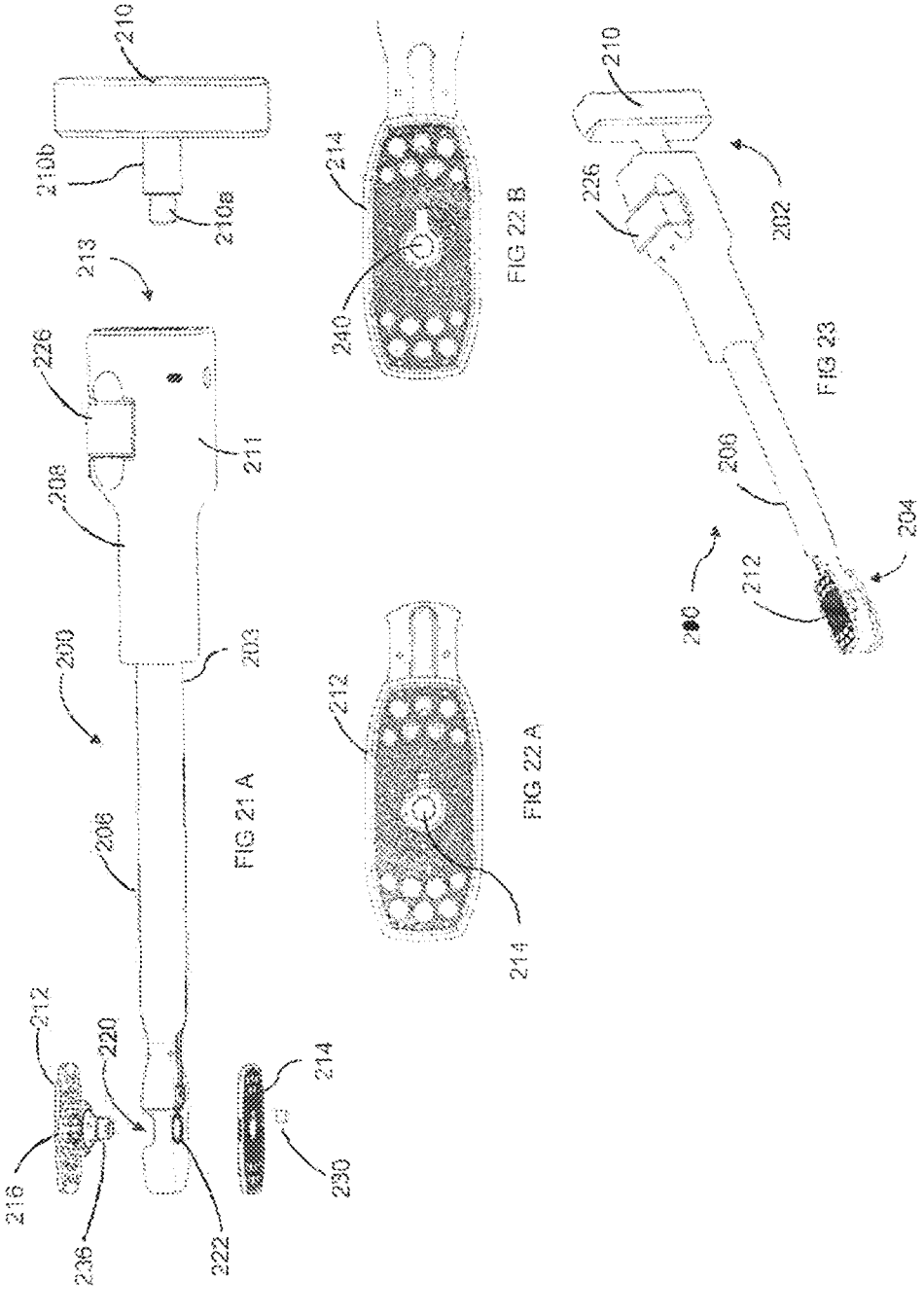
FIG. 23 is a perspective view of the discectomy tool of FIG. 21A, the shaver head shown in the non-expanded (retracted) position.
Figure 24:
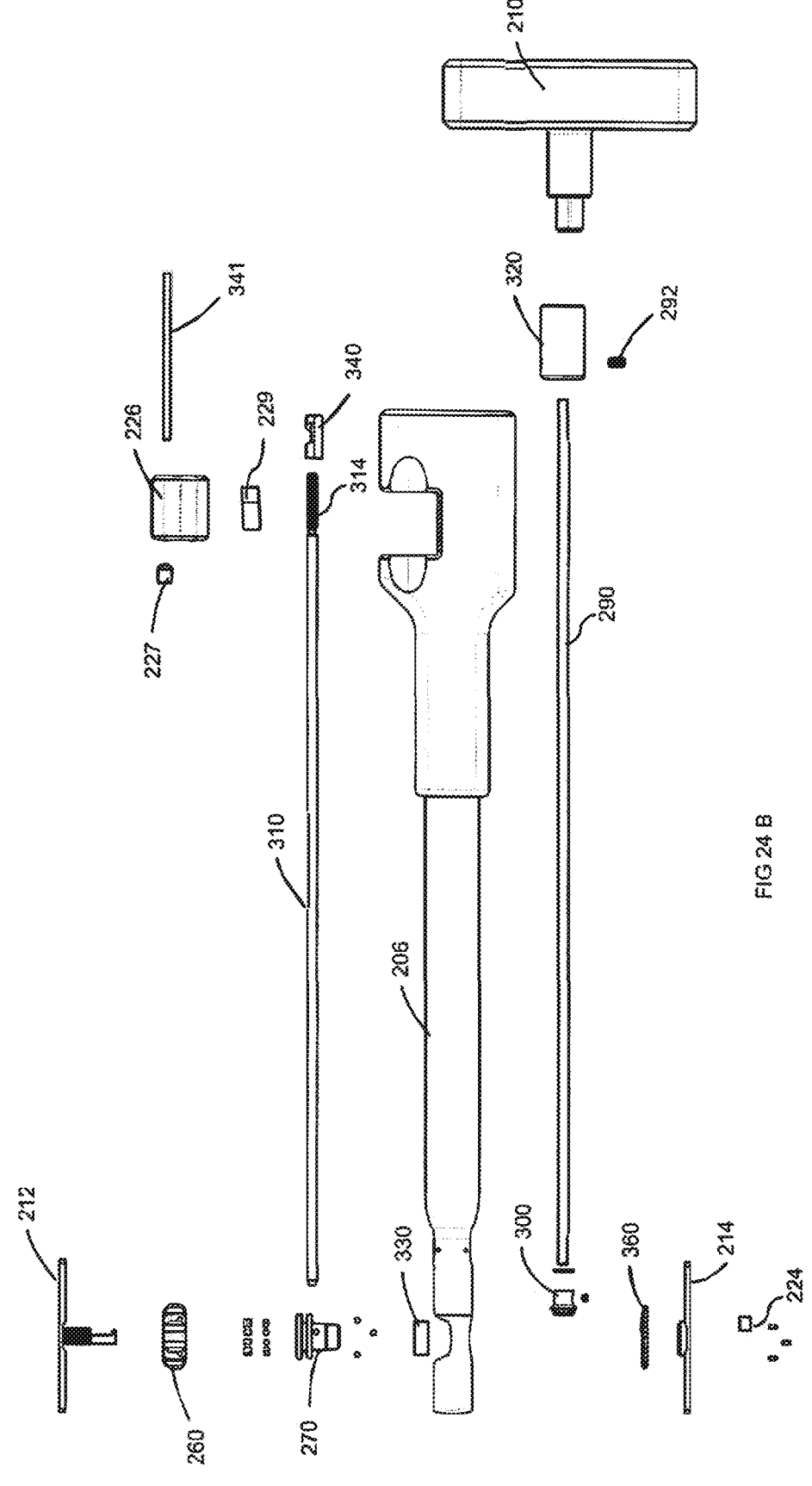
FIG. 24A is an exploded view of the body and actuation mechanisms of the discectomy tool of FIG. 21A (and FIG. 23)
FIGS. 24B and 24C are exploded views of the discectomy tool of FIG. 21A (and FIG. 23)
Figure 24:
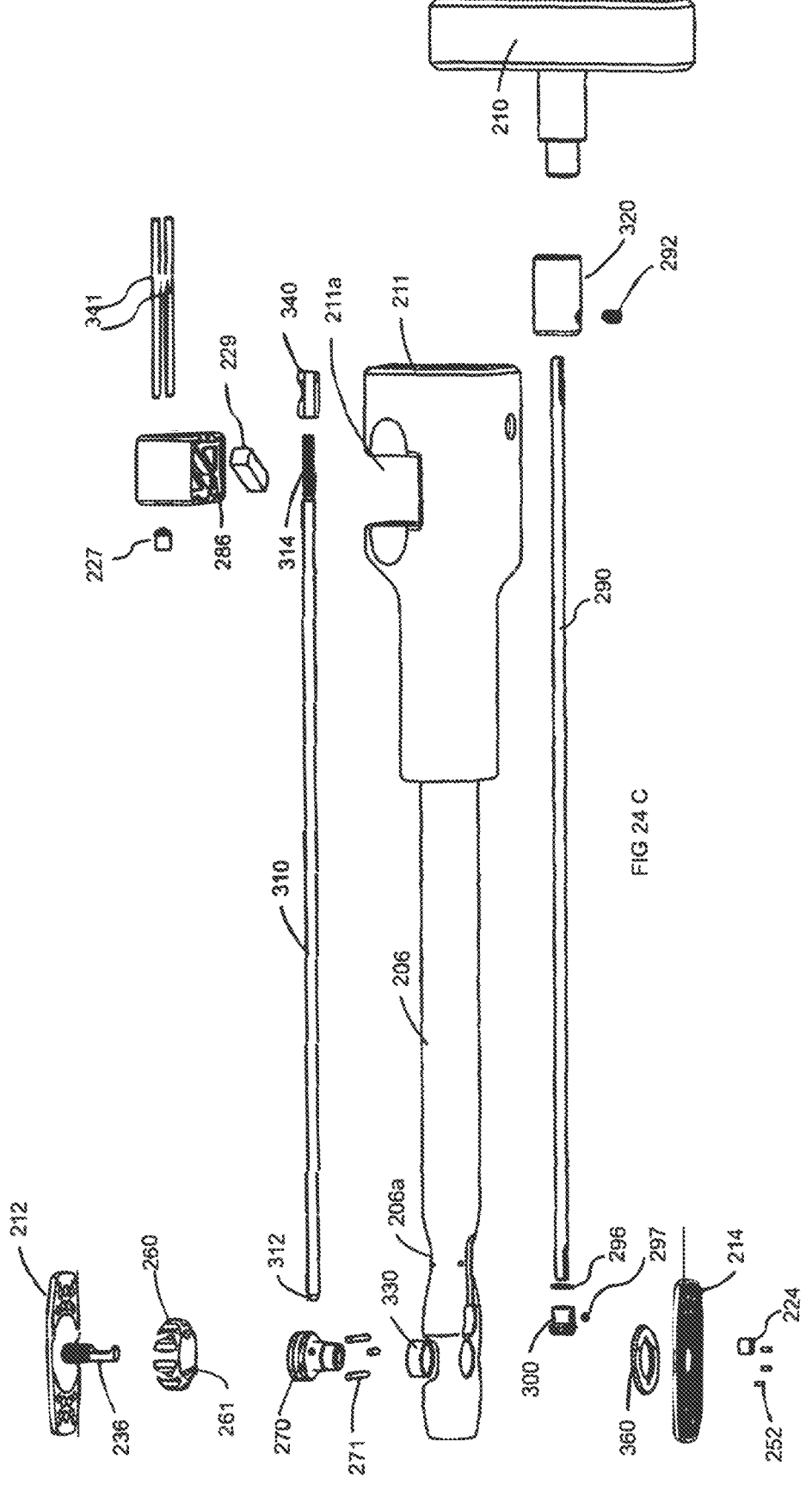
Figure 26:
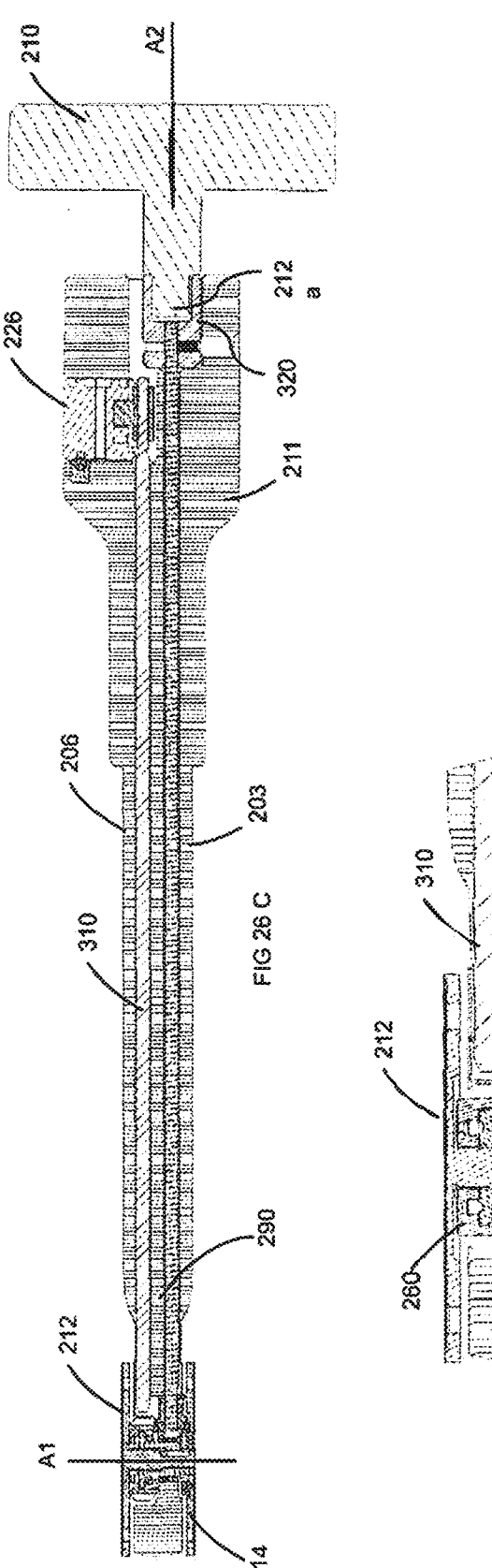
FIG. 26A is a cross-sectional view of the discectomy tool of FIG. 25.
FIG. 26B is a rear view of the discectomy tool of FIG. 26A.
FIG. 26C is a cross-sectional view of the discectomy tool of FIG. 23.
FIG. 26D is a close up view of the area of detail identified in FIG. 26C.
Figures 30A, 30B, 30C, 31:
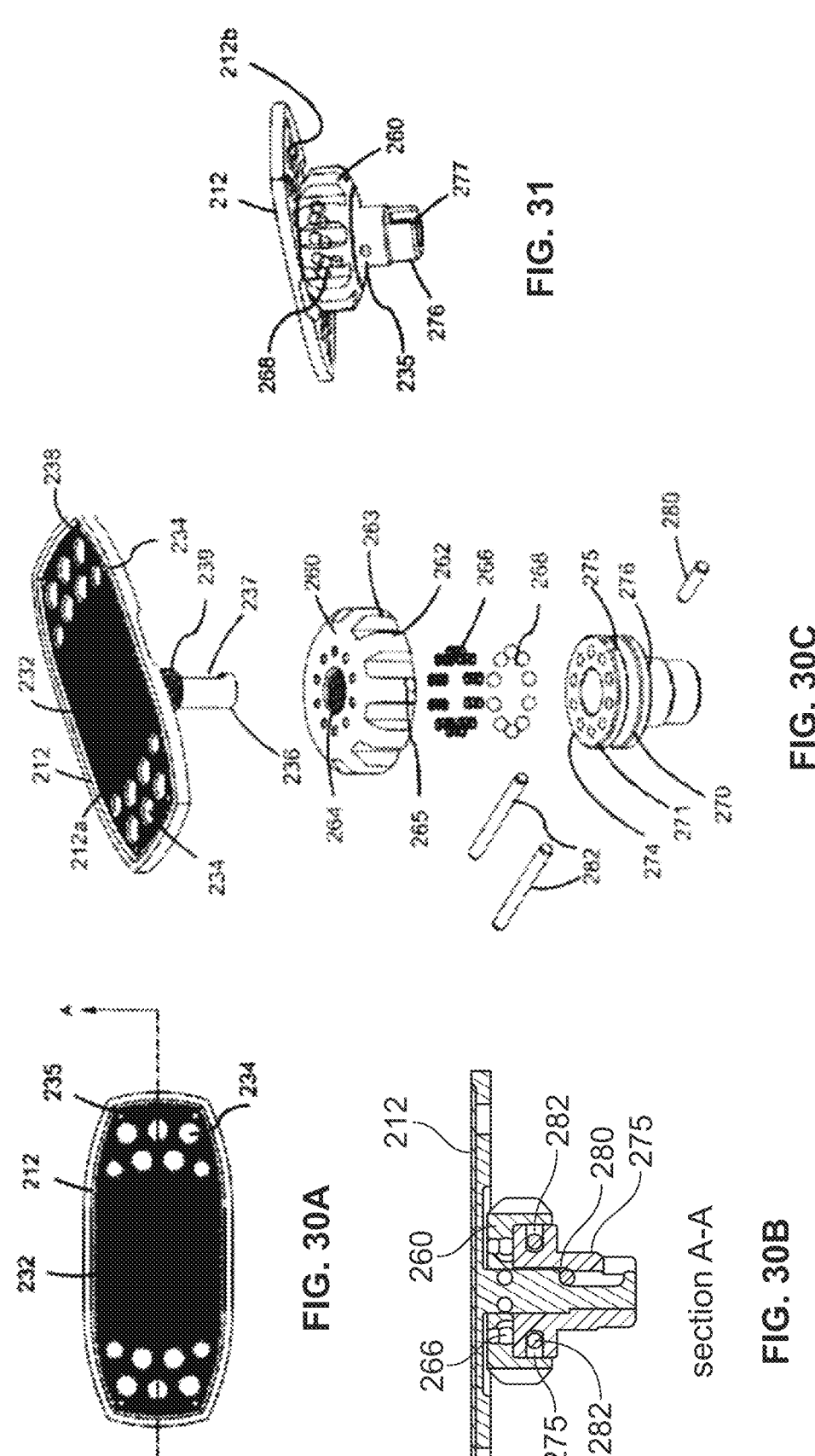

The shaver heads 212, 214 are also expandable, i.e., movable away from each to increase the distance between the upper and lower shaver heads 212, 214. In the embodiment of FIG. 23, the upper shaver head 212 is movable with respect to the lower shaver head 214 for expansion, however, in alternate embodiments, the lower shaver head 214 can be movable with respect to the upper shaver head 212, and in other alternate embodiments, both shaver heads can be movable away and toward each other. Thus, relative movement as defined herein means one or both of the shaver heads 212, 214 moves relative to the other shaver head. The shaver heads 212, 214 are movable along a transverse axis and maintained in parallel relationship as the distance between the shaver heads increases, i.e., the gap increases between the lower surfaces of the shaver heads 212, 214.

As noted above, as used herein throughout the various embodiments, the terms "lower" and "upper" refer to the orientation of the components shown in the Figures. If the orientation of the discectomy tool changes, then the "upper and "lower" positions would also change accordingly.

With reference to FIGS. 21A-26D the expansion mechanism for expanding shaver heads 212, 214 includes an elongated member in the form of an expansion rod 310 and an expansion rod actuator in the form of a slider 226. The expansion rod (shaft) 310 is positioned within the body 203, positioned parallel to the drive rod 290 in a lumen parallel to the lumen parallel to the lumen receiving the drive rod 290. The expansion rod 310 acts as an expansion enabling rod. The rod 310 is attached at a proximal end to slider 226 and is movable axially by the slider 226. Slider 226 is positioned in recess 211*a* of housing 211 and moves "left" and "right", i.e., transverse to the longitudinal axis of the expansion rod 310, to advance and retract the expansion rod 310.

Figure 39:
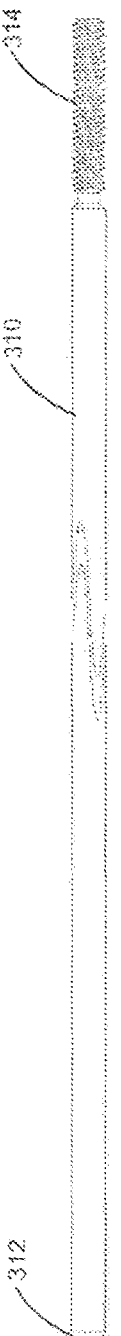
FIG. 39 is a side view of the expander rod of FIG. 24B.

Slider 226 is part of an expansion rod movement mechanism which includes ball engagement member 227, key 229, standoff 340 and pins 341. Pins 341 connect the slider 226 to the housing 211, and slots 288 of slider 226 (see FIG. 38A) enable sliding movement of the slider 226. Expansion rod 310 has a threaded portion 314 at its proximal end and an engagement tip 312 at its distal end (see also FIG. 39). Threaded portion 314 is received in standoff 340. Details of the standoff 340 are shown in FIGS. 40A-40C. Standoff 340 has a longitudinal opening 345 extending therethrough and a window 344 formed by angled cutouts to form angled walls 342*a*, 342*b*. As shown, walls 342*a*, 342*b* are at an angle to the longitudinal axis of the standoff, such as about a 30 degree angle, although other angles are also contemplated. Threads 346 of standoff 340 threadingly engage the proximal threads 314 of the expansion rod 310. The window 344 forms a recessed region to receive key 229. Slider 226 has a slot 286 on its bottom surface to receive key 285 (see FIG. 38B) which is positioned at an angle to the longitudinal axis of the standoff 340. In this manner, as the slider 226 moves transversely (right to left), the key 285 will engage the respective angled wall 342*a*, 342*b* of the standoff 340 to effect axial movement of the standoff 340 which in turn effects axial movement of the expansion rod 310 due to the threaded engagement of the expansion rod 314 and the standoff 340.

In the retracted position of the expansion rod 310, the distal engagement tip 312 is in a disengaged position, spaced from the sprocket 260 of the shaver head. In this position, rotation of the shaver head does not effect expansion of the shaver heads 212, 214. If shaver head expansion is desired, the slider 226 is moved to the right (or in alternate embodiments moved to the left) to advance the expansion rod 310 axially distally to an engaged position. In this engaged position, the distal engagement tip 312 engages the sprocket 260 of the shaver head mechanism to lock rotation of the sprocket 260. Details of the expansion rod tip and sprocket engagement in conjunction with the positions of the slider are discussed in detail below.

With reference to FIGS. 38A-38E, slider 226 has protrusions 287a and 287b on opposing sides to decrease the frictional forces of the slider in the recess 211a of the housing 211 to facilitate left and right sliding movement of the slider 226. Thus, the protrusions 287a, 287b minimize friction as the entire face of the slider 226 doesn't make contact with the walls of the housing 211. Recesses 289 receive the ball detent 227 to retain the slider 226 in its first and second positions. As shown, when the slider 226 is in a first or "left side" position as viewed in the orientation of FIGS. 38C-38E for the non-expansion mode, the ball detent 227 is in the right side recess 289; when the slider 226 is in a second or "right side" position as viewed in the orientation of FIGS. 38F-38H for the shaver head expansion mode, the ball detent 227 is in the left side recess 289. Note "first and "second" are used herein for reference and do not necessarily denote sequence.

It should be appreciated that other types of actuators are also contemplated to effect movement of the expansion rod. For example, axial slider, levers, rotation mechanisms, etc. can be utilized. Additionally, other mechanisms can be utilized to limit or effect shaver head expansion.

Note in the embodiment of FIGS. 21A-26D, the expansion of the shaver heads 212, 214 occurs as the shaver heads 212, 214 are rotated since the drive rod 290 effects movement of the upper shaver head 212 relative to lower shaver head 214. In alternate embodiments, the shaver heads can be expanded independent of rotation of the shaver heads. Examples of such embodiments are described below in conjunction with FIGS. 49A-50C.

Turning now to the distal portion of the discectomy tool 200 and the shaver heads 212, 214, and with reference to FIGS. 21A-26D, the rotational movement of the shaver heads 212, 214 is about axis A1 (as in the aforedescribed embodiments) and the expansion movement, i.e., change of distance between the surfaces of the upper and lower shaver heads 212, 214, is along axis A1. As shown in FIG. 26C, axis A1 is perpendicular to longitudinal axis A2 of the device body 203; axis A2 extends along the discectomy tool 200, e.g., parallel to the elongated members (rods) 290 and 310.

With reference to FIGS. 24B, 24C, 29A-29D and 30A-30C, the shaver head assembly includes lower rotatable member (shaver head) 214, upper rotatable member (shaver head) 212 and a rotation mechanism including sprocket 260 and hub 270.

Lower shaver head 214 has an outer surface 242, preferably knurled or formed with other irregularities to form a non-smooth surface to enhanced tissue engagement and can allow for/promote tissue ingrowth in the embodiments wherein the shaver head is detached from the tool and left in the body. Opening 240 receives the post 237 extending downwardly from upper shaver head 212 for connection to upper shaver head 212. A gear mount 250, extending from the upper surface, receives and secures gear 360 which interacts with the pinion gear 300 attached to drive rod 290. Lower shaver head 214 has a series of openings 244 on both of its ends and upper shaver head 212 also has openings 234 on opposing ends for receipt of grafting material in embodiments where the shaver head is detached from the tool and left in the body. Although seven holes are shown on each side of the shaver heads 212 and 214, a different number of holes and/or different size holes can be provided. The holes can also be positioned in other regions of the shaver heads than that shown. Shaver head 212 has small holes 235 adjacent its edges and shaver head 214 has small holes 248 adjacent its edges to support radiopaque markers, such as tantalum markers, for imaging. Holes 246 adjacent opening 240 of lower shaver head 214 receives pins 224 to help secure the gear 360 to lower shaver head 214 in addition to sleeve 330. Additional markers can also be provided in lower and/or upper shaver heads 214, 212.

The upper shaver head 212 has an outer surface 212a, preferably knurled or formed with other irregularities to form a non-smooth surface to enhance tissue engagement and can allow for tissue ingrowth in the embodiments wherein the shaver head is detached from the tool and left in the body. On the opposite side of outer surface 212a is an inner surface 212b which faces toward the inner surface 214b of lower shaver head 214. When the shaver head is expanded, the inner surfaces 212b, 214b move further apart and the outer surfaces 212a, 214a engage and apply a force to the tissue of the disc space to expand the disc space. The outer surfaces 212a, 214a also engage and remove the disc material upon rotation of the shaver heads 212, 214.

Figure 36:
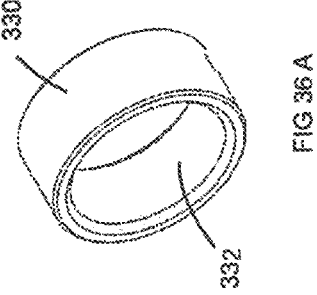
FIG. 36A is a perspective view of the shaver sleeve of FIG. 24B.
FIG. 36B is a cross-sectional view of the shaver sleeve of FIG. 36A.
Figure 36:
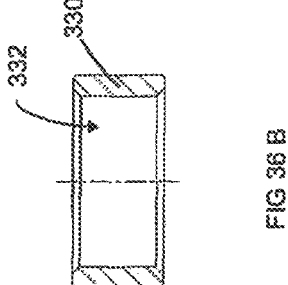
Figure 37:
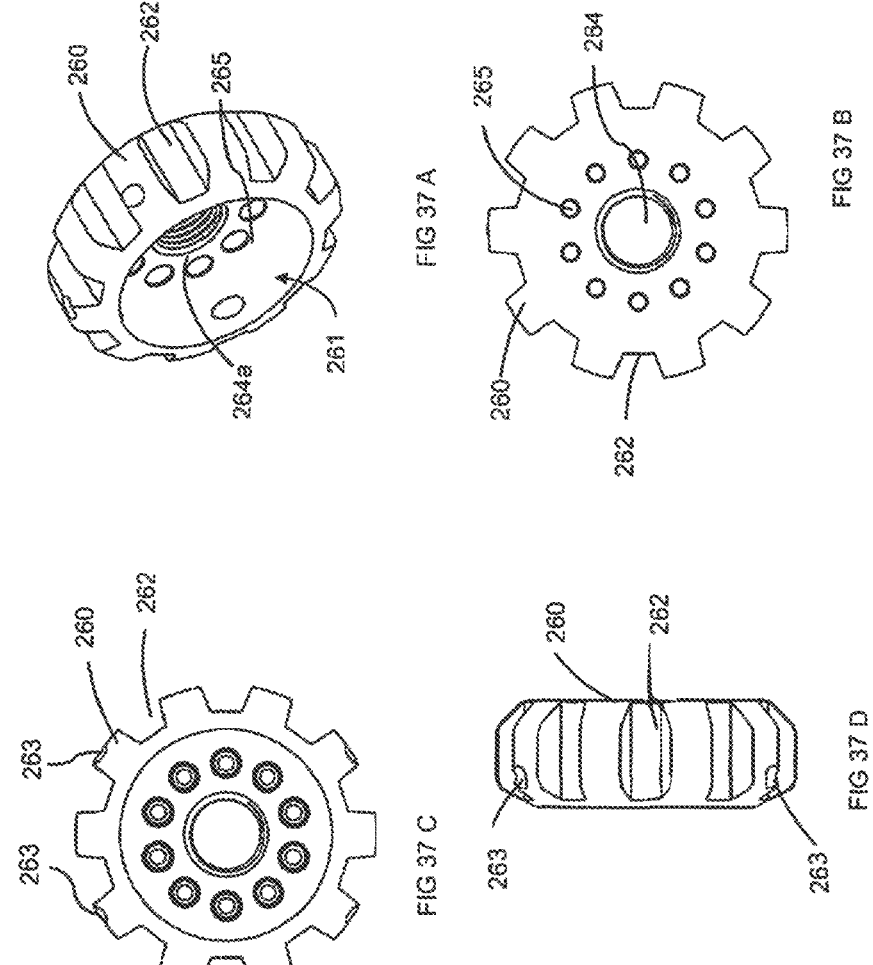

Sleeve 330 has an opening 332 (see also FIGS. 36A and 36B) and is positioned within recess 230 of body 203. The post 276 of hub 270 is positioned within the opening 332 of sleeve 300 such that the disc portion 271 of hub 270 sits atop the sleeve 330. The sleeve 330, being composed of metal provides a more rigid structure for the rotational components if the body 203 is composed of a plastic material. The gear 360 and bottom shaver 214 can be welded together and the attachment reinforced by pins 224 (FIG. 24C).

With reference to FIGS. 30B, 30C, 35A-35C and 37A-37D, the rotation components are illustrated and will now be described. The components include a sprocket 260, sprocket hub 270, springs 266, balls 268, a pair of pins 282 and a pin 280. Sprocket 260 has a threaded central opening 264 and a plurality of ribs 263 spaced about the circumference forming gaps or spaces 262 therebetween. These gaps 262 receive the expansion rod 310. Each of two side holes 265 is configured to receive an elongated pin 282. Hub 270 has post 276 and a disc portion 271 having a circumferential slot 275 shown extending the full 360 degrees about the hub disc portion 271. Pins 282 extending through opening 265 extend into the slot 275 of hub 270. As can be appreciated by reference to FIGS. 24C and 30B, the disc portion 271 is received in recess (opening) 261 of sprocket 270 and the pins 282 are captured within circumferential slot 275, thus securing the two components while allowing rotation of the hub 270 relative to the sprocket 260 for expansion as described below. Pin 280 extends though opening 235 in post 276 of hub 270. The pin 280 is captured in the slot 237 of the post 236 of the upper shaver head 212. Thus, as the hub 270 moves upwardly to its uppermost position in the shaver head expansion mode, the pin 280 will bottom out on the lower shelf of post 236 to prevent detachment of the hub 270 and upper shaver head 214. Key 224, as shown in FIGS. 24C and 26D, extends through the bottom shaver head 214, gear 360 and hub 270 and is positioned next to the post 276 of upper shaver head 212 within the central opening 240 of lower shaver head 214, and can be welded thereto, to secure the upper and lower shaver heads 212, 214 together so the shaver heads 212, 214 rotate together when actuated.

Hub 270 has a series of dimples 274 on its upper surface. The dimples 274 are aligned with holes in the sprocket 260. Balls 268 are biased by springs 266 into the dimples 274. When the shaver heads 212, 214 rotate without expansion, hub 270 and sprocket 260 rotate together, with balls 268 remaining in dimples 275. When the shaver heads 212, 214 rotate with expansion, the sprocket 260 is locked/blocked from rotation, and the hub 270 rotates relative to the sprocket 260, with the balls 268 engaging different dimples as the hub is rotated. In some embodiments, the balls and dimples can be configured so there is an audible and/or tactile feedback to the user to indicate that the shaver heads are in the expansion mode and rotation of the shaver heads will effect increase of the distance between the shaver heads to expand the disc space during rotation.

In the alternate embodiment of FIG. 27A-28B, the discectomy tool 200' has additional structure/features to enable detachment of the shaver head assembly from the discectomy tool. The discectomy tool 200' is identical to discectomy tool 200 except that the drive rod 290' releasably engages sleeve 330'. Sleeve 330' has a side opening 331 with threads to threadingly receive the distal threads 291 of drive rod 290'. The drive rod 290' functions in the same manner as drive rod 290 except that if desired, the drive rod 290' can be rotated with respect to the sleeve 330' to detach from sleeve 330'. FIG. 27B illustrates the drive rod in the engaged position with sleeve 330'; FIG. 27C illustrates the drive rod 290' out of engagement with sleeve 330'. In all other respects, the discectomy tool of FIGS. 27A-28B operates in the same manner, and have the same components, as the discectomy tool 200 of FIGS. 21A-26D, and therefore for brevity further discussion is not provided as the discussion of the structure and function of discectomy tool 200 is fully applicable to the discectomy tool of FIGS. 27A-28B.

Note the rotation of the drive rod 290 for detachment from sleeve 330' is achieved in one embodiment by locking gear 360 so that rotation of the drive rod 290' no longer rotates the gear 260 and thereby detaches (unthreads) from the sleeve 330' when rotated by the handle 210. Other mechanisms to lock rotation and allow detachment, or to enable detachment, to separate and leave the shaver head assembly in the disc space, are also contemplated.

Use of the discectomy tool 200 of FIGS. 21A-26D, will now be described. The shaver head of tool 200 can be operated in two ways/modes: 1) rotation to clear the disc space without expansion (referred to herein as the non-expansion mode); and 2) rotation with expansion (referred to herein as the expansion mode). Whether there is expansion during rotation depends on the user selected position of the expansion rod 310.

As discussed above, the expansion rod 310 is moved axially by the slider 226. In the non-expansion position, shown for example in FIGS. 38C-38E, the slider 226 is to the left (as viewed from the top). Detent 227 engages recess/groove 289 of the slider 226 to retain it in position (FIG. 38C). In this position, the distal tip 312 of the expansion rod 310 is out of engagement with the openings 263 in the sprocket 260. Thus, when the drive rod 290 is rotated by rotation of the T-handle 210 at the proximal end of the discectomy tool 200, pinion gear 300 at the end of the drive rod 290 rotates shaver gear 360 attached to lower shaver head 214 which causes rotation of the hub 270 and sprocket 260 and attached upper shaver head 214. Due to the attachment of the upper shaver head 212 to the lower shaver head 242, and the connection of the hub 270 and sprocket 260 to the post 236 of the upper shaver head 212, rotation of the drive rod 290 rotates both shaver heads 212, 214 about the transverse axis A1. Since both the sprocket 260 and hub 270 rotate, the shaver heads 212, 214 are maintained the same distance apart and rotate without expansion in this non-expansion mode. That is, the lower surfaces of the shaver heads 212, 214 remain a constant distance apart as the upper surfaces remain a fixed distance and engage and clear the disc material from the disc space.

If expansion of the shaver heads 212, 214 is desired by the user, the slider 226 is moved to the opposing side, e.g., right side, as shown in FIGS. 38F-38H. In this position, key 285 engages the distal angled wall 342b of standoff 340 and cams the standoff 340 distally, thereby moving the attached expansion rod 310 distally so the distal tip 312 of expansion rod 310 engages one of the openings 263 in sprocket 260. (The opening 263 engaged depends on the rotational position of the sprocket 260 at the time of transfer to the expansion mode). Ball detent 227 now engages the other recess/groove 289 of slider 226 to retain the slider 226 in the expansion position. The engagement of opening 263 by expansion rod 310 prevents rotation of the sprocket 280. In this locked or blocked position of sprocket 280, when the drive rod 290 is rotated by handle 210 to rotate gear 360 via pinon gear 300, hub 270 rotates relative to the sprocket 260, rather than in conjunction with the sprocket 260 as in the non-expansion mode. Such rotation when the sprocket 260 is locked causes the upper shaver head 212 to move upwardly relative to the lower shaver head 214 as its threads 239 on post 237 unthread from threads 264 of sprocket 260. Thus, as can be appreciated, in this embodiment, the T-handle 210 and drive rod 290 effect rotation of the shaver heads 212, 214 with and without expansion, as the expansion rod position determines whether expansion will accompany rotation.

As can be appreciated, the user can rotate the shaver heads 212, 214 without expansion. Therefore, at any time before or during the surgical procedure, the user can actuate the slider 226 to change the discectomy tool 200 to the expansion mode such that expansion, i.e., spreading, of the shaver heads 212, 214 accompanies rotation to expand the disc space. At any time before or during the procedure, the user can transfer the discectomy tool 200 back to the non-expansion mode so the shaver heads 212, 214 can be rotated without expansion.

Note that in use in the embodiments wherein the shaver head is detachable, after rotation to clear the disc space, the tool can be removed from the shaver head leaving the upper and lower shaver heads in a fixed, preferably expanded position, to function as a spacer, fusion cage, bone graft framework, etc. as the shaver heads are left in the patient's body.

FIGS. 52-54 illustrate an alternate embodiment of the present invention having a detachment mechanism and a locking mechanism for the shaver head. The shaver head assembly is illustrated in these Figures, it being understood that the mechanism for shaver head rotation and for shaver head expansion, if provided, can be identical to those described herein with respect to other embodiments.

The shaver head assembly of FIGS. 52-54 includes upper shaver head 212 and lower shaver head 214 as described above. This embodiment differs from the embodiment of FIG. 30C in features of the sprocket 660 and the hub 675, and the provision of locking members in the form of pins 680 and springs 682. Springs 682 bias pins 680 toward the upper shaver head 212. In the engaged position of FIG. 53, the projections 687 and 689 of jaws (claws) 686, 688, respectively, extend through slot (or multiple slots) 694 in hub 690 to engage a lower portion of pins 680. More specifically, projections 687, 689 engage lower flange 680c of pins 680, although alternatively they can engage reduced diameter portion 680b. The flange 680c provides a larger gripping surface for the jaws 686, 688. In this engaged position, the pins 680 are held in a lower position (as viewed in the orientation of FIG. 53), against the bias of springs 682. In this lower position, the upper flange or head 680a of pins 680 is outside (or substantially outside so they engage in a detent fashion) of slot 662 of sprocket 660. (Note transverse pins 684 function like pins 280 and 282 of FIG. 30C so for brevity are not further discussed herein). In this engaged position, the shaver heads 212 and 214 are rotated to remove material from the disc space, and can be expanded if expansion is provided as in other embodiments described herein which provide expansion.

If desired to separate the tool from the shaver heads 212, 214 to leave the shaver head assembly in the disc space as described with respect to other embodiments disclosed herein, the jaws 686, 688 are opened, i.e., spread apart via an actuator at the proximal end of the tool. When opened, the locking pins 680 are released and move upwardly into slot 661 of sprocket 660 via the force of springs 682. As shown in FIG. 54, the pins 680 extend into the lower region of slot 661, i.e., the larger diameter region, but cannot extend into the smaller diameter region 663 due to the enlarged head/flange 680a of pins 680. In this position, the pins 680 help prevent movement of the upper shaver head 212 from the lower shaver head 214 over time within the disc space due for example to slight unthreading of upper jaw 214. Thus, the pins 680 help lock the position of the shaver heads 212, 214 relative to one another when left within the disc space. The tool, when detached, is removed from the patient's body leaving the shaver head assembly behind.

In the embodiment of FIGS. 21A-26D, expansion accompanies rotation. In alternate embodiments of the present invention, expansion of the shaver heads is independent of expansion. Two examples of such embodiments are shown schematically in FIGS. 49A-50C.

In the embodiment of FIGS. 49A-49C, the addition of a slider 514 between the sprocket and pinion gear enables independent expansion, i.e., expansion without rotation. FIG. 49A shows the discectomy tool in a non-expansion mode wherein shaving via rotation of the shaver heads occurs without expansion. In this position, the pinion gear 504 of drive rod 506 engages lower shaver head gear 508 of lower shaver head 510. Note the drive rod 506, pinion gear 504, shaver head gear 508 and lower shaver head 510 are the same as drive rod 290, pinion gear 300, shaver head gear 360 and lower shaver head 214 of the embodiment of FIGS. 21A-26D. Furthermore, the upper shaver head and other components of the instrument are not shown as they are the same as in discectomy tool 200 described above. Thus, other than the elongated slider 514 and sprocket 518 (and independent expansion) the description above of the components and function of discectomy tool 200 is applicable to that of the tool of FIGS. 49A-49C and for brevity is not repeated.

Elongated slider 514 has a pinion gear 516 at its distal end to engage gear teeth 519 of the sprocket 518. In the non-expansion position (mode) of FIG. 49A, pinion gear 516 of elongated slider 514 is out of engagement with gear teeth 519 of sprocket 518. Therefore, rotation of drive rod 506 via the T-handle (not shown) rotates pinion gear 504 of drive rod 506 to rotate the sprocket 518 and hub (not shown) to rotate the shaver heads in the same manner as rotation of shaver heads 212, 214.

If it is desired to rotate the shaver heads with expansion, the expansion rod 520, which is identical to expansion rod 310 of discectomy tool 200, is moved distally by the slider to engage and lock the sprocket 518. (The slider could be the same as slider 226, or alternatives thereof, for effecting movement of the expansion rod). In this position of FIG. 49B, as in the expansion mode of discectomy tool 200 described above, rotation of the pinon gear 504 and shaver head gear 508 effect both rotation of the shaver head and movement of the upper shaver head away from the lower shaver head as the hub rotates and the sprocket 518 is locked from rotation. In this expansion mode of FIG. 49B, the pinion gear 516 of slider 514 remains out of engagement with sprocket 518.

If the user desires to expand the shaver heads without rotation of the shaver heads, the expansion rod 520 is moved to the non-expansion position disengaged from the sprocket 518 as shown in FIG. 49C. The elongated slider 514 is retracted (moved proximally) by an actuator at the proximal end of the discectomy tool so the pinion gear 516 of slider 514 is in engagement with teeth 519 of sprocket 518. Retraction of the elongated slider 514 also pulls drive rod 506 proximally so that pinion gear 504 of drive rod 506 is out of engagement with shaver head gear 508. In this position, when drive rod 506 is rotated, pinion gear 504 does not rotate shaver head gear 508 because it is out of engagement, but rotates sprocket 518 due to engagement of pinon gear 516 with gear 519. As the sprocket 518 rotates, the upper shaver head unthreads from the threads of sprocket 518. The upper shaver head can engage the sprocket via threads on a post like the threads 239 of post 236 of upper shaver head 212 of the discectomy tool 200. Thus, in this embodiment, the user can control at any time before or during the procedure the expansion rod 520 to enable expansion with rotation as well as control at any time before or during the procedure the elongated slider 514 to enable expansion without rotation.

It should be appreciated that a similar system can be used if the shaver gear is on the upper shaver head rather than a lower shaver head. Also, various actuators at the proximal end of the instrument can be utilized to control movement of the expansion rod and elongated slider.

FIGS. 50A-50C illustrate an alternate embodiment to enable expansion without rotation, i.e., expansion independent of rotation. In this embodiment, rather than the addition of an elongated slider as in the embodiment of FIGS. 49A-49C, the pinion gear has back and forth teeth (proximal and distal teeth). The addition of these teeth to engage the sprocket and pinion gear enables such independent expansion.

FIG. 50A shows the discectomy tool in a non-expansion mode wherein shaving via rotation of the shaver heads occurs without expansion. In this position, the pinion gear 524 of drive rod 526 engages lower shaver head gear 528 of lower shaver head 530. Note the drive rod 526, pinion gear 524, shaver head gear 528 and lower shaver head 530 are the same as drive rod 290, pinion gear 300, shaver head gear 360 and lower shaver head 214 of the embodiment of FIGS. 21A-26D. Furthermore, the upper shaver head and other components of the instrument are not shown as they are the same as in discectomy tool 200 described above. Thus, other than the drive rod 526, its pinion gear 524 and sprocket 528

(and independent expansion), the description above of the components and function of discectomy tool 200 is applicable to that of the tool of FIGS. 50A-50C and for brevity is not repeated.

Pinion gear 524 has forward facing teeth 527 and rearward facing teeth 529. In the non-expansion position (mode) of FIG. 50A, pinion gear teeth 529 are out of engagement with gear teeth 536 of sprocket 534. Therefore, rotation of drive rod 526 via the T-handle (not shown) rotates pinion gear 528 of drive rod 526 to rotate gear 527 and the sprocket 534 and hub (not shown) to rotate the shaver heads in the same manner as rotation of shaver heads 212, 214.

If it is desired to rotate the shaver heads with expansion, the expansion rod 532, which is identical to expansion rod 310 of discectomy tool 200, is moved distally by the slider to engage and lock the sprocket 518 as shown in FIG. 50B. (The slider could be the same as slider 224, or alternatives thereof). In this position, as in the expansion mode of discectomy tool 200 described above, rotation of the pinon gear 524 and shaver head gear 528 effect rotation of the shaver head and movement of the upper shaver head away from the lower shaver head as the hub rotates and the sprocket 534 is locked from rotation. In this expansion mode of FIG. 50B, the rear teeth 529 of pinion gear 524 remain out of engagement with sprocket 534.

If the user desires to expand the shaver heads without rotation of the shaver heads, as shown in FIG. 50C, the expansion rod 532 is moved to the non-expansion position disengaged from the sprocket 534. The drive rod 526, which in this embodiment is movably axially, is retracted (moved proximally) by an actuator at the proximal end so the rear teeth 529 of pinion gear 524 are in engagement with teeth 536 of sprocket 534. Retraction of drive rod 526 proximally moves pinon gear 524 out of engagement with shaver head gear 528. In this position, when drive rod 526 is rotated, pinion gear 524 does not rotate shaver head gear 528 because it is out of engagement, but rotates sprocket 534 due to engagement of pinon gear 524 with gear 536 of sprocket 534. As the sprocket 536 rotates, the upper shaver head unthreads from the threads of sprocket 536. The upper shaver head can engage the sprocket via threads on a post like the threads 239 of post 236 of upper shaver head 212 of the discectomy tool 200. Thus, in this embodiment, the user can control at any time before or during the procedure the axial position of the expansion rod 532 to enable expansion with rotation as well as control any time before or during the procedure the axial position of the drive rod 526 to enable expansion without rotation.

It should be appreciated that various actuators can be utilized to control the expansion rod and drive rod.

FIGS. 43-48C illustrate an alternate embodiment of the discectomy tool of the present invention. In this embodiment, expansion of the upper and lower shaver heads are achieved by a cable mechanism. Body 402 of discectomy tool 400 has a recess 408 to receive sprocket 420 and key 406 to attach the upper and lower shaver heads 212, 214 in the same manner as key 224 of Figure of FIG. 26D discussed above. Lower shaver head 404 is attached to sprocket 420. The upper shaver head is not shown and can be identical to upper shaver head 212 of discectomy tool 200 of FIGS. 21A-26D. The upper and lower shaver heads rotate about an axis transverse to the longitudinal axis of the body 402 in the same manner as shaver heads 212, 214, and such rotation is effected by rotation of handle 410 attached to a drive rod having a pinon gear intermeshing with teeth of a gear attached to the lower shaver head in the same manner as described above for discectomy tool 200. These components are omitted from the drawings for clarity, with the drawings mainly depicting the cable mechanism for effecting expansion of the shaver heads.

In discectomy tool 400, shaver head expansion is independent of rotation so that it can be effected without simultaneous rotation of the shaver heads. An actuation mechanism in the form of a crank, although other mechanisms are also contemplated, is connected to cable 430. Cable 440 forms looped regions 440 at a distal region and is wound around the spool 438 at a proximal region. More specifically, crank 435 has a gripping region 437 and an arm 436 which rotates shaft (spool) 438. Spool 438 is exposed between two larger cylinders 439, forming a reduced diameter region, and the cable 440 wraps (winds) around spool 438 as the arm 436 is rotated. The cable 440 at is distal end is wound about circumferential slot 422 in sprocket 420. Line 446 of cable 440 extends from shaft 438 and wraps around slot 422 in a clockwise direction; line 444 extends from shaft 438 and wraps in a counterclockwise direction.

In use, when the user wishes to effect expansion of the shaver heads to increase their distance, crank 435 is moved in a circular motion to rotate shaft 438. In one embodiment, as arm 436 and shaft 448 rotate in a first clockwise direction. the counterclockwise wound portion of the cable 440 unwinds about slot 422 while the clockwise portion winds around slot 422. In this embodiment, when crank 435 is rotated in an opposite circular motion, i.e., counterclockwise, shaft 448 rotates in the opposite direction wherein the clockwise portion of the cable 440 unwinds while the counterclockwise portion winds around the slot 422. It should be appreciated that in alternate embodiments, the clockwise motion of the crank arm and shaft 438 could wind/unwind different portions of the cable 440 or alternatively, counterclockwise rotation of the arm and shaft could cause the aforementioned winding and unwinding. In any of these variations, this unwinding/winding of the cable, rotates the sprocket 420. Upper shaver head is threadingly engaged with sprocket 430 such that rotation of the sprocket 430 unthreads the upper shaver head to increase its distance from the lower shaver head. In some embodiments, the sprocket can be rotated in the opposite direction by moving the crank arm in the opposite circular motion to move the upper shaver head toward the lower shaver head.

Note it is also contemplated that a cable mechanism, such as the unwinding/winding cable described herein, can be utilized to effect rotation of the upper and lower shaver instead of the gear mechanism disclosed herein. Such cable mechanism for shaver head rotation can be used with the cable mechanism for shaver head expansion or used with other shaver head expansion mechanisms.

The shaver heads of any of the embodiments disclosed herein can be covered during insertion to protect the patient. FIGS. 42A-42F provide an example of such cover. The cover can be made of a sheet of material such as Nitinol by way of example, however, it should be appreciated that other materials are also contemplated. In the insertion position depicted in FIG. 42A, cover 450 is in a closed position enclosing the upper and lower shaver heads to prevent contact with the body, especially where the outer surfaces of the shaver heads have irregular surfaces as described herein. Once in position, the user can retract a rod or other actuator attached to the cover to open the cover 450 to expose the upper and lower shaver heads. As the cover 450 is opened, the opening 456 to expose the shaver heads increases as shown in the progression from FIG. 42C to 42F. The edges of the cover are designated by reference numerals 452 and 454. Once the upper and lower shaver heads are exposed, the shaver heads are ready for use. Note in some embodiments, the shaver heads can be expanded prior to partial or full removal of the cover.

Although the apparatus and methods of the subject invention have been described with respect to preferred embodiments, those skilled in the art will readily appreciate that changes and modifications may be made thereto without departing from the spirit and scope of the present invention as defined by the appended claims. Persons skilled in the art will understand that the various embodiments of the disclosure described herein and shown in the accompanying figures constitute non-limiting examples, and that additional components and features may be added to any of the embodiments discussed herein without departing from the scope of the present disclosure.

It will be understood by those skilled in the art that the above particular embodiments are shown and described by way of illustration only. The principles and the features of the present disclosure may be employed in various and numerous embodiments thereof without departing from the scope and spirit of the disclosure as claimed. The above-described embodiments illustrate the scope of the disclosure but do not restrict the scope of the disclosure.

Although the invention has been described in detail in the foregoing embodiments for the purpose of illustration, it is to be understood that such detail is solely for that purpose, and that variations can be made therein by those skilled in the art without departing from the spirit and scope of the invention.

Additionally, persons skilled in the art will understand that the elements and features shown or described in connection with one embodiment may be combined with those of another embodiment without departing from the scope of the present invention and will appreciate further features and advantages of the presently disclosed subject matter based on the description provided.

Throughout the present invention, terms such as "approximately," "about", "generally," "substantially," and the like should be understood to allow for variations in any numerical range or concept with which they are associated. It is intended that the use of terms such as "approximately", "about", "substantially", and "generally" should be understood to encompass variations on the order of 25%, or to allow for manufacturing tolerances and/or deviations in design.

The recitation of numerical ranges by endpoints includes all numbers within the range.

Although terms such as "first," "second," "third," etc., may be used herein to describe various operations, elements, components, regions, and/or sections, these operations, elements, components, regions, and/or sections should not be limited by the use of these terms in that these terms are used to distinguish one operation, element, component, region, or section from another. Thus, unless expressly stated otherwise, a first operation, element, component, region, or section could be termed a second operation, element, component, region, or section without departing from the scope of the present invention.

Each and every claim is incorporated as further disclosure into the specification and represents embodiments of the present disclosure. Also, the phrases "at least one of A, B, and C" and "A and/or B and/or C" should each be interpreted to include only A, only B, only C, or any combination of A, B, and C.

What is claimed is:

1. A discectomy device for clearing material out of a disc space of a patient, the device comprising:

a) a body having a proximal portion, a distal portion and a longitudinal axis;

b) a first rotatable member at the distal portion of the body;

c) a second rotatable member at the distal portion of the body and spaced from the first rotatable member, wherein a transverse axis passes through the first and second rotatable members, the transverse axis extending transverse to the longitudinal axis, and the first rotatable member being elongated along a longitudinal axis of the first rotatable member and the second rotatable member being elongated along a longitudinal axis of the second rotatable member, wherein the longitudinal axis of the first rotatable member and the longitudinal axis of the second rotatable member are transverse to the transverse axis; and d) wherein the first and second rotatable members rotate about the transverse axis; and e) wherein the first rotatable member has an outer surface and an inner surface, and the second rotatable member has an outer surface and inner surface, the inner surface of the first rotatable member facing the inner surface of the second rotatable member, wherein a distance between the inner surfaces of the first and rotatable members can be increased.

2. The discectomy device of claim 1, wherein the first and second rotatable members are retained in position parallel to one another during insertion and rotation.

3. The discectomy device of claim 1, wherein the first and second rotatable members are retained in a parallel relationship during the increase of the distance between the inner surface of the first rotatable member and the inner surface of the second rotatable members.

4. The discectomy device of claim 1, further including a first mechanism actuable to rotate the first and second rotatable members, wherein the first mechanism includes a first actuator, and the first actuator is actuable to effect rotation of the first and second rotatable members about the transverse axis and to effect movement of at least one of the first and second rotatable members away from the other rotatable member to increase a distance between the first and second rotatable members.

5. The discectomy device of claim 1, further comprising a slidable member movable between an engaged and a disengaged position, wherein in the engaged position, the distance between the first and second rotatable members can be increased and in the disengaged position, the distance between the first and second rotatable members cannot be changed.

6. The discectomy device of claim 1, wherein the first and second rotatable members are separable from the body of the discectomy device for leaving the first and second rotatable members behind in the disc space of the patient.

7. The discectomy device of claim 6, wherein the first and second rotatable members each have a series of openings formed therein to receive graft material.

8. The discectomy device of claim 1, further comprising a cover positioned over at least a portion of the first and second rotatable members for insertion and an actuator to open the cover to expose the first and second rotatable members.

9. The discectomy device of claim 1, wherein the first and second rotatable members having an insertion configuration, and the first and second rotatable members are rotated into an implanted configuration that is different from the insertion configuration, and the first and second members are detachably connected to the body of the discectomy device for release from the body in-situ for implantation within the disc space in the implanted configuration.

10. The discectomy device of claim 9, wherein the first and second rotatable members have a series of openings formed therein to receive graft material.

11. The discectomy device of claim 9, further comprising a plurality of locking members for retaining a position of the first and second rotatable members when left in the disc space.

12. The discectomy device of claim 1, wherein the first and second rotatable members are oblong.

13. A discectomy device for clearing material out of a disc space of a patient, the device comprising:

a) a body having a proximal portion, a distal portion and a longitudinal axis;

b) a first rotatable member at the distal portion of the body;

c) a second rotatable member at the distal portion of the body and spaced from the first rotatable member, wherein a transverse axis passes through the first and second rotatable members, the transverse axis extending transverse to the longitudinal axis, and the first rotatable member being elongated along a longitudinal axis of the first rotatable member and the second rotatable member being elongated along a longitudinal axis of the second rotatable member, wherein the longitudinal axis of the first rotatable member and the longitudinal axis of the second rotatable member are transverse to the transverse axis;

d) wherein the first and second rotatable members rotate about the transverse axis; and e) a first mechanism actuable to rotate the first and second rotatable members, wherein the first mechanism includes an elongated member having a proximal portion and a distal portion, the elongated member positioned within the body and rotatable to actuate a gear mechanism for rotating the first and second rotatable members about the transverse axis.

14. The discectomy device of claim 13, wherein the gear mechanism includes a first gear attached at a distal portion of the elongated member and interacting with a second gear attached to one or both of the first rotatable member and second rotatable member.

15. The discectomy device of claim 13, wherein the first and second rotatable members having an insertion configuration, and the first and second rotatable members are rotated into an implanted configuration that is different from the insertion configuration, and the first and second members are detachably connected to the body of the discectomy device for release from the body in-situ for implantation within the disc space in the implanted configuration.

16. The discectomy device of claim 15, wherein the first and second rotatable members have a series of openings formed therein to receive graft material.

17. The discectomy device of claim 15, further comprising a plurality of locking members for retaining a position of the first and second rotatable members when left in the disc space.

18. A discectomy device for clearing material out of a disc space of a patient, the device comprising:

a) a body having a proximal portion, a distal portion and a longitudinal axis;

b) a first rotatable member at the distal portion of the body;

c) a second rotatable member at the distal portion of the body and spaced from the first rotatable member, wherein a transverse axis passes through the first and second rotatable members, the transverse axis extending transverse to the longitudinal axis, and the first rotatable member being elongated along a longitudinal axis of the first rotatable member and the second rotatable member being elongated along a longitudinal axis of the second rotatable member, wherein the longitudinal axis of the first rotatable member and the longitudinal axis of the second rotatable member are transverse to the transverse axis;

d) wherein the first and second rotatable members rotate about the transverse axis; and e) wherein one or both of the first and second rotatable members are moved along the transverse axis to increase the distance between the first and second rotatable members, and the first and second rotatable members are maintained in a substantially parallel position during such movement along the transverse axis.

19. The discectomy device of claim 18, wherein the first and second rotatable members having an insertion configuration, and the first and second rotatable members are rotated into an implanted configuration that is different from the insertion configuration, and the first and second members are detachably connected to the body of the discectomy device for release from the body in-situ for implantation within the disc space in the implanted configuration.

20. The discectomy device of claim 19, wherein the first and second rotatable members have a series of openings formed therein to receive graft material.

21. The discectomy device of claim 19, further comprising a plurality of locking members for retaining a position of the first and second rotatable members when left in the disc space.

22. A discectomy device for clearing material from a disc space of a patient, the device comprising:

a) a body having a proximal portion, a distal portion and a longitudinal axis;

b) a first rotatable member at the distal portion of the body, the first rotatable member having a first surface and a second surface; and c) a second rotatable member at the distal portion, the second rotatable member spaced from the first rotatable member and having a first surface and a second surface, the second surface of the second rotatable member facing the second surface of the first rotatable member and the first surface of the first rotatable member and the first surface of the second rotatable member being substantially parallel, the first and second rotatable members are rotatable to clear disc material; and d) wherein a distance between the first and second rotatable members is changeable to change the distance between the surfaces of the first and second rotatable members, wherein the surfaces of the first and second rotatable members are maintained substantially parallel when the distance between the surfaces of the first and second rotatable members is changed.

23. The discectomy device of claim 22, wherein the first and second rotatable members are separable from the body of the discectomy device for leaving the first and second rotatable members behind in the disc space of the patient.

24. The discectomy device of claim 22, wherein one or both of the first and second rotatable members are moved along a transverse axis to increase the distance between the first and second rotatable members, and the first and second rotatable members are maintained in a substantially parallel position during such movement along the transverse axis, the transverse axis being perpendicular to the longitudinal axis of the body.

25. The discectomy device of claim 22, further comprising an expansion control member movable between an engaged and a disengaged position, in an engaged position, the distance between the first and second rotatable members can be increased and in a disengaged position, the distance between the first and second rotatable members cannot be changed.

26. The discectomy device of claim 25, further comprising an actuator, the actuator actuable to both adjust the distance between the first and second rotatable members and effect rotation of the first and second rotatable members to clear disc material.

27. The discectomy device of claim 22, wherein the first and second rotatable members having an insertion configuration, and the first and second rotatable members are rotated into an implanted configuration that is different from the insertion configuration, and the first and second members are detachably connected to the body of the discectomy device for release from the body in-situ for implantation within the disc space in the implanted configuration.

28. The discectomy device of claim 27, wherein the first and second rotatable members have a series of openings formed therein to receive graft material.

29. The discectomy device of claim 27, further comprising a plurality of locking members for retaining a position of the first and second rotatable members when left in the disc space.

\* \* \* \* \*